(12) United States Patent
do Couto et al.

(10) Patent No.: US 6,315,997 B1
(45) Date of Patent: Nov. 13, 2001

(54) USE OF MODIFIED ANTIBODIES WITH HUMAN MILK FAT GLOBULE SPECIFICITY

(75) Inventors: Fernando J.R. do Couto, Pleasanton; Roberto L. Ceriani; Jerry A. Peterson, both of Lafayette; Eduardo A. Padlan, Kensinton, all of CA (US)

(73) Assignee: Cancer Research Fund, San Francisco, CA (US)

( * ) Notice: Subject to any disclaimer, the term of this patent is extended or adjusted under 35 U.S.C. 154(b) by 0 days.

(21) Appl. No.: 08/976,288

(22) Filed: Nov. 21, 1997

Related U.S. Application Data

(60) Division of application No. 08/129,930, filed on Sep. 30, 1993, now Pat. No. 5,804,187, which is a continuation-in-part of application No. 07/977,696, filed on Nov. 16, 1992, now Pat. No. 5,792,852.

(51) Int. Cl.[7] .................................................. A61K 39/395
(52) U.S. Cl. ..................................... 424/134.1; 424/133.1; 424/135.1; 424/138.1; 424/178.1; 424/182.1
(58) Field of Search .............................. 424/133.1, 134.1, 424/135.1, 138.1, 178.1, 182.1

(56) References Cited

U.S. PATENT DOCUMENTS

| | | | |
|---|---|---|---|
| 4,708,930 | 11/1987 | Kortright | 435/7.23 |
| 5,075,219 | 12/1991 | Ceriani et al. | 530/388.85 |
| 5,077,220 | 12/1991 | Ceriani et al. | 530/388.85 |

FOREIGN PATENT DOCUMENTS

| | | |
|---|---|---|
| GB 2 188 638 | 10/1988 | (GB) . |
| WO92/04380 | 3/1992 | (WO) . |

OTHER PUBLICATIONS

Varhoeyen, et al., "Reshaping Human Antibodies: Grafting an Antilysozyme Activity", Science 239: 1537–1536 (Mar. 1988).

Tempest, et al., "Reshaping a Human Monoclonal Antibody to Inhibit Human Respiratory Synctial Virus Infection in Vivo", Biotechnology 9: 266–271 (Mar. 1991).

Peterson, et al., "Biochemical and Histological Characterization of Antigens Preferentially Expressed on the Surface and Cytoplasm of Breast Carcinoma Cells Identified by Monoclonal Antibodies Against the Human Milk Fat Globule", Hybridoma 9:221–235 (1990).

Davies, D.R. and Padlan, E.A., "Antibody–Antigen Complexes", Annu. Rev. Biochem. 59:439–73 (1990).

Riechmann, L., et al., 37 Reshaping Human Antibodies for Therapy:, Nature 332:323–327 (1988).

Kramer, E.L. et al., "Initial Clinical Evaluation of Radiolabeled MX–DTPA Humanized BrE–3 Antibody in Patients with Advanced Breast Cancer", Clinical Cancer Research, 4:1679–1688, Jul. 1998.

Waldmann, Thomas A. "Monoclonal Antibodies in Diagnosis and Therapy" Science. vol. 252, pp.1657–1662, Jun. 1991.

*Primary Examiner*—Sheela Huff
(74) *Attorney, Agent, or Firm*—Viviana Amzel

(57) ABSTRACT

An analogue peptide that comprises the variable regions of the light or heavy chains of an antibody of a first species selectively binding to a carcinoma antigen has 1 to 46 amino acids of the framework regions per chain substituted with amino acids such as those present in equivalent positions in antibodies of a species other than the first species, or fragments thereof comprising 1 to 3 variable region CDRs per chain and optionally flanking regions thereof of 1 to 10 or more amino acids, alone or with an N-terminal fragment of 1 to 10 or more amino acids, combinations or mixtures thereof. The polypeptide may also comprise an effector agent and/or be glycosylated, and is presented as a composition with a carrier. The analogue peptides are used in diagnostic kits for carcinomas and methods for in vivo imaging and treating a primary or metastasized carcinoma, and in vitro diagnosing a carcinoma, ex vivo purging neoplastic cells from a biological fluid. RNAs and DNAs encode the analogue peptide, and a hybrid vector carrying the nucleotides and transfected cells express the peptides and a method produces the analogue peptide. An anti-idiotype polypeptide comprises polyclonal antibodies raised against an anti-carcinoma antibody or the analogue peptide of this invention, monoclonal antibodies thereof, Fab, Fab', (Fab')$_2$, CDR, variable region, or analogues or fragments thereof, combinations thereof with an oligopeptide comprising a TRP trimer, tandem repeats thereof, or combination or mixtures thereof. An anti-idiotype hybrid polypeptide with an effector agent and the anti-idiotype polypeptide, an anti-carcinoma vaccine, an anti-carcinoma vaccination kit, a method of vaccinating against carcinoma and a method of lowering the serum concentration of a circulating antibody or polypeptide are provided.

65 Claims, No Drawings

USE OF MODIFIED ANTIBODIES WITH HUMAN MILK FAT GLOBULE SPECIFICITY

This application is a divisional of U.S. Ser. No. 08/129,930, entitled "MODIFIED ANTIBODIES WITH HUMAN MILK FAT GLOBULE SPECIFICITY", filed on Sep. 30, 1993, by the same inventors, now U.S. Pat. No. 5,804,187, which is a continuation-in-part of U.S. Ser. No. 07/977,696, entitled "POLYNUCLEOTIDES ENCODING MODIFIED ANTIBODIES WITH HUMAN MILK FAT GLOBULE SPECIFICITY", filed Nov. 16, 1992, by Do Couto, Ceriani and Peterson, now U.S. Pat. No. 5,792,852.

BACKGROUND OF THE INVENTION

1. Field of the Invention

This invention relates to the in vitro and in vivo diagnosis, immunization, and therapy of neoplastic tumors, particularly carcinomas, by means of specifically targeted analogue peptides comprising amino acid sequences encompassing the complementarity determining regions (CDRs) of a different species, and analogues of the variable ($F_v$) region of anti-carcinoma antibodies, among others. The carcinoma specific peptides for use in one species, e.g., humans, are provided as a single amino acid chain having the specificity of $F_v$ regions obtained in different species, e.g., murine antibody $F_v$ regions of the light or heavy chains, or as paired chains. These peptides are provided either by themselves or bound to other molecules such as synthetic polymers or oligopeptides resulting in sequences of mixed species, and more particularly analogues of human/non-human chimeric antibodies or other polymeric constructs. The analogue peptides comprise sequences derived from the variable regions of heterologous antibodies specific for, e.g., human carcinoma antigens that elicit a lesser immunological response in humans than the whole heterologous antibodies. The anti-idiotype polypeptides and their analogues are suitable for immunizing humans or other animals against carcinoma. Polynucleotide segments encoding the analogue peptide and anti-idiotype polypeptides, and hybrid vectors and transfected host cells carrying the segments are useful for preparing the peptides disclosed herein.

2. Description of the Background

Carcinomas result from the carcinogenic transformation of cells of different epithelia. Two of the most damaging characteristics of carcinomas are their uncontrolled growth and their ability to create metastases in distant sites of the host, particularly a human host. It is usually these distant metastases that cause serious consequences to the host, since frequently the primary carcinoma may be, in most cases, removed by surgery. The treatment of metastatic carcinomas, that are seldom removable, depends on irradiation therapy and systemic therapies of different natures. The systemic therapies currently include, but not fully comprise, chemotherapy, radiation, hormone therapy, different immunity-boosting medicines and procedures, hyperthermia and systemic monoclonal antibody treatment. The latter can be labeled with radioactive elements, immunotoxins and chemotherapeutic drugs.

Radioactively labeled monoclonal antibodies were initially used with success in lymphomas and leukemia, and recently in some carcinomas. The concept underlying the use of labeled antibodies is that the labeled antibody will specifically seek and bind to the carcinoma and, the radioactive element, through its decay, will irradiate the tumor in situ. Since radioactive rays travel some distance in tumors it is not necessary that every carcinoma cell bind the labeled antibody. The specificity of the monoclonal antibodies will permit a selective treatment of the tumor while avoiding the irradiation of innocent by-stander normal tissues, that could be dose limiting. Chemotherapy produces serious toxic effects on normal tissues, making the chemotherapy of carcinomas less than desirable, and the use of radiolabeled monoclonal antibodies a valid alternative.

Non-human antibodies raised against human epitopes have been used for the diagnosis and therapy of carcinomas as is known in the art. Also known are the methods for preparing both polyclonal and monoclonal antibodies. Examples of the latter are BrE-2, BrE-3 and KC-4 (e.g., U.S. Pat. Nos. 5,077,220; 5,075,219 and 4,708,930).

The KC-4 murine monoclonal antibody is specific to a unique antigenic determinant, the "antigen", and selectively binds strongly to neoplastic carcinoma cells and not to normal human tissue (U.S. Pat. No. 4,708,930 to Coulter). The antigen appears in two forms in carcinoma cells, only the smaller of these forms being expressed in the cell membrane. The larger form appears only in the cytoplasm and has an approximate 490 Kdalton molecular weight (range of 480,000–510,000). The second form occurs at a higher density of expression, is found both in the cytoplasm and the membrane of carcinoma cells and has an approximate 438 Kdalton molecular weight (range of 390,000–450,000) as determined by gel electrophoresis with marker proteins of known molecular weights. Labeled KC-4 was applied to the diagnosis and medical treatment of various carcinomas, particularly adenocarcinoma and squamous cell carcinoma regardless of the human organ site of origin.

The BrE-3 antibody (Peterson et al., Hybridoma 9:221 (1990); U.S. Pat. No. 5,075,219) was shown to bind to the tandem repeat of the polypeptide core of human breast epithelial mucin. When the mucin is deglycosylated, the presence of more tandem repeat epitopes is exposed and the binding of the antibody increases. Thus, antibodies such as BrE-3 bind preferentially to neoplastic carcinoma tumors because these express an unglycosylated form of the breast epithelial mucin that is not expressed in normal epithelial tissue. This preferential binding combined with an observed low concentration of epitope for these antibodies in the circulation of carcinoma patients, such as breast cancer patients, makes antibodies having specificity for a mucin epitope highly effective for carcinoma radioimmunotherapy. A 90Y-BrE-3 radioimmunoconjugate proved highly effective against human breast carcinomas transplanted into nude mice. Human clinical studies showed the 90Y-BrE-3 radioimmunoconjugate to considerably reduce the size of breast tumor metastases without any immediate toxic side effects. Moreover, an 111In-BrE-3 radioimmunoconjugate was successfully used for imaging 15 breast cancer patients, providing excellent tumor targeting in 13 out of 15 of the patients. Out of all the breast tumor metastases occurring in another study, 86% were detected by 111In-BrE-3. Unfortunately, 2 to 3 weeks after treatment, the patients developed a strong human anti-murine antibody (HAMA) response that prevented further administration of the radioimmunoconjugate. The HAMA response, which is observed for numerous murine monoclonal antibodies, precludes any long-term administration of murine antibodies to human patients. Similarly, other heterologous antibodies, when administered to humans, elicited similar antibody responses. The anti-heterologous human response is, thus, a substantial limiting factor hindering the successful use of heterologous monoclonal antibodies as therapeutic agents, which could, otherwise, specifically annihilate breast carcinomas, causing little or no damage to normal tissue and having no other toxic effects.

Chimeric antibodies are direct fusions between variable domains of one species and constant domains of another. Murine/human chimeric antibodies prepared from other types of B cells binding to other types of antigenic determinants have been shown to be less immunogenic in humans than whole murine antibodies. These proved to be less immunogenic but still in some cases an immune response is mounted to the rodent variable region framework region (FR). A further reduction of the "foreign" nature of the chimeric antibodies was achieved by grafting only the CDRs from a rodent monoclonal into a human supporting framework prior to its subsequent fusion with an appropriate constant domain, (European Patent Application, Publication No. 239,400 to Winter; Riechmann, et al., Nature 332:323–327 (1988)). However, the procedures employed to accomplish CDR-grafting often result in imperfectly "humanized" antibodies. That is to say, the resultant antibody loses avidity (usually 2–3 fold, at best).

The ligand binding characteristics of an antibody combining site are determined primarily by the structure and relative disposition of the CDRs, although some neighboring residues also have been found to be involved in antigen binding (Davies, et al., Ann. Rev. Biochem. 59:439–473 (1990)).

The technologies of molecular biology have further expanded the utility of many antibodies by allowing for the creation of class switched molecules whose functionality has been improved by the acquisition or loss of complement fixation. The size of the bioactive molecule may also be reduced so as to increase the tissue target availability of the antibody by either changing the class from an IgM to an IgG, or by removing most of the heavy and light chain constant regions to form an Fv antibody. Common to all of these potentially therapeutic forms of antibody are the required complementary determining regions (CDRs), which guide the molecule to its ligand, and the framework residues (FRs) which support the CDRs and dictate their disposition relative to one another. The crystallographic analysis of numerous antibody structures revealed that the antigen combining site is composed almost entirely of the CDR residues arranged in a limited number of loop motifs. The necessity of the CDRs to form these structures, combined with the appreciated hypervariability of their primary sequence, leads to a great diversity in the antigen combining site, but one which has a finite number of possibilities. Thus, its hypermutability and the limited primary sequence repertoire for each CDR would suggest that the CDRs derived for a given antigen from one species of animal would be the same derived from another species. Hence, they should be poorly immunogenic, if at all, when presented to a recipient organism.

Accordingly, there is still need for a product of high affinity and/or specificity for carcinoma antigens suitable for the detection and therapy of carcinomas which elicits a lesser antibody response than whole non-human antibodies or chimeric antibodies containing, for instance the entire non-human variable region.

SUMMARY OF THE INVENTION

This invention relates to an analogue peptide and its glycosylated derivative which specifically and selectively binds to an antigen found on the surface or in the cytoplasm of carcinoma cells or that is released by the cells, the analogue peptide consisting essentially of at least one variable region of the light or heavy chains of an antibody of a first species having affinity and specificity for an antigen found on the surface or the cytoplasm of a carcinoma cell or released by the cell, wherein preferably about 1 to at least 46 amino acids in the FR are substituted per chain with amino acids selected from the group consisting of amino acids present in equivalent positions in antibodies of a species other than the first species, or fragments thereof comprising 1 to 3 CDRs per chain or 1 to 3 CDRs plus flanking regions thereof, each of about 1 to at least 10 amino acids, alone or plus an N-terminal fragment of about 1 to at least 10 amino acids, combinations thereof, or combinations thereof with other variable regions or analogues thereof, wherein each analogue peptide is operatively linked to at least one other peptide or analogue thereof, or mixtures thereof.

Also provided herein are a fusionprotein and a hybrid polymer comprising the analogue of the invention, the corresponding DNAs encoding them, hybrid vector thereof, transfected host thereof, and RNA.

This invention also encompasses a method of producing an analogue peptide or hybrid analogue peptide by recombinant technology, in vitro methods of diagnosing and immunohistochernistry of tissue slices, an ex vivo method of purging neoplastic cells, and in vivo methods for imaging and therapy of neoplasias such as carcinomas.

Also disclosed herein are anti-idiotype polypeptides comprising polyclonal antibodies raised against the analogue peptide of this invention, analogues thereof, monoclonal antibodies thereof, fragments thereof selected from the group consisting of Fab, Fab', (Fab')2, CDRs, variable regions and analogues thereof as described above, combinations thereof operatively linked to one another, an anti-carcinoma vaccine, a vaccination kit, a method of vaccinating against neoplasias including carcinomas, and a method of lowering the serum concentration of circulating anti-tumor antibody with the anti-idiotype polypeptide of this invention.

Other objects, advantages and features of the present invention will become apparent to those skilled in the art from the following discussion.

DESCRIPTION OF THE PREFERRED EMBODIMENTS

This invention arose from a desire by the inventors to improve on antibody technology suitable for use in diagnostic, prognostic, vaccine and therapeutic applications. The present invention will be described for application to humans. However, it is also suitable for use in other species. The monoclonal antibodies obtained up to the present time have been prepared by fusing immortalized cell lines with B-cells of non-human origin such as murine, rat, rabbit, goat, and the like. Many of these hybridomas can produce large quantities of monoclonal antibodies that have desirable binding properties such as high affinity and/or specificity and selectivity for carcinoma antigens of a species, e.g., for human carcinoma antigens. However, in general, antibodies from another species, e.g., non-human antibodies, may only be administered once to a subject of a predetermined species, e.g., humans, due to the detrimental effects they produce. This is true for most heterologous antibodies being administered to mammalian animals. For example, the repeated administration of murine antibodies to a human subject elicits a strong human anti-murine antibody (HAMA) response, which precludes their further utilization as therapeutic agents in humans. These non-human antibodies initiate an immediate adverse reaction in many human patients and are, thus, rendered ineffective for further administration as therapeutic agents. In some cases, non-humanhuman chimeric antibodies and non-human CDR "grafted"-human antibodies may have lower affinity and/or specificity for their antigens than the corresponding non-human antibody. On the other hand, human monoclonal hybridoma cell lines have not been very stable and have, therefore, not been suitable for the large scale, repeated production of monoclonal antibodies.

The present invention is applicable to the manufacture of analogue peptides having a high number of amino acids in the respective positions found in the endogenous antibodies, and where at least the CDRs are of another xenogeneic species.

The present inventors, thus, have undertaken the preparation of anti-carcinoma non-human CDRs and non-human variable regions of antibodies, having affinity and specificity for an antigen found on the surface or the cytoplasm of a human carcinoma cell or released by the cells, wherein about 1 to 46 amino acids in the framework region (FR) are substituted per chain with amino acids present in equivalent positions in other human antibodies, or fragments thereof comprising 1 to 3 CDRs per chain or 1 to 3 CDRs per chain plus flanking regions thereof, each of about 1 to 10 or more amino acids, alone or plus an N-terminal fragment of about 1 to 10 or more amino acids, to lower or even circumvent the anti-xenogeneic response. To preserve substantial binding specificity in the molecules intended for use in humans, the present invention utilizes CDRs and/or analogues of varying lengths of the variable regions of light and/or heavy chains of other species such as murine, rat, rabbit, goat, equine, primate, bovine, and guinea pig antibodies, among others, and heterologous human CDRs and/or analogues of variable regions may be utilized when they are intended for use in other species.

The present inventors have found, surprisingly, that these analogue antibody fragments substantially preserve the binding, specificity and selectively characteristics of the whole non-human antibody while eliciting a lesser detrimental immunological response. However, the simple preservation of the binding region of an antibody does not by itself ensure that the binding characteristics of the antibody will be maintained. Antibodies are glycopolypeptides that are folded into specific conformations. When the glycoside portion of the molecule or portions of the amino acid sequence are perturbed or excised, the folding pattern of the molecule may be perturbed. Thus, any deletion or modification of the sequence of an antibody must be made taking into consideration that its folding-dependent properties may be diminished or even obliterated if the folding is substantially affected, even though the amino acid sequences involved in the binding of the antigen are preserved.

The present inventors selected the following strategy for the preparation and manufacture of the analogue and hybrid peptides of this invention. The cDNAs that encode the variable chains of an antibody may be obtained by isolation of mRNA from a hybridoma cell and reverse transcription of the mRNA, amplification of the cDNA by polymerase chain reaction (PCR) and insertion of the DNA into a vector for optional sequencing, and for restriction enzyme cutting. The cDNAs encoding the CDRs or variable chain (Fv) region fragments of the light (VL) and heavy (VH) chains of an antibody having affinity and specificity for a carcinoma cell antigen may be reverse transcribed from isolated mRNA. The cDNAs encoding the CDRs may then be ligated to other segments encoding neighboring sequences, and the variable region cDNAs may then be modified with predesigned primers used to PCR amplify them or synthesized de novo, cloned into a vector optionally carrying DNA sequences encoding, e.g., a constant region(s), optionally sequenced, and then transfected into a host cell for expression of the analogue gene product. The binding specificity characteristics of the analogue peptides may then be determined and compared to those of the whole antibodies.

X-ray crystallographic studies demonstrate that the framework structures of the Fv of different antibodies assume a canonical structure regardless of the species of origin, amino acid sequence, or ligand specificity. This is generally taken as evidence that the ligand-binding characteristics of an antibody combining site are determined primarily by the structure and relative disposition of the CDRs, although some neighboring framework residues may also be involved in antigen-binding. Thus, if the fine specificity of an antibody is to be preserved, its CDR structures, and probably some of the neighboring residues, their interaction with each other and with the rest of the variable domains, must also be maintained. These crystallographic studies point to the possible need for retaining most, if not all, of the many interior and inter-domain contact residues since the structural effects of replacing only a few of them cannot be predicted.

While at first the necessity of keeping these amino acids might seem to defeat the goal of decreasing immunogenicity by "humanization", the actual number of amino acids that must be retained is usually small because of the striking similarity between human and murine variable regions. Moreover, many, if not most, of the retained amino acids possess side chains that are not exposed on the surface of the molecule and, therefore, may not contribute to its antigenicity. Clearly, it is most of the exposed amino acids that are good candidates for substitution since it is these amino acids that are exposed to the immunological environment of a mammal and may form epitopes of increased immunogenicity.

The challenge in humanizing the variable regions of a non-human antibody, e.g., a murine antibody, thus begins with the identification of the "important" xenogeneic amino acids. "Important" amino acids are those, for example, that are involved in antigen binding, contact the CDRs and the opposite chains, and have buried side-chains. Ideally, these residues might be identified from a well characterized three-dimensional structure. However, when direct structural data are not available, it is, fortunately, still possible to predict the location of these important amino acids by analyzing other related antibody structures, especially those whose variable light and heavy regions belong to the same class. The classes of variable regions can be determined from their amino acid sequence.

A method by which these important amino acids are identified has been described for the case of the amino acids with buried side chains by Padlan, E. A. (Padlan, E. A., "A Possible Procedure for Reducing the Immunogenicity of Antibody Variable Domains While Preserving Their Ligand-Binding Properties", Molecular Immunology, 28:489–494 (1991)). In the present case, various antibody variable region structures were compared using a computer program that determines the solvent accessibility of the framework residues as well as their contacts with the opposite domain as described by Padlan, E. A. (1991), supra. Surprisingly, a close examination of the fractional solvent accessibility reveals a very close similarity in the exposure patterns of the VH and the VL domains. Put in simple terms, regardless of the particular antibody in question, and of its amino acid sequence, the buried residues occupy similar relative positions in most antibodies.

A similar analysis can be done by computer modeling, to determine which amino acids contact the CDRs and which contact the opposite domain. At this point, the Fab structures that are currently in the Protein Data bank (Bernstein, F. C., et al., J. Mol. Biol. 112:535–542 (1977)) may be examined to determine which FRs are probably important in maintaining the structure of the combining site. Thus, after a close inspection of many high resolution three-dimensional structures of variable regions, the positions of all important framework amino acids, that is, those that contact the CDRs, the opposite domain, and those whose side chains are inwardly pointed, may be tabulated. Keeping these amino acids, as well as those from the CDRs, and finally those FR amino acids that may be involved in ligand binding, should insure to a great extent the preservation of affinity. The precise identification of FR amino acids that are involved in ligand-binding cannot be generalized since it varies for different antibodies. Nevertheless, conservative decisions can be made to preserve the amino acids located in FR that have a high probability of contacting the antigen. These regions are located immediately adjacent to the CDRs and at the N-terminus of both chains, because the surfaces of these regions are contiguous with the CDR surfaces.

Surprisingly, it is possible to keep all of these important amino acids in a heterologous humanized antibody and still increase dramatically the similarity with a human consensus sequence. That is, the final number of amino acids with murine identities differing from human identities that are kept is typically small. This is usually possible because human frameworks that are similar to the murine frameworks, especially at the positions of the important amino acids, can be found. This is because many of the important amino acids have the same identities in both murine and human antibodies.

All the amino acids that are determined to be not important by the method described above may be completely replaced by their corresponding human counterparts. The surface of the finally humanized antibody should look very much like that of a human antibody except for the antigen binding surfaces. The original shape of those binding surfaces, however, is maintained by leaving the internal composition of the antibody intact, preserving inter-domain contacts and by keeping very few key amino acids that contact the CDRs.

a) Choosing the Best Human Framework to Use in the "Humanization" of an Antibody When its Structure is Known At the present time, there are 11 Fab structures for which the atomic coordinates are known and have been placed in the Protein Data Bank as shown in Table 1 below, 2 from human and 9 from murine antibodies.

TABLE 1

Fab Structures for Which Coordinates are in the Protein Data Bank

| | ANTIBODY | RESOLUTION (A) | R-VALUE | PDB CODE |
|---|---|---|---|---|
| HUMAN: | NEWM | 2.0 | 0.46 | 3FAB |
| | KOL | 1.9 | 0.189 | 2FB4 |
| MURINE: | McPC603 | 2.7 | 0.225 | 1MCP |
| | J539 | 1.95 | 0.194 | 2FBJ |
| | HyHEL-5 | 2.54 | 0.245 | 2HFL |
| | HyHEL-10 | 3.0 | 0.24 | 3HEM |
| | R19.9 | 2.8 | 0.30 | 1F19 |
| | 4-4-20 | 2.7 | 0.215 | 4FAB |
| | 36-71 | 1.85 | 0.248 | 6FAB |
| | B13r2 | 2.8 | 0.197 | 1IGF |
| | D1.3 | 2.5 | 0.184 | 1FDL |

The contacts between side chains in the variable domains of the 11 Fabs have been collected and are presented in Tables 2 to 4 below. The framework (FR) amino acids (aa's) in the $V_L$ domains that contact CDRs are listed in Table 2 below.

TABLE 2

$V_L$ Framework Residues That Contact CDR Residues in Fabs of Known Three-Dimensional Structure Antibody

| Position | J539 | McPC603 | HyHEL-10 | HyHEL-5 | R19.9 | 4-4-20 | 36-71 | B13I2 | 01.3 | NEWM | KOL |
|---|---|---|---|---|---|---|---|---|---|---|---|
| 1 | GLU(2) | ASP(5) | ASP(10) | ASP(3) | | ASP(8) | ASP(4) | | ASP(11) | | |
| 2 | ILE(11) | ILE(55) | ILE(17) | ILE(13) | ILE(5) | VAL(9) | ILE(20) | VAL(9) | ILE(10) | SER(3) | |
| 3 | | vAL(3) | VAL(2) | VAL(3) | GLN(2) | VAL(2) | GLN(2) | LEU(5) | | VAL(2) | |
| 4 | LEU(7) | MET(6) | LEU(6) | LEU(10) | MET(9) | MET(13) | MET(7) | MET(6) | MET(7) | LEU(4) | LEU(6) |
| 5 | | THR(1) | | | THR(1) | | | | | THR(1) | |
| 7 | | | | | | | | THR(4) | | | |
| 22 | | | | | | | | SER(6) | | | |
| 23 | CYS(1) | CYS(1) | CYS(2) | CYS(2) | CYS(1) | CYS(1) | CYS(1) | | | | CYS(1) |
| 35 | TRP(3) | TRP(2) | TRP(4) | | TRPi2o | | TRP(6) | trp(4) | TRP(4) | TRP(1) | TRP(2) |
| 36 | Tyr(12) | TyR(16) | TYR(8) | TYR(10) | TYR(22) | TYR(13) | TYR(15) | TYR(8) | TYR(14) | TYR(13) | TYR(11) |
| 45 | | | | | LYS(12) | LYS(5) | | | | | |
| 46 | PRO(3) | LEU(6) | LEU(4) | ARG(15) | LEU(5) | VAL(14) | LEU(5) | LEU(10) | LEU(6) | LEU(2) | LEU(6) |
| 48 | ILE(1) | ILE(1) | ILE(1) | | | | ILE(3) | ILE(2) | VAL(1) | | ILE(1) |
| 49 | TYR(28) | TYR(29) | LUS(13) | TYR(12) | TYR(40) | TYR(22) | TYR(22) | TYR(16) | TYR(25) | | TYR(25) |
| 58 | VAL(3) | VAL(3) | ILE(1) | VAL(6) | VAL(6) | VAL(5) | VAL(4) | VAL(5) | VAL(1) | | VAL(6) |
| 60 | | ASP(1) | | | | | ASP(2) | | ASP(4) | | ASP(2) |
| 62 | | | | PHE(1) | | | PHE(1) | PHE(1) | | | |
| 66 | | | | | | | | | | LYS(2) | LYS(11) |
| 67 | | SER(3) | | | | | | | SER(1) | | |
| 69 | | THR(3) | THR(3) | | | THR(5) | THR(1) | THR(1) | THR(1) | SER(1) | |
| 70 | | ASP(2) | | | ASP(1) | | ASP(6) | | | SER(2) | |
| 71 | TYR(14) | TYR(23) | PHE(17) | TYR(17) | TYR(24) | PHE(17) | TYR(17) | PHE(19) | TYR(16) | ALA(3) | ALA(4) |
| 88 | CYS(1) | | CYS(2) | | CYS(1) | CYS(1) | CYS(1) | CYS(1) | CYS(2) | | CYS(1) |
| 98 | PHE(8) | PHE(8) | PHE(10) | PHE(5) | PHE(8) | PHE(4) | PHE(8) | PHE(14) | PHE(14) | PHE(3) | PHE(7) |

Those FR in the $V_H$ domains that contact CDRs are listed in Table 3 below.

TABLE 3

$V_H$ Framework Residues That Contact CDR Residues in Fabs of Known Three-Dimensional Structure

| Position | J539 | McPC603 | HyHEL-10 | HyHEL-5 | R19.9 | 4-4-20 | 36-71 | B13I2 | 01.3 | NEWM | KOL |
|---|---|---|---|---|---|---|---|---|---|---|---|
| 1 | | | | | | | GLU(3) | | | | |
| 2 | VAL(11) | VAL(3) | VAL(8) | | VAL(1) | | VAL(7) | VAL(3) | VAL(12) | | VAL(9) |
| 4 | LEU(2) | LEU(5) | LEU(5) | | LEU(2) | LEU(1) | LEU(1) | LEU(1) | LEU(1) | | LEU(1) |
| 24 | | THR(2) | VAL(6) | | | ALA(1) | | | | | |
| 27 | PHE(3) | PHE(2) | | TYR(14) | TYR(11) | PHE(26) | TYR(4) | PHE(4) | PHE(4) | THR(1) | PHE(3) |
| 28 | ASP(9) | THR(5) | | THR(3) | THR(6) | THR(4) | THR(2) | THR(3) | | SER(1) | ILE(2) |
| 29 | PHE(4) | PHE(4) | | PHE(10) | PHE(7) | PHE(13) | PHE(6) | PHE(3) | LEU(1) | | PHE(4) |
| 30 | | | THR(2) | | THR(6) | SER(7) | | | | ASP(6) | |
| 36 | | | | | | | TRP(2) | | | | |
| 37 | | VAL(1) | | | VAL(1) | | | | VAL(1) | VAL(2) | VAL(1) |
| 38 | ARG(1) | ARG(2) | ARG(4) | LYS(2) | LYS(1) | ARG(4) | LYS(2) | ARG(1) | | | ARG(3) |
| 40 | | | | ARG(1) | | | | | | | |
| 46 | GLU(3) | GLU(4) | GLU(1) | GLU(27) | GLU(3) | GLU(4) | GLU(9) | | GLU(1) | | GLU(1) |
| 47 | TRP(21) | TRP(29) | TYR(20) | THR(21) | TRP(13) | TRP(18) | TRP(21) | TRP(23) | TRP(19) | TRP(22) | TRP(15) |
| 48 | ILE(1) | ILE(1) | MET(6) | ILE(12) | ILE(13) | VAL(1) | ILE(9) | VAL(3) | LEU(1) | ILE(2) | VAL(1) |
| 49 | | ALA(2) | | | | ALA(2) | | ALA(2) | | | ALA(2) |
| 66 | | ARG(11) | | | | ARG(3) | | ARG(2) | | ARG(2) | ARG(1) |
| 67 | PHE(4) | PHE(10) | ILE(9) | ALA(1) | | PHE(11) | THR(5) | PHE(12) | LEU(6) | VAL(2) | PHE(10) |
| 68 | | ILE(1) | | | THR(1) | THR(11) | | | | | THR(2) |
| 69 | ILE(9) | VAL(6) | ILE(8) | PHE(12) | LEU(5) | ILE(20) | LEU(6) | ILE(11) | ILE(8) | MET(4) | ILE(9) |
| 71 | ARG(7) | ARG(16) | ARG(2) | ALA(1) | VAL(4) | ARG(6) | VAL(6) | ARG(3) | LYS(4) | | ARG(9) |
| 73 | AN(1) | THR(3) | | | | ASP(3) | | | | | |
| 78 | LEU(4) | LEU(7) | TYR(9) | ALA(1) | ALA(1) | VAL(2) | ALA(1) | LEU(6) | VAL(4) | PHE(5) | LEU(5) |
| 80 | | | | | | LEU(1) | | | | | |
| 82 | | | LEU(2) | | | | | | MET(1) | LEU(1) | |
| 86 | | | | | | ASP(2) | | | | | |
| 92 | | | | CYS(1) | | | CYS(1) | | CYS(1) | | |
| 93 | ALA(4) | ALA(5) | | LEU(2) | | THR(3) | ALA(1) | THR(5) | ALA(4) | ALA(1) | ALA(3) |
| 94 | ARG(38) | ARG(24) | ASN(11) | HIS(2) | ARG(30) | | ARG(23) | ARG(14) | ARG(30) | ARG(22) | ARG(27) |
| 103 | TRP)5 | TRP(9) | | | TRP(2) | TRP(2) | TRP(5) | | TRP(2) | TRP(4) | TRP(4) |

The FR amino acids, that contact the opposite domain and which presumably are the ones mainly responsible for the quaternary structure of the $F_v$ domains are listed in Table 4 below.

TABLE 4

Framework Residues That Contact Framework Residues in the Opposite Domain in Fabs of Known Three-Dimensional Structure

| POSITION | J539 | McPC603 | HyHEL-10 | HyHEL-5 | R19.9 | 4-4-20 | 36-71 | B13I2 | 01.3 | NEWM | KOL |
|---|---|---|---|---|---|---|---|---|---|---|---|
| 36 | TYR(3) | TYR(4) | TYR(3) | TYR(5) | | TYR(11) | TYR(7) | TYR(1) | TYR(7) | | TYR(5) |
| 38 | GLN(10) | GLN(4) | GLN(9) | GLN(5) | GLN(5) | GLN(3) | GLN(6) | GLN(12) | GLN(6) | GLN(7) | GLN(8) |
| 43 | SER(7) | PRO(1) | SER(8) | SER(5) | THR(3) | | | SER(3) | SER(2) | ALA(5) | ALA(1) |
| 44 | PRO(10) | PRO(14) | PRO(8) | PRO(11) | | PRO(7) | ILE(20) | PRO(16) | PRO(16) | PRO(7) | PRO(13) |
| 46 | | | | | | | | | | | |
| 85 | TYR(6) | | MET(2) | | THR(5) | | | VAL(1) | | ASP(12) | |
| 87 | PHE(11) | TYR(4) | PHE(6) | TYR(2) | | | PHE(5) | TYR(10) | TYR(8) | TYR(6) | TYR(6) |
| 98 | | PHE(8) | PHE(7) | PRE(2) | PHE(12) | PHE(22) | PHE(8) | PHE(13) | PHE(12) | PHE(10) | PHE(15) |
| 100 | | ALA(2) | | | | | | | | | |

IN $V_2$:

| 37 | VAL(4) | | ILE(2) | VAL(1) | VAL(4) | VAL(3) | VAL(1) | VAL(2) | VAL(4) | VAL(1) | VAL(4) |
|---|---|---|---|---|---|---|---|---|---|---|---|
| 39 | GLN(10) | GLN(4) | LYS(8) | GLN(5) | GLN(5) | GLN(3) | GLN(6) | GLN(10) | GLN(6) | GLN(4) | GLN(7) |
| 43 | | | ASH(4) | | GLN(7) | | | LYS(6) | | ARG(19) | |
| 44 | | ARG(2) | | | | | | | | | |
| 45 | LEU(13) | LEU(12) | LEU(8) | LEU(14) | | LEU(8) | LEU(11) | LEU(13) | LEU(14) | LEU(11) | LEU(16) |
| 47 | TRP(1) | | TYR(2) | | TRP(2) | | | | TRP(3) | TRP(2) | |
| 91 | TYR(6) | TYR(4) | TYR(3) | TYR(8) | PHE(3) | TYR(2) | PHE(4) | TYR(3) | TYR(5) | TYR(3) | |
| 103 | TRP(11) | TRP(15) | TRP(16) | TRP(11) | TRP(4) | TRP(18) | TRP(24) | TRP(24) | TRP(19) | TRP(9) | TRP(19) |
| 105 | GLN(5) | | | | | | | | | | |

The buried, inward-pointing FR amino acids in the $V_L$ domains, i.e., those which are located in the domain interior, are listed in Table 5 below.

TABLE 5

Inward-Pointing, Buried Framework Residues in the $V_L$ of Fabs of Known Three-Dimensional Structure

| | Antibody | | | | | | | | | | |
|---|---|---|---|---|---|---|---|---|---|---|---|
| Position | J539 | McPC603 | HyHEL-10 | HyHEL-5 | R19.9 | 4-4-20 | 36-71 | B13I2 | 01.3 | NEWM | KOL |
| 2 | ILE | ILE | ILE | ILE | ILE | VAL | ILE | VAL | ILE | | |
| 4 | LEU | MET | LEU | LEU | MET | MET | MET | MET | MET | LEU | LEU |
| 6 | GLN | GLN | GLN | GLN | GLN | GLN | GLN | GLN | GLN | GLN | GLN |
| 11 | THR | LEU | LEU | MET | LEU | LEU | LEU | LEU | LEU | VAL | ALA |
| 13 | ALA | VAL | VAL | VAL | VAL | VAL | VAL | VAL | VAL | | |
| 19 | VAL | VAL | VAL | VAL | VAL | VAL | VAL | ALA | VAL | VAL | VAL |
| 21 | ILE | MET | LEU | MET | ILE | ILE | ILE | ILE | ILE | ILE | ILE |
| 23 | CYS | CYS | CYS | CYS | CYS | CYS | CYS | CYS | CYS | CYS | CYS |
| 35 | TRP | TRP | TRP | TRP | TRP | TRP | TRP | TRP | TRP | TRP | TRP |
| 37 | GLN | GLN | GLN | GLN | GLN | LEU | GLN | LEU | GLN | GLN | GLN |
| 47 | TRP | LEU | LEU | TRP | LEU | LEU | LEU | LEU | LEU | LEU | LEU |
| 48 | ILE | ILE | ILE | ILE | VAL | ILE | ULE | ILE | VAL | | ILE |
| 49 | | | | | | | | | | PHE | |
| 58 | VAL | VAL | ILE | VAL | VAL | VAL | VAL | VAL | VAL | | VAL |
| 61 | ARG | ARG | ARG | ARG | ARG | ARG | ARG | ARG | ARG | | ARG |
| 62 | PHE | PHE | PHE | PHE | PHE | PHE | PHE | PHE | PHE | PHE | PHE |
| 71 | TYR | PHE | PHE | TYR | TYR | PHE | TYR | PHE | TYR | ALA | ALA |
| 73 | LEU | LEU | LEU | LEU | LEU | LEU | LEU | LEU | LEU | LEU | LEU |
| 75 | ILE | ILE | ILE | ILE | ILE | ILE | ILE | ILE | ILE | ILE | ILE |
| 78 | MET | VAL | VAL | MET | LEU | VAL | LEU | VAL | LEU | LEU | LEU |
| 82 | ASP | ASP | ASP | ASP | ASP | ASP | ASP | ASP | ASP | ASP | ASP |
| 83 | | | | | | | | | PHE | | |
| 84 | ALA | ALA | | ALA | ALA | | ALA | | | ALA | THR |
| 86 | TYR | TYR | TYR | TYR | TYR | TYR | TYR | TYR | TYR | TYR | TYR |
| 88 | CYS | CYS | CYS | CYS | CYS | CYS | CYS | CYS | CYS | CYS | CYS |
| 102 | THR | THR | THR | THR | THR | THR | THR | THR | THR | THR | THR |
| 104 | LEU | LEU | LEU | LEU | LEU | LEU | LEU | LEU | LEU | LEU | VAL |
| 106 | LEU | ILE | ILE | ILE | | | ILE | ILE | | VAL | VAL |

Those in the $V_H$ domain are listed in Table 6 below.

TABLE 6

Inward-Pointing, Buried Framework Residues in the $V_H$ of Fabs of Known Three-Dimensional Structure

| | Antibody | | | | | | | | | | |
|---|---|---|---|---|---|---|---|---|---|---|---|
| Position | J539 | McPC603 | HyHEL-10 | HyHEL-5 | R19.9 | 4-4-20 | 36-71 | B13I2 | 01.3 | NEWM | KOL |
| 2 | VAL | VAL | VAL | | | | VAL | VAL | VAL | | VAL |
| 3 | LEU | LEU | LEU | LEU | LEU | LEU | LEU | LEU | LEU | LEU | LEU |
| 6 | GLU | GLU | GLU | GLN | GLU | GLU | GLN | GLU | GLU | GLN | GLN |
| 9 | | | PRO | | | | | | | | |
| 12 | VAL | VAL | VAL | MET | VAL | VAL | VAL | VAL | VAL | VAL | VAL |
| 18 | LEU | LEU | LEU | VAL | VAL | MET | VAL | LEU | LEU | LEU | LEU |
| 20 | LEU | LEU | LEU | ILE | MET | LEU | MET | LEU | ILE | LEU | LEU |
| 22 | CYS | CYS | CYS | CYS | CYS | CYS | CYS | CYS | CYS | CYS | CYS |
| 24 | ALA | THR | VAL | ALA | ALA | ALA | ALA | ALA | VAL | VAL | SER |
| 27 | PHE | PHE | ASP | TYR | TYR | PHE | TYR | PHE | PHE | THR | PHE |
| 29 | PHE | PHE | ILE | PHE | PHE | PHE | PHE | PHE | LEU | PHE | PHE |
| 36 | TRP | TRP | TRP | TRP | TRP | TRP | TRP | TRP | TRP | TRP | TRP |
| 38 | ARG | ARG | ARG | LYS | LYS | ARG | LYS | ARG | ARG | ARG | ARG |
| 40 | | | | | | SER | | | | | |
| 46 | | GLU | GLU | GLU | | | | | | | |
| 48 | ILE | ILE | MET | ILE | ILE | VAL | ILE | VAL | LEU | ILE | VAL |
| 49 | | ALA | | | | ALA | | ALA | | | ALA |
| 66 | LYS | ARG | ARG | LYS | | | | ARG | ARG | ARG | ARG |
| 67 | PHE | PHE | ILE | ALA | THR | PHE | THR | PHE | LEU | VAL | PHE |
| 69 | ILE | VAL | ILE | PHE | LEU | ILE | LEU | ILE | ILE | MET | ILE |
| 71 | ARG | ARG | ARG | ALA | VAL | ARG | VAL | ARG | LYS | VAL | ARG |
| 76 | | | | | | SER | | | | | |
| 78 | LEU | LEU | TYR | ALA | ALA | VAL | ALA | LEU | VAL | PHE | LEU |
| 80 | LEU | LEU | LEU | MET | MET | LEU | MET | LEU | LEU | LEU | LEU |

TABLE 6-continued

Inward-Pointing, Buried Framework Residues in the $V_H$ of Fabs of Known Three-Dimensional Structure

| | Antibody | | | | | | | | | | |
|---|---|---|---|---|---|---|---|---|---|---|---|
| Position | J539 | McPC603 | HyHEL-10 | HyHEL-5 | R19.9 | 4-4-20 | 36-71 | B13I2 | 01.3 | NEWM | KOL |
| 82 | MET | MET | LEU | LEU | LEU | MET | LEU | MET | MET | LEU | MET |
| 82C | VAL | LEU | VAL | LEU | LEU | LEU | LEU | LEU | LEU | VAL | LEU |
| 86 | ASP | ASP | ASP | ASP | ASP | ASP | ASP | ASP | ASP | ASP | ASP |
| 88 | ALA | ALA | ALA | | ALA | | ALA | ALA | ALA | ALA | |
| 90 | TYR | TYR | TYR | TYR | TYR | TYR | TYR | TYR | TYR | TYR | TYR |
| 92 | CYS | CYS | CYS | CYS | CYS | CYS | CYS | CYS | CYS | CYS | CYS |
| 94 | ARG | ARG | ASN | HIS | ARG | | ARG | ARG | ARG | ARG | ARG |
| 107 | THR | THR | | THR | THR | THR | THR | THR | THR | SER | THR |
| 109 | VAL | VAL | VAL | LEU | LEU | VAL | LEU | LEU | LEU | VAL | VAL |
| 111 | VAL | VAL | VAL | VAL | VAL | VAL | VAL | VAL | VAL | VAL | VAL |

From the above, it may be seen that (1) There are many FR amino acids that either contact the CDRs or the opposite domain, or are found in the main interior.

(2) These FR amino acids, which could influence the structure of the combining site, and thus the antigen-binding characteristics of an antibody, are different from antibody to antibody.

It is obvious from these results that no one structure can serve as the perfect and sole basis of all "animatlization", or in the present example "humanization", protocols. In fact, to "humanize" the 9 murine antibodies shown in Table 1 above by CDR-grafting with a view to preserving their ligand-binding properties, the FR amino acids listed in Table 2 to 6 above would have to be retained.

A search through the tables of immunoglobulin sequences (Kabat et al., "Sequences of Proteins of Immunological Interest", 5th Ed. U.S. Dept. of Health and Human Service, NIH Publication No.91-3242 (1991), shows that human variable domain sequences are known that already have most of the FR amino acids that need to be preserved as shown in Table 7 below.

TABLE 7

Human Antibodies that are Most Similar in Sequence to Murine Antibodies of Known Three-Dimensional Structure

| ANTIBODY | DOMAIN | MOST SIMILAR HUMAN SEQUENCE |
|---|---|---|
| HyHEL-10 | VH | 58P2'CL (77/112) |
| | VH FRAMEWORK | 15P1'CL, ML1'CL (62/87) |
| | VH IMPT | 58P2'CL, Ab26'CL, C6B2'CL (28/38) |
| | VL | IARC/BL41'CL (73/107) |
| | VL FRAMEWORK | IARC/BL41'CL (59/80) |
| | VL IMPT | IARC/BL41'CL (30/37) |
| HyHEL-5 | VH | ND'CL (74/116) |
| | VH FRAMEWORK | 783c'CL, X17117'CL (63/87) |
| | VH IMPT | 21/28'CL, 51P1'CL, 783c'CL, 8E10'CL, AND KAS, NEI'CL, X17115'CL (25/37) |
| | VL | HF2-1/17'CL, KAS (65/105) |
| | VL FRAMEWORK | HF2-1/17'CL (57/80) |
| | VL IMPT | BI, DEN, HF2-1/17'CL, KUE, REI, WALKER'CL, WIL(−) (27/36) |
| RI9.9 | VH | 21/28'CL (73/119) |
| | VH FRAMEWORK | 21/28'CL, 51P1'CL, AND, LS2'CL, NEI'CL (60/87) |
| | VH IMPT | 21/28'CL, 8E10'CL, LS2'CL (28/38) |
| | VL | WALKER'CL (78/107) |
| | VL FRAMEWORK | RZ (62/80) |
| | VL IMPT | REI, WALKER'CL (33/36) |
| 4-4-20 | VH | 30P1'CL (77/116) |
| | VH FRAMEWORK | 2P1'CL, 3D6'CL (65/87) |
| | VH IMPT | 4B4'CL, M26'CL (36/41) |
| | VL | RPM1-6410'CL (91/112) |
| | VL FRAMEWORK | GM-607-'CL (68/80) |
| | VL IMPT | CUM, FR, NIM (33/38) |
| J539 | VH | 30P1'CL, Vh38C1.10'CL (81/118) |
| | VH FRAMEWORK | 18/2'CL, 30P1'CL, M43 (71/87) |
| | VH IMPT | 38P1'CL, 561'CL, M72, M74 (36/40) |
| | VL | PA (62/105) |
| | VL FRAMEWORK | LEN, WEA (53180) |
| | VL IMPT | BI, DEN, KUE, REI, WALKER'CL, WIL(−) (26/35) |

TABLE 7-continued

Human Antibodies that are Most Similar in
Sequence to Murine Antibodies of Known
Three-Dimensional Structure

| ANTIBODY | DOMAIN | MOST SIMILAR HUMAN SEQUENCE |
|---|---|---|
| McPC603 | VH | M72 (81/120) |
| | VH FRAMEWORK | 4G12'CL, Ab18'cI, M72, M74, RF-SJ2'CL (70/87) |
| | VH IMPT | 56P1'CL, M72, M74, RF-SJ2'CL (35/42) |
| | VL | FK-001'CL, LEN (91/113) |
| | VL FRAMEWORK | LEN (70/80) |
| | VL IMPT | LEN (38/42) |
| 36-71 | VH | 21/28'CL (74/119) |
| | VH FRAMEWORK | 21/28'CL, 5101'CL, 783c'CL, AND'CL, NEI'CL, X17115'CL, (61/87) |
| | VH IMPT | 21/28'CL, 8E10'CL (28/38) |
| | VL | AG (76/105) |
| | VL FRAMEWORK | RZ (63/80) |
| | VL IMPT | REI, RZ, WALKER'CL (34/37) |
| B13I2 | VH | 56P1'CL(83/119) |
| | VH FRAMEWORK | 4B4'CL,4G12'CL, M26'CL, M72, RF-SJ2'CL, Vh38C1.10'CL |
| | VH IMPT | 56P1'CL, M72, M74, RF-SJ2'CL (37/39) |
| | VL | RPM1-6410'CL (86/112) |
| | VL FRAMEWORK | GM-607-'CL (69/80) |
| | VL IMPT | CUM, NIM (36/39) |
| 01.3 | VH | C6B2'CL (72/116) |
| | VH FRAMEWORK | C6B2'CL (62/87) |
| | VH IMPT | M60'CL (32/37) |
| | VL | BR (75/107) |
| | VL FRAMEWORK | HF2-1/17'CL (64/80) |
| | VL IMPT | 3D6'CL, BI, DEN, DU, KUE, PA, REI, WALKER'CL, WIL(-) (32/ ) |

These human sequences are not necessarily those which are most similar to the murine antibodies, overall or in the framework regions only, but rather, those that possess the largest number of important amino acids in common, the latter sequences being included in Table 7 above.

The number of murine amino acids that still need to be retained in order to have all the important FR amino acids in the "humanized" or analogue versions of the murine antibodies, as shown in Table 7 above, ranges from 21 (for HyHEL-5:12 in $V_H$ and 9 in $V_L$) to 5 (for B1312:2 in $V_H$ and 3 in $V_L$). These are not very many amino acids, considering that the resulting "humanized" or analogue molecules will probably retain most or all their ligand-binding characteristics. It is possible that there exist other human sequences that are even more similar to these murine domains that are not included in the compilation of Kabat, et al. (1991), supra. When more sequences become available these may also be incorporated to improve the pool of basic data available.

b) Choosing the Best Human Framework to Use in the "Humanization" of an Antibody When its Structure is Not Known.

In the absence of a three-dimensional structure, the identification of the FR amino acids that are crucial to maintain the combining site structure is not easily done. Nevertheless, some proposals may be made from the data shown in Tables 2 to 6 above that have been collected in Tables 8 and 9 below for the $V_L$ and $V_H$ domains.

TABLE 8

Framework Residues in $V_L$ That Probably Need to Be Preserved
in Order to Reproduce the Ligand Properties of the Original Antibody

CDR1

| | | | | | |
|---|---|---|---|---|---|
| J539 | EI.L.Q .......T.A. ......V.I.C. ......sass --------svsslh | | | | WYQQ....SP.PWIY |
| McPC603 | DIVMTQ .......L.V. ......V.M.C........kssqsllusgnqknfla - | | | | WYQQ....PP.LLIY |
| HyHEL-10 | DIVL>Q .......L.V. ......V.L.C. ......rasq -------signnlh | | | | WYQQ....SP.LLIK |
| HyHEL-5 | DIVL.Q .......M.A. ......V.M.C. ......sass --------svnymy | | | | WYQQ....SP.LLIK |
| RI9.9 | .IQMTQ .......L.A. ......V.I.C. ......rasq -------disnyln | | | | WYQQ....T.KLLVY |
| 4-4-20 | DVVMTQ .......L.V. ......A.I.C. ......rasq --slvhsqqntylr | | | | WYLQ.....PKVLIY |
| 36-71 | DIQM.Q .......L.A. ......V.I.C. ......rasq -------dinnfln | | | | WYQQ.....I.LLIY |
| B13I2 | .VLM.QT ......L.V. ......A.I.S.C. ....rasq --tillsdgdtyle | | | | WYLQ....SP.LLIY |
| 01.3 | DI.M.Q. ......L.A. ......V.I.C. ......rasq -------nihnyla | | | | WYQQ....SP.LLVY |

TABLE 8-continued

Framework Residues in V_L That Probably Need to Be Preserved
in Order to Reproduce the Ligand Properties of the Original Antibody

|  | CDR2 |  |  | CDR3 |  |
|---|---|---|---|---|---|
| J539 | eisklas | ......V.RF | ......Y.L.I..M | ....D.A.YYC--qqwtyplit | F...T.L.L. |
| McPC603 | gastres | ......V.DRF | .....S.TDF.L.I..V | D.A.YYC--qndhsyplt | F.A.T.L.I. |
| HyHEL-10 | yasqsis | ......I...RF | .....T.F.L.I..V...D | ..MYFC----qqsnswpyt | F...T.L.I. |
| HyHEL-5 | disklas | ......V..RF | .....Y.L.I..M | ....D.A.YYC--qqwgr-npt | F...T.L.I. |
| R19.9 | ytsrlhs | ......V..RF | .....DY.L.I..L...D | .ATY.C--qqgsattprt | F...T.L... |
| 4-4-20 | kvsnrfs | ......F.DRF | .....T.F.L.I..V...D | Y.C.-----sqsthvpwt | F...T.L... |
| 36-71 | ftsrsqs | ......V..RF | .....TDY.L.I..L..D | .A.YFC--qqgnalprt | F...T.L... |
| B13I2 | kvsnrfs | ......V.DRF | .....T.F.L.I..V..D | ..VYYC--fqgshvppt | F...T.L.I. |
| D1.3 | ytttlad | ......V..RF | .....S.T.Y.L.I..L | DF..YYC--qhfwstprt | F...T.L... |

TABLE 9

Framework Residues in V_H That Probably Need to Be
Preserved in Order to Reproduce
the Ligand Properties of the Original Antibody

| J539 | .V.L.E......V......L.L.C.A.. FDF. kywms WVKQ.....LEWI |
|---|---|
| McPC603 | .V.L.E......V......L.L.C.T.. FTF. dfyme WVRQ.....RLEWIA |
| HyHEL-10 | .V.L.E..P...V......L.L.C.V.. D.IT sdyws WIRK.....N. LEYM |
| HyHEL-5 | ...L.Q......M......V.I.C.A.. YTF. dywie WVKQR....LEWI |
| R19.9 | .V.L.E......V......V.M.C.A.. YTFT syvgn WVKQ...Q..E.WI |
| 4-4-20 | ...L.E......V......M.L.C.A.. FTFS dywmn WVRQS....LEWVA |
| 36-71 | EV.L.Q......V......V.M.C.A.. YTF. sngin WVKQ.....LEWI |
| B12I2 | .V.L.E......V......L.L.C.A.. FTP. rcams WVRQ...K.L.WVA |
| D1.3 | .V.L.E......V......L.I.C.V.. F.L. gygvn WRQ.....LEWL. |

|  | CDR2 |
|---|---|
| J539 | eihp--dsgtinhtpslkd KF.I.R.N.....L. L. M.. V... D. A. YYCAR |
| McPC603 | asrnkgnkytteysasvkg RFIV.R.T.....L. L. M.. L... D. A. YYCAR |
| HyHEL-10 | yvs---ysgstyynpslks RI.I.R.....Y. L.. V... D. A. YYC.N |
| HyHEL-5 | eilp--gsgstnyherfkg KA.F.A.....A. M. L.. L... D. ..YVCLH |
| R19.9 | yinp--gkgylsynekfkg .TTL.V.....A. M. L.. L... D. A. YFC.R |
| 4-4-20 | qirnkpynyetyysdsvkg RFTI.R. D.. S. V. L. M.. L... D. ..YYCT. |
| 36-71 | ynnp--gngyiaynekfkg .T.L.V.....A. M. L.. L... D. A. YFCAR |
| H13I2 | giss--ggsytfypdtykg RF.I.R.....L. L. M.. L... D. A. YYCTR |
| D1.3 | miw---gdgntdynsalks RL.I.K.....V. L. M.. L... D. A. YYCAR |

|  | CDR3 |
|---|---|
| J539 | lhyygyn------ay W. Q. T. V. V. . |
| McPC603 | nyygstwyf----dv W. ...T. V. V. . |
| Hy-HEL-10 | wdg----------dy W. ... V. V. . |
| Hy-HEL-5 | gnydf--------dg W. ..T. L. V. . |

TABLE 9-continued

Framework Residues in $V_H$ That Probably Need to Be Preserved in Order to Reproduce the Ligand Properties of the Original Antibody

| | |
|---|---|
| R19.9 | sfyggadlavyyfds W. . .T. L. V. . |
| 4-4-20 | syygm--------dy W. . .T. V. V. . |

From Tables 8 and 9 above, it may be seen that many of the important FR amino acids flank the CDRs. Among these flanking positions are most of the FR amino acids that are involved in the contact with the opposite domain as shown in Table 4 above, and many of those which are in contact with the CDRs as shown in Tables 2 and 3 above. Moreover, almost all of the FR amino acids that have been observed to participate in the binding to antigen (Amit, A. G., et al., Science 233:747–753 (1986); Sheriff, et al., P.N.A.S. (USA) 82:1104–1107 (1987); Padlan, E. A., et al., P.N.A.S. (USA) 86:5938–5942 (1989); Tulip, et al., Cold Spring Harbor Symp. Quant. Biol. 54:257–263 (1989); Bentley, et al., Nature (London) 348: 254–257 (1990)), are in these flanking regions. Thus, during "animalization" or "humanization" or formation of the analogue peptides, not just the CDRs are retained, but also some of the residues immediately adjacent to the CDRs. This provides a better chance of retaining more of the ligand-binding properties of the original antibody. The likelihood of retaining the antigen binding properties of the original antibody is even greater if the first few amino acids in the $NH_2$-termini of both chains are also retained, since some of them are found to be in contact with CDRs as shown in Tables 2 and 3 above. Further, Tables 8 and 9 above also show many other framework positions that are deemed structurally important in all the cases examined here. The xenogeneic residues at those positions should probably be retained as well.

Alternatively, it may possible to reduce immunogenicity, while preserving antigen-binding properties, by simply replacing those exposed residues in the framework regions which differ from those usually found in human antibodies (Padlan, E. A. (1991), supra). This would "humanize" the surface of the xenogeneic antibody while retaining the interior and contacting residues which influence its antigen-binding characteristics. The judicious replacement of exterior residues should have little, or no, effect on the interior of the domains, or on the interdomain contacts. For example, the solvent accessibility patterns of the Fvs of J539, a murine IgA (k) and of KOL, a human IgG1 (I) have been found to be very similar (Padlan, E. A. (1991), supra).

At present, more than 35 different Fab structures have been elucidated by X-ray diffraction analysis, although atomic coordinates for only 11 are currently in the Protein Data Bank as shown in Table 1 above. Most of the available structures have been analyzed to only medium resolution, some having been refined to only a limited extent. Eventually, atomic coordinates for more and better-refined structures will become available, so that the "important" FRs will be more easily assessed. This will improve the theoretical predictive record of the present method for determining the best mode for the analogue peptides.

As already indicated above, the specificity of an antibody depends on the CDR structures and sometimes, on some neighboring residues as well. These structures, in turn, depend on contacts with framework amino acids and on the interaction of the VL and VH domains. Thus, to ensure the retention of binding affinity, not only the CDR residues must be preserved, but also those FRs that contact either the CDR's or the opposite domain, as well as all buried residues, which give shape to the variable domains.

This design of the humanized versions of murine antibodies is reached in stages as follows.

1-Choice of a xenogeneic model of known structure.
2-Choice of the target species FR.
3-Identification of xenogeneic/target species differences.
4-Identification of important xenogeneic amino acids.

(1) Choice of a Xenogeneic Model of Known Structure

The $V_H$ and $V_L$ domains of an antibody of desired specificity are classified according to Kabat et al. (1991), supra. Then, an antibody of the same species may be chosen, whose structure has been determined, and whose variable regions belong to the same classes and subclasses. Modeling the xenogeneic antibody in question to such structure ensures maximal chance for success. This, however, is not absolutely necessary since the relative positions of the important amino acids do not vary considerably even in variable regions of different classes. Thus, with less than a perfect match this method may still be applied to design the analogues of this invention. Once the xenogeneic model is chosen, it may be applied to identify the locations of important residues in the xenogeneic antibody to be animalized (humanized). Tables 2, 3, 4, 5, 6, 8 and 9 indicate the positions of the important amino acids in several antibodies whose structures have been determined to a high resolution level.

(2) Choice of the Target Species FR

The target species framework should, ideally, be a consensus framework. That is, one that has a maximum number of amino acids in common with all human frameworks of the same class. This is important, because, the goal of humanization is to avoid an immunological response against the engineered analogue peptide.

The target species framework that is chosen is that which shares the greatest number of important amino acids with the original xenogeneic antibody. Thus, in choosing the target species (human) FR, the similarity between the important amino acids is more important that the overall similarity.

In practice, the sequences of the xenogeneic variable chains are aligned with the consensus sequences from all variable region classes of the target species and the number of differences in the amino acids that must be retained from the xenogeneic species are scored. The human consensus sequence(s) that score(s) the lowest number of differences is (are) then chosen. These are the best analogue peptide candidates. Others with low numbers that are higher than the above may also be suitable, and are placed in a reserve pool, and so forth. If there are too many differences in the chosen framework (e.g., more than 16), then the same alignment procedure using all tabulated human sequences may be repeated in order to find a specific human framework whose similarity with the xenogeneic sequence is maximized at the positions of the important amino acids. Thus, most preferably, the target species FR should be a consensus sequence. Next preferable would be a framework of a common target species (human) antibody, and finally, the framework of any target species (human) antibody.

(3) Identification of Xenogeneic Target Species Differences

The xenogeneic sequences are then aligned with the target species sequences and the positions of all amino acids that differ in the murine and in the human frameworks are tabulated. Such a table contains the maximum number of amino acids that can be changed toward the full "animalization" ("humanization") of the xenogeneic antibody (see, Tables 31 and 32 below). If all those changes were to be made, a so-called CDR-grafted antibody would be obtained. That is, only the original CDRs would be retained from the murine antibody. In some cases, possibly, such CDR-grafted antibody may maintain the original binding affinity. In most instances, however, the affinity of a CDR-grafted antibody would be considerably less than that of the original xenogeneic antibody. In order to maximize the chances for conserving the original affinity, the identities of all important amino acids must be preserved.

(4) Identification of Important Xenogeneic Amino Acids

If the outlined approach to animalization (humanizing) an antibody is followed strictly, the amino acids that are correspondingly important in the model xenogeneic antibody chosen in step 1 are retained. In a more preferred approach, however, the amino acids that have been shown to occupy important positions in other antibodies of the same species or of the target species may also be retained and are therefore taken out from the group of candidates to be mutated. This preferred approach may be particularly appropriate when there is a chance that the amino acids in question could make contacts with the CDRs or with the opposite chains. Once the important xenogeneic amino acids are identified, the DNA sequence may be mutagenized to change all other amino acids, which for the most part occupy exposed positions.

The present method is exemplified for a murine antibody humanized with the intent of diminishing or avoiding a HAMA response upon its administration to humans. Murine and human antibodies, whose three-dimensional structures have been deduced to a high degree of resolution, were utilized as guidance in the choice of the amino acids to be substituted in order to humanize the particular murine antibody utilized. The method, however, may be applied more generally to transform antibodies from one species into a less immunogenic form to be administered to a second species, provided that adequate three-dimensional models are available for antibodies from those species. Information on other murine antibodies from a Data Bank was used in the exemplary disclosure provided below to modify the BrE-3 and anti-KC-4 murine-human chimeric antibodies with human amino acids. Similarly, antibodies of other species besides murine may also be utilized, their CDRs and other amino acids preserved and those amino acids not considered "important" replaced with human amino acids. Similarly, the above approach may be applied to the preparation of "animalized" antibodies for any animal species. This may be attained by substituting amino acids of the antibody target species into an antibody of another species in accordance with this invention.

Various peptide structures, such as CDRs, and analogue antibodies, Fab, Fab', (Fab')2, and variable fragments having a desired specificity, may be constructed and optionally bridged via a linker. In addition, one or more of the peptides may be attached to one or more effector agent(s) or bridged via a linker. Multiple antibody, variable regions, Fab, Fab', (Fab')2, CDRs and the like, and combinations thereof, may also be constructed and bridged via linkers or attached to one or more effector agents such as are described below.

The cDNAs encoding the analogue variable regions of an antibody of a desired specificity may be cloned into a vector, optionally containing sequences encoding constant regions or fragments thereof, enzymes, neuropeptides, other peptide transmitters, toxins, hormones, operative conjugation regions, cytokines, lymphokines and the like, optionally under the same promoter. Although this is the cloning strategy utilized in the exemplary disclosure of this invention, other methods known in the art may also be utilized such as co-expression and the like. In the exemplary disclosure provided herein, the anti-BrE-3 and anti-KC-4 murine-human chimeric antibodies specifically binding to human mammary mucin and carcinoma cells was constructed by joining the DNAs of the anti-BrE-3 or anti-KC-4 murine variable domain to a human constant domain (an effector agent) cloned into a hybrid vector, and the product expressed by transfecting the vector into myeloma cells. The variable regions of the chimeric antibody were modified at the DNA level to obtain an analogue or "humanized" chimeric polypeptide. The modifications to the variable regions of the peptides may either be conducted by PCR amplification with primers that are custom tailored to produce the desired mutations, or by gene synthesis.

The analogue "humanized" peptides prepared and exemplified below comprise the "humanized" variable regions of the anti-BrE-3 or anti-KC-4 murine antibodies (U.S. Pat. Nos. 5,075,219 and 4,708,930) and the kappa and gamma 1 constant region of a human antibody. These humanized antibodies were characterized by their molecular weights and binding specificities, and shown to compete well with or better than the respective parent murine and chimeric antibodies for the antigen. The analogue "humanized" peptides were shown to bind weakly to normal breast, lung, colon and endometrium, and strongly to carcinoma tissue sections by the ABC immunoperoxidase method. The portions of the CDR and FR regions of the non-modified peptides (murine Fv regions) and effector agents (human Fc regions) were shown in both cases to be substantially identical to those of the non-human and human antibodies from which they were obtained. The analogue peptides and hybrid derivatives of this invention lacking any non-human constant region sequences possess less foreign antigenic epitopes than the whole xenogeneic or chimeric antibodies from which they are derived. Accordingly, they are expected to elicit a less complex immunogenic response in animals such as humans than the corresponding non-human whole antibodies or even than the chimeric antibodies. However, to what extent a portion of the non-human FR amino acids may be replaced without altering the binding characteristics of the CDRs could not have been predicted prior to this invention because of the substantial conformational alterations in the interior regions that affect the binding of the CDRs to the antigen that may occur upon modification of amino acid sequences.

Thus, the substantially pure, isolated analogue peptide of the invention specifically and selectively binds to an antigen present on the surface or in the cytoplasm of a carcinoma cell or that is released by the cell. The polypeptide consists essentially of at least one CDR or variable region of the light or heavy chains of an antibody of a first species having affinity and specificity for an antigen found on the surface or the cytoplasm of a carcinoma cell of another species or that is released by the cell, wherein when the framework regions (FRs) are present, about 1 to at least 46 amino acids in the FRs are substituted per chain with amino acids, e.g., present in equivalent positions in antibodies of other species or similar amino acids, or fragments thereof comprising 1 to 3 CDRs per chain, or 1 to 3 CDRs per chain plus flanking regions thereof, each of about 1 to 10 or more amino acids, alone or plus an N-terminal fragment of about 1 to 10 or more amino acids, combinations thereof wherein each analogue peptide is operatively linked to at least one other analogue peptide, combinations thereof and mixtures thereof.

A single unit of the analogue peptide of the invention may be as short as the shortest CDR and as long as the longest combination of variable regions, antibodies, and the like, including non-peptide polymers of up to about 106 molecular weight, and in some instances even larger. When several units are linked or other combinations provided, the size of the analogue peptide increases accordingly. The smaller molecular weight analogue peptides are particularly suited for greater penetration of cells, the brain-blood barrier, and tumors, among others, and have a shorter half life, whereas the higher molecular weight polypeptides are suited for either in vitro or in vivo applications such as therapy, imaging and diagnosis. The latter are generally cleared from the body over a longer period of time.

The analogue peptide of the invention may contain amino acid sequences derived from light and/or heavy chains of antibodies of a first or xenogeneic species raised against a variety of antigens and/or epitopes. For example, the murine antibodies disclosed in the examples were raised against human mammary fat globule mucin (BrE-3) and the "KC-4" antigen in human carcinoma cells (KC-4). Other antigens comprising a variety of epitopes may also be utilized to generate the xenogeneic antibodies as long as the antibody contributing the variable region displays low affinity and specificity for normal cells and higher affinity and specificity for human carcinomas that will permit their specific binding to carcinoma cells, preferably, in a variety of tissues. Similarly, the antibodies may be raised in animals of different xenogeneic species. The antibodies from which the polypeptide of the invention is derived may be a murine, rat, goat, birds including poultry, rabbit, guinea pig, equine, bovine, and primate including human and simian, antibodies, among others. The preparation of the antibody and fragments thereof encompassed by the invention is similar, whether the origin of the antibody is human or non-human. The original variable region mRNA may be obtained from cells of any desired xenogeneic species and the remainder of the work-up is similar, utilizing a model antibody of the same xenogeneic species and substituting amino acids from the target species.

The humanization procedure described here is designed to minimize potential losses in antigen binding affinity that may result from the introduced amino acids. In the case of the BrE-3 antibody exemplified below, eight amino acid changes were made in the variable region of the light chain and in the variable region of the heavy chain. In the case of the anti-KC-4 antibody exemplified below, seven amino acid changes were introduced in the variable region of the light chain and twelve amino acid changes were made in the variable region of the heavy chain. Furthermore, to minimize the immunlogical response to the humanized antibody, target human amino acid sequences were used that comprise the consensus sequences of all appropriate human variable regions. Nevertheless, neither the exemplified amino acid changes nor the exemplified human target sequences are the only choices encompassed by this invention. Many other individual amino acid changes and permutations thereof may be made without the expectation of significantly affecting either the affinity of the resulting antibody or its human immunogenicity, as taught herein.

The following Tables 10 and 11 indicate other possible amino acid changes for the variable regions of the BrE-3 and KC-4 sequences of the invention. The amino acid positions (or numbers) are as conventionally accepted (Kabat et al., 1991, supra). The most preferred changes are indicated under the heading "Most Preferred Analogue". For antibodies other than the BrE-3 and anti-KC-4 antibodies, the amino acids shown in the BrE-3 and KC-4 columns become also part of the group of most preferred choices. Amino acid changes that are not part of the most preferred group but that are still part of this invention are indicated in the next column under the heading "Preferred Analogue". In some instances, the "Preferred Analogue" choices become too numerous and the least acceptable choices are provided instead for that position. Clearly, all amino acids other than those listed under "Not Preferred Analogue" may be substituted at that position.

TABLE 10

Alternative Amino Acids for $V_L$ Chain

| VL | BrE3 | KC4 | Most Preferred Analogue | Preferred Analogue | Not Preferred Analogue |
|---|---|---|---|---|---|
| FR1 | | | | | |
| 1 | D | D | | | WIPLMCRT |
| 2 | V | V | | WKCRH | |
| 3 | V | L | L(V) | | YC |
| 4 | M | M | LVI | PTQ | |
| 5 | T | T | | | |
| 6 | Q | Q | | | |
| 7 | T | T | IADS | | WYMCGH |
| 8 | P | P | AE | | WYFKCN |
| 9 | L | L | FP | | WYMH |
| 10 | S | S | T | | HDQ |
| 11 | L | L | NV | | WYCRGH |
| 12 | P | P | S | | WIKH |
| 13 | V | V | | | YKCRHN |
| 14 | S | T | T(S) | | WMCE |
| 15 | L | P | PFIL | | WYCGHDNEQ |
| 16 | G | G | | | |
| 17 | D | E | TEQ(D) | | WIYFPMCR |
| 18 | Q | P | PS(Q) | | WYFCAHDN |
| 19 | A | A | V | | WPKMCRTHNQ |
| 20 | S | S | | | WPLCHD |
| 21 | I | I | | | WPKCGDEQ |
| 22 | S | S | | | WVMCHE |
| 23 | C | C | | | |
| FR2 | | | | | |
| 35 | W | W | | | |
| 36 | F | F | YL(F) | IVHN | |
| 37 | L | L | Q | WLVKRTHDE | |
| 38 | Q | Q | | | IFMCATSDN |
| 39 | K | K | R | | WIPMCA |
| 40 | S | P | P(S) | FLKARTGQ | |
| 41 | G | G | | | IYFPMCT |
| 42 | Q | Q | | | WYVCD |
| 43 | S | S | P | | WYFKMHDNEQ |
| 44 | P | P | | | WYKCRGHDQ |
| 45 | K | Q | EQR(K) | | YPCGHD |
| 46 | L | L | RV | | KCD |
| 47 | L | L | V | WILMTSN | |
| 48 | I | I | | FPLVMTS | |
| 49 | Y | Y | S | | PLVMA |
| FR3 | | | | | |
| 57 | G | G | | WVTSGDNEQ | |
| 58 | V | V | | IYFLVMATQ | |
| 59 | P | P | S | | |
| 60 | D | D | N | | WFMCR |
| 61 | R | R | T | | |
| 62 | F | F | | | |
| 63 | S | S | T | IYPLKARSG | |

TABLE 10-continued

Alternative Amino Acids for $V_L$ Chain

| VL | BrE3 | KC4 | Most Preferred Analogue | Preferred Analogue | Not Preferred Analogue |
|---|---|---|---|---|---|
| 64 | G | G | D | | |
| 65 | S | S | | | |
| 66 | G | G | | | YCHDQ |
| 67 | S | S | A | | VKMCRHN |
| 68 | E | G | GD(E) | VMCARSGQ | |
| 69 | T | T | | | WPMCE |
| 70 | D | D | | | WIFPMCR |
| 71 | F | F | | | WKMTEQ |
| 72 | T | T | | | WLMCGHNEQ |
| 73 | L | L | | | |
| 74 | K | K | NLRE | | WLMCHD |
| 75 | I | I | L | | |
| 76 | S | S | IT | | LVMC |
| 77 | R | R | S | | WYFLKCHQ |
| 78 | V | V | ALI | | WYFKCRHNE |
| 79 | E | E | KGQ | | WVKM |
| 80 | A | A | P | | WLKM |
| 81 | E | E | | ILVKMAGDNE | |
| 82 | D | D | | | |
| 83 | L | V | MV(L) | | WCRH |
| 84 | G | G | | LVARTSG | |
| 85 | V | I | IM(V) | | WFKCQ |
| 86 | Y | Y | | | |
| 87 | F | Y | YL(F) | IMSHE | |
| 88 | C | C | | | |
| FR4 | | | | | |
| 98 | F | F | | | |
| 99 | G | G | | | |
| 100 | G | G | ASQ | IPVKRTG | |
| 101 | G | G | | | |
| 102 | T | T | | | |
| 103 | K | K | NR | | IYMATGHDEQ |
| 104 | L | L | V | | LG |
| 105 | E | E | | | ILVTSGHNEQ |
| 106 | I | I | | | YLVKMRTD |
| 106a | | | | | PLVTI |
| 107 | K | K | R | | ILVMATSGNE |

TABLE 11

Alternative Amino Acids for $V_H$ Chain

| VL | BrE3 | KC4 | Most Preferred Analogue | Preferred Analogue | Not Preferred Analogue |
|---|---|---|---|---|---|
| FR1 | | | | | |
| 1 | E | E | Q | PVLKARGHDEQ | |
| 2 | V | V | M | | WYPKCRHV |
| 3 | K | Q | QR(K) | L | |
| 4 | L | M | | | WYKCRSN |
| 5 | E | V | VD(E) | | WYCG |
| 6 | E | E | QD | | WLYFMSH |
| 7 | S | S | T | | IMCRHD |
| 8 | G | G | E | | |
| 9 | G | G | | | WIYKCRNQ |
| 10 | G | G | DA | | WIYFMCH |
| 11 | L | L | VF | | WKCGHN |
| 12 | V | V | I | | WYPTHD |
| 13 | Q | Q | KE | | WYFCD |
| 14 | P | P | | | WIYMCRDQ |
| 15 | G | G | | | IYCHN |
| 16 | G | G | RSE | | WIYFMC |
| 17 | S | S | PA | | WIYCHDNE |
| 18 | M | | | | WYCD |
| 19 | K | R | R(K) | | WIYPCH |
| 20 | L | L | V | | WYFPKDNQ |
| 21 | S | S | | | WMH |
| 22 | C | C | | | |
| 23 | A | A | TSE | | WFLMCH |
| 24 | A | A | V | | WKMCRHNEQ |
| 25 | S | S | | | WIVMRHDEQ |
| 26 | G | G | | | |
| 27 | F | F | | | WPMCR |

TABLE 11-continued

Alternative Amino Acids for $V_H$ Chain

| VL | BrE3 | KC4 | Most Preferred Analogue | Preferred Analogue | Not Preferred Analogue |
|---|---|---|---|---|---|
| 28 | T | A | AINS(T) | | CHQ |
| 29 | F | F | | | WYKCRHDNEQ |
| 30 | S | S | | | WLMCDQ |
| FR2 | | | | | |
| 36 | W | W | | | |
| 37 | V | V | | WIFLVMATGQ | |
| 38 | R | R | | | YFS |
| 39 | Q | Q | | | FPVMCA |
| 40 | S | A | VA(S) | | WY |
| 41 | P | P | TS | PLVARTSHNEQ | |
| 42 | E | G | G(E) | | YPLKMCTHN |
| 43 | K | K | | | WIYLVCS |
| 44 | G | G | SR | | WIFMCH |
| 45 | L | L | | | |
| 46 | E | E | Q | | FPMCRTD |
| 47 | W | W | | | PMARNQ |
| 48 | V | V | STG | | YPKCARTHNQ |
| 49 | A | A | | | WFPKCRHNQ |
| FR3 | | | | | |
| 66 | R | R | | | WYLVMCATSDE |
| 67 | F | F | | | WYPKMHNEQ |
| 68 | T | T | IS | | WYPGE |
| 69 | I | I | | | WYKCHNQ |
| 70 | S | S | L | | WVMCHDEQ |
| 71 | R | R | | | WYFCHDQ |
| 72 | D | D | N | VKRTSGHDE | |
| 73 | D | N | N(D) | | WYFLC |
| 74 | S | S | A | FPLVTGDN | |
| 75 | K | K | EN | | NPCGD |
| 76 | S | N | NTRK(S) | | WFPLMCE |
| 77 | R | T | TNIVSM(R) | | WFC |
| 78 | V | L | LA(V) | | WKCRNE |
| 79 | Y | Y | FH | | WPG |
| 80 | L | L | | | WYLKCARGHEQ |
| 81 | Q | Q | E | | WYFPC |
| 82 | M | M | | | YPCTGHDEQ |
| 82a | I | N | SDN(I) | | WMQ |
| 82b | S | S | IR | | WYFPLMHQ |
| 82c | L | L | | PLVMAGE | |
| 83 | R | R | EKT | | WILCH |
| 84 | A | A | SPVTI | | WKCDEQ |
| 85 | E | E | D | WIYFPLMCRG | |
| 86 | D | D | | | |
| 87 | T | T | M | | WLVMCNE |
| 88 | G | A | A(G) | | |
| 89 | L | V | ITVM(L) | | WYPKGEQ |
| 90 | Y | Y | HF | | |
| 91 | Y | Y | | | WIPLVKMAGQ |
| 92 | C | C | | | |
| 93 | T | A | ASHAV(T) | | WIFR |
| 94 | G | R | R(G) | TSDQLAW | |
| FR4 | | | | | |
| 103 | W | W | A | | |
| 104 | G | G | YH | | |
| 105 | Q | Q | THR | | IYFLVMCDQ |
| 106 | G | G | | | |
| 107 | T | T | AQ | | |
| 108 | L | L | STGM | | WYCHDE |
| 109 | V | V | LT | IK | |
| 110 | T | T | SL | | |
| 111 | V | V | | | |
| 112 | S | S | T | | |
| 113 | A | S | S(A) | PLVATG | |

Similar tables may be constructed for any and all amino acid sequences for other xenogeneic antibodies as taught herein.

In one particularly preferred embodiment of the invention, the humanized anti-carcinoma analogue peptide comprises the amino acid sequence ID No. 67 to 73 of Table 47, the sequence ID No. 75 to 81 of Table 48, the sequence ID No. 95 to 102 of Table 55 and/or the sequence ID No. 103 to 108 of Table 56, and the sequences wherein about 1 to 46 or more amino acids in the FR are substituted per chain with amino acids such as those present in equivalent positions in human antibodies, or fragments thereof comprising 1 to 3 CDRs per chain or 1 to 3 CDRs per chain plus flanking regions thereof, each of about 1 to 10 or more amino acids, alone or plus an N-terminal fragment of about 1 to 10 or more amino acids, or combinations thereof wherein each analogue peptide is operatively linked to at least one other analogue peptide, and mixtures thereof.

The present analogue peptide is provided either as a naked peptide or in glycosylated form. When provided in glycosylated form, the analogue peptide may be operatively linked to a glycosyl residue(s) provided by the eukaryotic cell where it is expressed, or it may be cloned and expressed in a prokaryotic cell as the naked polypeptide and the glycosyl residue(s) added thereafter, for example by means of glycosyl transferases as is known in the art. Examples of glycosyl residue(s) that may be added to the analogue peptide of the invention are N-glycosylated and O-glycosylated residues, among others. The glycosyl residues added to the naked analogue peptide may have a molecular weight of about 20 to 50,000 daltons, and more preferably about 100 to 20,000 daltons or greater, depending on the size and molecular weight of the peptide to which they are attached. However, other types of polysaccharides and molecular weights may also be present. The glycosyl residues may also be attached to the naked analogue peptide of the invention by chemical means as is known in the art.

A single CDR is the smallest part of an antibody known to be capable of binding to an antigen. The sequences of the VL and VH CDRs of the BrE-3 exemplary analogue is shown in Tables 47 and 48 below. Thus, small peptides that have the sequence of a single CDR can bind antigen and are, therefore, suitable for imaging tumors in vivo. A CDR attached to an effector peptide may be synthesized chemically or recombinantly encoded in a DNA segment. Such small molecules have great tumor penetration and extremely rapid clearing properties when compared to larger antibody fragments. In some cases, it is more convenient to produce these small molecules by chemical synthesis, as is known in the art, rather than by fermentation. In many cases, these small peptides are completely non-immunogenic and an immune response, such as the HAMA response, is altogether avoided. Also preferred are 2 and 3 CDR units per chain operatively linked to one another by 1 to 10 or more amino acids and up to the entire inter-CDR segment length as positioned in the variable regions.

Heavy and light chain analogue variable regions may be obtained individually or in VH/VL pairs, or attached to an effector peptide such as a constant region(s) or portions thereof, a drug, an enzyme, a toxin, a whole antibody, or any other molecule or radioisotope. The fragments of the analogue variable regions may be synthesized chemically as is known in the art or from the DNA segments encoding the non-human variable regions. This may be attained by PCR amplification of the DNA with primers synthesized to contain the desired mutation(s) as is known in the art. Similarly, the fragments encoding analogue variable regions may be synthesized chemically or obtained by established cloning methods of restriction digestion, ligation, mutagenesis, and the like, as is known in the art.

There are advantages to using the different molecular variants of the analogue peptide depending on the specific applications for which they are intended, some of which are listed below.

(a) Smaller molecules penetrate target tissues more efficiently and are cleared from the body much more rapidly than larger molecules.

(b) Single chain molecules can be manipulated and synthesized more efficiently that multiple chain molecules.

(c) Many of these variants can be synthesized efficiently and inexpensively in bacteria, including the non-glycosylated analogues.

(d) Bi-functional or multifunctional molecules may carry polypeptide effectors, such as enzymes, toxins, radioisotopes, drugs, and other molecules, to a target tissue.

The following list encompasses exemplary analogue peptides of the invention engineered with molecules derived from antibodies or antibody fragments. These analogue peptides, among others, are suitable for the practice of this invention. A more extensive list of polypeptide constructs may be found in O'Kennedy, R., and Roben, P. (O'Kennedy, R., and Roben, P., "Antibody Engineering: an Overview", Essays Biochem. (England) 26:59–75 (1991)).

The analogue peptides and hybrid peptides of this invention encompass CDRs and/or analogue variable regions, monoclonal antibodies, antibody fragments such as Fab, Fab', (Fab')2, and fragments thereof, CDRs, constant regions, single or multiple-domain and catalytic fragments, bi-functional or multifunctional combinations thereof, enzymes, peptide hormones, molecules such as drugs and linkers, transmitters, and toxins, among others. These are suitable for imaging, therapy, and diagnostics.

Single-Chain Antigen-Binding Polypeptides

A method for constructing single chain antigen-binding polypeptides has been described by Bird et al. (Bird, R. E., et al., Science 242:243–246 (1988); Bird, R. E., et al., Science 244:409 (1989)). Single Chain Fv (scFv or sFv) are single chain analogue peptides containing both VL and VH with a linker such as a peptide connecting the two chains (VL-linker-VH). The engineering may be done at the DNA level, in which case knowledge of the sequence is required. These analogue peptides have the conformational stability, folding, and ligand-binding affinity of single-chain variable region immunoglobulin fragments and may be expressed in *E. coli*. (Pantoliano, M. V., et al., Biochem. (US) 30:10117–25 (1991)). The peptide linker binding the two chains may be of variable length, for example, about 2 to 50 amino acid residues, and more preferably about 12 to 25 residues, and may be expressed in E. coli. (Pantoliano, M. V., et al. (1991), supra). An analogue peptide such as an scFv may be expressed and prepared from *E. coli* and used for tumor targeting. The clearance profiles for scFv in some situations fragments are advantageous relative to those of normal antibodies, Fab, Fab' or (Fab')2 fragments. (Colcher, D., et al., J. Natl. Cancer Inst. 82:1191–7 (1990)). Another type of analogue peptide comprises a VH-linker-VL and may have about 230 to 260 amino acids. A synthetic gene using *E. coli* codons may be used for expression in *E. coli*. A leader peptide of about 20 amino acids, such that of Trp LE may be used to direct protein secretion into the periplasmic space or medium. If this leader peptide is not naturally cleaved, the sFv analogue peptide may be obtained by acid cleavage of the unique asp-pro peptide bond placed between the leader peptide and the sFv-encoding region (Houston, J. S., et al., "Protein Engineering of Antibody Binding Sites: Recovery of Specific Activity in an Anti-Digoxin Single-Chain Fv Analogue Produced in *E. coli.* ", PNAS (USA) 85 (16):5879–83 (1988)). The construction, binding properties, metabolism and tumor targeting of the single-chain Fv analogue peptides derived from monoclonal antibodies may be conducted as previously described (Milenic, D. E., et al., Cancer Res. (US) 51 (23 pt1):6363–71 (1991); Yokota, et al., "Rapid Tumor Penetration of a single-chain Fv and Comparison with Other Immunoglobulin Forms", Cancer Res. (US) 52(12):3402–8 (1992)). This type of analogue peptide provides extremely rapid tumor penetration and even distribution throughout tumor mass compared to IgG or Ig fragments Fab and F(ab')2.

Bifunctional $scF_v$-Fxn or Fxn-$scF_v$

An example of this type of analogue peptide is a VL-linker-VH with an effector peptide such as a hormone, enzyme, transmitter, and the like. These hybrid analogue peptides may be prepared as described by McCarney et. al. (McCarney, J. E. et al., "Biosynthetic Antibody Binding Sites: Development of a Single-Chain Fv Model Based on Antidinitrophenol IgA Myeloma MOPC 315", J. Protein Chem. (US) (6):669–83 (1991)). A bi-functional hybrid analogue peptide containing an Fc-binding fragment B of staph protein A amino terminal to a single-chain analogue Fv region of the present specificity is also encompassed and may be prepared as previously described. (Tai, M. S., et al., Biochem. 29 (35):8024–30 (1990)). In this example of a hybrid analogue peptide of this invention is a Staph. A fragment B (anti Fc)) -scFv polypeptide. The order is backward of normal cases. This FB-sFv may be encoded in a single synthetic gene and expressed as peptide in E. coli. This analogue peptide is a good example of a useful multifunctional targetable single-chain polypeptide. A hybrid analogue peptide also comprising antibodies to a human carcinoma receptor and angiogenin is also part of this invention. Angiogenin is a human homologue of pancreatic RNAse. This is an (Fab')2-like antibody-enzyme peptide effector. Another hybrid analogue peptide comprising a VH-CH1 heavy chain-RNAse may be expressed in a cell that secretes a chimeric light chain of the same antibody. A secreted antibody of similar structure was shown to cause the inhibition of growth and of protein synthesis of K562 cells that express the human transferrin receptor (Rybak, S. M., et al., "Humanization of Immunotoxins", PNAS 89:3165–3169 (1992)).

Bi-specific Antibodies

A monoclonal antibody or antibody fragment may be incorporated into a bi-specific analogue peptide as described, for example, by Greenman et al. (Greenman, J., et al., Mol. Immunol. (England) 28 (11):1243–54 (1991). In this example, a bi-specific F(ab')$_2$ comprising two (Fab'-(thioether-link)-Fab') was constructed. Bi-specific antibodies may also be obtained when two whole antibodies are attached. Another way to obtain bi-specific antibodies is by mixing chains from different antibodies or fragments thereof. In this manner the "left" branch of the bi-specific antibody has one function while the "right" branch has another.

Phage Display Libraries

The analogue peptides in accordance with this invention may be screened with a filamentous phage system. This system may also be used for expressing any genes of antibodies or fragments thereof as well as for screening for mutagenized antibody variants as described by Marks et al. (Marks, J. D., et al., "Molecular Evolution of Proteins on Filamentous Phage. Mimicking the Strategy of the Immune System", J. Mol. Biol. (England) 267 (23):1607–10 (1992)). A library of $V_H$ and $V_k$ genes or analogue thereof may be cloned and displayed on the surface of a phage. Antibody fragments binding specifically to several antigens may be isolated as reported by Marks (Marks, J. D., "By-Passing Immunization. Human Antibodies from V-gene Libraries Displayed on Phage", J. Mol. Biol. (England) 222 (3):581–97 (1991)).

Covalent Oligosaccharide Modifications

The present analogue peptides alone or as hybrid peptides comprising antibodies and fragments thereof may be, e.g., covalently modified utilizing oxidized oligosaccharide moieties. The hybrid analogue peptides may be modified at the oligosaccharide residue with either a peptide labeled with a radioisotope such as 125I or with a chelate such as a diethylenetriaminepentaacetic acid chelate with 111In. The use of oligosaccharides provides a more efficient localization to a target than that obtained with antibodies radiolabeled either at the amino acid chain lysines or tyrosines (Rodwell, J. D. et al., "Site-Specific Covalent Modification of Monoclonal Antibodies: In Vitro and In Vivo Evaluations", PNAS (USA) 83:2632–6 (1986)).

Of the analogue peptides of this invention, preferred are those having the sequences ID Nos. 67 through 73, 75 through 81, 95, 96, and analogues thereof wherein about 1 to 42 amino acids in the FR are substituted per chain with amino acids such as those present in equivalent positions in antibodies of the species for which the analogue is intended, such as human, or fragments thereof comprising 1 to 3 CDRs per chain and flanking regions thereof, each of about 1 to 10 or more amino acids, alone or with an N-terminal fragment of about 1 to 10 amino acids, or up to the complete N-terminal region, or combinations thereof. Examples of possible substitute amino acids in all positions, including the most important positions are shown in Tables 10 and 11 above, and are indicated in the columns titled BrE-3 and KC-4, "Most Preferred Analogue and Preferred Analogue" amino acids substituents. Others are also suitable as may be deduced by the method described herein. These amino acid sequences may be bound by a peptide or non-peptide linker such as is known in the art. Examples of peptide linkers are polylysines, leucine zippers, EGKSSGSGSEJKVD, and (GGGGS)×3, and non-peptide polymers, among others. Effector agents such as peptides and non-peptides may also be attached to the analogue peptides of the invention. These include non-peptide polymers, monomers, atoms, etc., which are discussed below.

Another preferred embodiment comprises a bi-functional analogue peptide having a pair of light and heavy chains of the same specificity attached to one another by a linker, such as those provided above. In another preferred embodiment, a bi-functional analogue peptide comprises one set of light and heavy chains comprising at least one xenogeneic CDR or variable region, e.g., the amino acid sequence ID No. 11 or 13 of Tables 15 and 16, sequence ID No. 95 or 96 from Tables 55 and 56 below, or the respective CDRs alone or separated by 1 to 10 amino acids and up to the entire amino acid segments of their flanking sequences, and optionally with 1 to 10 amino acids of each N-terminal region, sequence ID No. 68, 70 and/or 72, alone or with flanking sequences of varying length, or 76, 78 and/or 80, alone or with flanking sequences of varying length, with the modifications shown above, wherein about 1 to 42 amino acids in the FR are substituted per chain with amino acids such as those present in equivalent positions in antibodies of the target species, or fragments thereof comprising 1 to 3 CDRs per chain and flanking regions thereof, each of about 1 to 10 or more amino acids, alone or with an N-terminal fragment of about 1 to 10 or more amino acids, and one set of light and heavy chains comprising at least one xenogeneic CDR or analogue variable region, e.g., amino acid sequence ID No. 11, 13, 95, or 96 having a different set of substitute amino acids, wherein about 1 to 46 or more amino acids in the FR are substituted per chain with amino acids such as those present in equivalent positions in antibodies of the target species, or fragments comprising 1 to 3 CDRs per chain and flanking regions thereof, each of about 1 to 10 or more amino acids, alone or with an N-terminal fragment of about 1 to 10 or more amino acids, or fragments or combination thereof. Multi-functional hybrid analogue peptides may comprise several identical units or combinations of the above bi-functional analogue peptides of the same or different specificities or xenogeneic species. Preferred analogue peptides are those comprising murine CDRs and other regions substituted with human amino acids.

In another aspect, this invention provides a hybrid analogue polymer that comprises at least one anti-carcinoma analogue peptide and at least one effector agent operatively linked to the peptide, combinations thereof and mixtures thereof. The effector agent utilized in this invention comprises peptide polymers other than the constant region of an antibody of the same species as the CDRs, non-peptide polymers, monomers, and atoms such as metals. In one particularly preferred embodiment, the effector agent may comprise an atom such a radioisotope, an enzyme or a fluorescent label. These effector peptides are suited for in vivo and in vitro assays because they permit the identification of complexes formed by the peptide of the invention. Radioisotopes are particularly preferred for in vivo imaging. Polypeptide labeling is known in the art (Greenwood, F. C., et al., Biochem. J. 89:114–123 (1963)). When a glycosylated polypeptide is utilized, the radiolabel may be attached to the glycosyl residue as is known in the art (Hay, G. W. et al, in Methods in Carbohydrate Chemistry, Vol 5:357, Whistler, R. L. Ed., Academic Press, NY and London (1965)). Effector agents comprising a monomer may be therapeutic, immunogenic or diagnostic agents, radioisotopes, DNA, or RNA monomers, chemical linkers, chemical chelators, transmitter molecules, combinations thereof, or combinations thereof with peptide and non-peptide polymers or copolymers and atoms. Examples of therapeutic agents are anti-neoplastic drugs such as vincristine, intercalation drugs, adriamycin, enzymes, toxins and hormones, among others. Examples of immunogenic agents are other vaccines for carcinomas or for others purposes. Examples of diagnostic agents are radioisotopes and enzymes, among others. Examples of therapeutic, immunogenic and diagnostic agents are toxins, vaccines, and radioisotopes, among others. Examples of radioisotopes are 111In, 35S, 90Y, 186Re, 225Ac, 125I and 99mTc, among others. Examples of DNA and RNA monomers are A, T, U, G, C, among others. Examples of chemical linkers are dithiobis(succinimidyl)propionate and bis-(sulfosuccinimidyl)suberate, among others. Examples of transmitter molecules are cAMP and cGMP, among others. Examples of toxins are ricin A-chain and abrin A-chain, among others.

When the effector agent is a non-peptide polymer linked to the analogue peptide of the invention it may comprise an ester, ether, vinyl, amido, imido, alkylene, arylalkylene, cyanate, urethane, or isoprene polymers, DNA polymers, RNA polymers, copolymers thereof and copolymers thereof with peptide polymers or monomers, or have labeled atoms attached thereto. Examples of these are polyesters, polyethers, polyethyleneglycols, polyvinyls, polyamido and polyimido resins, polyethylenes, polytetrafluoroethylene, poly(ethylene)terephathalate, polypropylene, silicone rubber, isoprenes and copolymers thereof, copolymers of silicone and carbonated polylactic or polyglycolic acid or collagen, and the like. Particularly preferred are biodegradable and bioresorbable or bioabsorbable materials, which if detached from the polypeptide and left in the systemic circulation will not damage endogenous tissues. The effector agent being a peptide may comprise antibodies such as IgA, IgG, IgM, IgE or IgD, the constant region of antibodies of a species different from the variable region or fragments thereof, and the CDRs, variable regions, Fab, Fab', (Fab')2 fragments of antibodies of the classes described above, hormones, enzymes, peptide transmitters and whole antibodies, combinations thereof, and combinations thereof with non-peptide polymers, copolymers, monomers and atoms such as radioisotopes. Examples of other antibodies, Fab, Fab', (Fab')2, CDRs and variable regions thereof are those that specifically bind carcinoma epitopes such as do the BrE-3 and anti-KC-4 antibodies and others having specificities for different carcinoma epitopes such as the BrE-1 (ATCC No. HB 9738), BrE-2 (ATCC No. HB 9795), and Mc5 antibodies, among others, and fragments thereof. All of the antibodies exemplified above selectively bind to the human mammary mucin, and more particularly to the human mammary fat globule. However, antibodies with different specificities for antigens of the target species are also encompassed. Examples of peptide transmitters and hormones suitable for use herein are insulin, growth hormone, FSH, LH, endorphins, and TNF, among others. Examples of enzymes are peroxidase, LDH, alkaline phosphatase and galactosidase, among others.

In a particularly preferred embodiment of the hybrid analogue, the analogue peptide polymer of the invention comprises non-human CDRs and variable region sequences, and the effector peptide comprises the constant region of the light or heavy chains of a human antibody or fragments thereof capable of being bound by immunoglobulins of a different species selectively binding to the constant regions of antibodies, protein G or protein A, or fragments having this binding capability. Also preferred is a half humanized/half chimeric or murine antibody (e.g., humanized light chain and murine or chimeric heavy chain and vice versa). In one of the most preferred embodiments, the analogue peptide(s) comprise(s) all CDRs, flanking sequences of 1 to 10 amino acids connecting them, and an N-terminal region of at least up to 10 amino acids. One preferred embodiment comprises the fully humanized BrE-3HZ or HuBrE3V2, ATCC No. HB 11200 and the fully humanized HuKC-4HZ or HuKC4V2, ATCC No. HB 11455, both of which were deposited under the Budapest Treaty as an example of a best mode of this invention on Nov. 13, 1992 and Sep. 23, 1993, respectively. Other most preferred embodiments are those having chimeric heavy chains and humanized light chains such as the HuBrE3V1, ATCC No. HB 11486, deposited on Nov. 10, 1993, and the HuKC4V1, ATCC No. HB 11454 deposited on Sep. 23, 1993, and those having chimeric light chains and humanized heavy chains such as the HuBrE3V3, ATCC No. HB 11487 deposited on Nov. 11, 1993, and HuKC4V3, ATCC No. HB 11456 deposited on Sep. 23, 1993, all of which deposited under the Budapest Treaty as an example of a best mode of this invention).

The hybrid analogue polymer may comprise two heavy and two light chains, each light and heavy chain comprising at least one CDR or analogue variable region polypeptide or fragments thereof of one species and the constant region and the substitute amino acids of an antibody of a different species such as human, at least one other CDR, analogue variable region, chimeric Fab, Fab' or (Fab')2, fragments thereof, combinations thereof, and mixtures thereof. Still more preferred is a hybrid analogue peptide comprising at least two "humanized" murine-human or chimeric antibody fragments thereof, Fab, Fab' or (Fab')2 fragments thereof operatively linked to one another. The peptide fragments may be covalently attached to one another as is known in the art (Marchis-Mouren G., et al., "HT 29, a Model Cell Line: Stimulation by the Vasoactive Intestinal Peptide (VIP); VIP Receptor Structure and Metabolism", Bioch. 70 (5):663–71

(1988)), or they may be synthesized by methods known in the art (Allen, G., et al., "Production of Epidermal Growth Factor in *Escherichia coli* from a Synthetic Gene", J. Cell Sci. Suppl. 3:29–38 (1985)).

The hybrid analogue polymer of the invention described above may have two heavy and two light analogue chains operatively linked to one another, where each pair of heavy and light chains, has specificity for a different epitope. One example of this analogue peptide is a pair of "humanized" variable region heavy and light chains of a BrE-3 analogue peptide and a pair of "humanized" variable region light and heavy chains of a KC-4 analogue peptide that are covalently attached to one another by a peptide or non-peptide polymer or a disulfide bridge, or non-covalently by means of a leucine zipper or two helical structures, and the like. Non-peptide polymers may be covalently attached to peptides by methods known in the art (Duronio, V., et al., "Two Polypeptides Identified by Interleukin 3 Cross-Linking Represent Distinct Components of the Interleukin 3 Receptor", Exp. Hematol. 20 (4):505–11 (1992)). In another embodiment, the invention provides a hybrid analogue peptide comprising at least one CDR or analogue variable region of the heavy chain of an antibody of a first species or fragments thereof, operatively linked to a first effector agent, and at least one CDR or analogue variable region of the light chain of an antibody of a second species or fragments thereof operatively linked to a second effector agent and combinations thereof, wherein each pair of light and heavy chains has a predetermined specificity, combinations thereof, and mixtures thereof. In another preferred embodiment of the hybrid analogue peptide, at least one CDR or analogue variable region of the heavy chain of a murine antibody or fragments thereof and at least one CDR or variable region of the light chain of a murine antibody or fragments thereof are linked to one another by a non-peptide polymer such as an isoprene polymer or monomer. In still another preferred embodiment, the hybrid analogue peptide of the invention is one wherein at least one pair of light and heavy chains comprising at least one murine CDR or analogue variable region or fragment thereof is linked to at least one other pair of light and heavy chains comprising at least one murine CDR or analogue variable region or fragment thereof. In another embodiment the two or more Fv regions are covalently attached to one another by a peptide or non-peptide polymer or a disulfide bridge, or non-covalently by means of a leucine zipper or two helical structures, and the like. In a most preferred embodiment, the analogue peptides and hybrid polypeptides of the invention have affinity and specificity for an epitope located in the most hydrophilic region of a 20 amino acid tandem repeat that makes up a large part of the polypeptide core of mammary mucin, to hexamer fragments of the sequence APDTRPAPG or trimer TRP fragments shown to afford the strong binding of all five different monoclonal antibodies raised against the human mammary fat globule (Mc1, Mc5, BrE-1, BrE-2 and BrE-3). The monoclonal antibodies were shown to bind to different but overlapping polypeptide epitopes but to have different tissue and tumor specificities, to quantitatively differ in their binding to tumor cells such as breast carcinoma cell lines when observed by flow cytometry and have different competition patterns for binding to the native antigen on breast carcinoma cells. Also preferred amongst antibodies utilized for the preparation of the present analogue peptide and hybrid polypeptide are those that exhibit strong binding to the hexamer peptides described above or to fragments comprising a TRP trimer to tandem repeats thereof. In one most preferred embodiment, the analogue peptide comprises the humanized mutein antibody expressed by the hybridoma cell line having the ATCC Accession No. HB 11200 (BrE-3 HZ). This cell was deposited with the ATCC under the Budapest Treaty on Nov. 13, 1992. In another most preferred embodiment, the analogue peptide comprises the humanized mutein antibody expressed by the hybridoma cell line having the ATCC Accession No. HB 11455 (HuKC-4V2), deposited under the Budapest Treaty on Sep. 23, 1993. These were deposited as the best mode of the invention known to the inventors.

The anti-tumor analogue peptide and/or hybrid analogue polymer of the invention are also provided as an anti-tumor composition along with a carrier or diluent, preferably a pharmaceutically-acceptable carrier or diluent. The anti-tumor analogue peptide and the hybrid polymer provided herein may be present in the composition in an amount of about 0.001 to 99.99 wt %, more preferably about 0.01 to 20 wt %, and still more preferably about 1 to 5 wt %. However, other amounts are also suitable. Carriers generally, and pharmaceutically-acceptable carriers in particular are known in the art and need not be further described herein. The carrier may be provided in a separate sterile container or 5 in admixture with the polypeptide. Typically, saline, aqueous alcoholic solutions, albumin-saline solutions, and propylene glycol solutions are suitable. However, others may also be utilized. When utilized for therapeutic purposes the proteic material must be of a purity suitable for human administration, and the composition may contain other ingredients as is known in the art. Examples of these are other anti-neoplastic drugs such as adriamycin and mitomycin, cytoxan, PALA and/or methotrexate, among others. However, other therapeutic drugs, carriers or diluents, immunological adjuvants and the like may be also be added. When the composition described above is utilized for in vivo imaging, it may comprise about 0.001 to 99.9 wt % analogue peptide, and more preferably about 0.01 to 25 wt % analogue peptide. Typically, when the composition is utilized for therapeutic purposes it may contain about 0.001 to 99.9 wt % analogue peptide, and more preferably about 0.01 to 30 wt % analogue peptide. When utilized for the ex vivo purging of neoplastic cells from bodily fluids such as spinal fluid, the composition may comprise about 0.0001 to 50 wt %, and 20 preferably about 0.01 to 20wt % analogue peptide. When applied to the in vitro diagnosis of tumors such as carcinomas the composition of the invention may comprise about 0.001 to 35 wt % analogue peptide, and more preferably about 0.01 to 10 wt % analogue peptide. Other amounts, however, are also suitable.

Such products find one utility in the treatment of carcinomas, such as breast, lung, ovary, endometrial, pancreas, prostate and colon cancers, among others. The "humanized", "half humanized" and "partially humanized" analogue peptides may be used for the in vivo treatment or diagnosis of humans. The "animalized", "half animalized" and "partially animalized" analogue peptides of the invention may be utilized for the treatment of non-human species such as were described above insofar as the amino acids of the species are substituted for those of the xenogeneic amino acids present at a specific location, and any constant region present in the analogue. The present analogue peptides are particularly suitable for repeated administration to a subject and for long term therapy, such as is the case of metastases and/or the reoccurrence of tumors. Of all analogues described and encompassed herein, the ones most suitable for in vivo applications are those that exhibit low or no binding to serum antigens and to normal cells. Suitable for in vitro or ex vivo uses are those that exhibit good binding to tumor cell antigens such as the carcinoma cell antigen and weak or no binding to normal cells. Even though a patient may have in circulation an interfering amount of a molecule that can bind the analogue peptide, the peptide may still be administered after removal of such serum molecule either by ex-vivo procedures or by administration of flush doses of the analogue peptide or fragments thereof.

A kit for the diagnosis of tumors such as carcinomas may comprise a composition comprising the anti-tumor analogue peptide of the invention, a solid support, anti-tumor antibody (positive control), immunoglobulins of a different species selectively binding the constant regions of the antibody, protein G or protein A, and instructions for its use. This diagnostic kit may be utilized by covalently attaching the antigen or the analogue peptide of the invention or a fusion protein thereof to the solid support by means of a linker as is known in the art. In a particularly preferred embodiment, the support is coated with a polypeptide such as methylated albumin as described in U.S. Pat. No. 4,572,901, the relevant text of which is incorporated herein by reference. When a biological sample is added to a well, the analogue peptide of the invention will bind any tumor antigen present in the biological sample. If a competitive assay is utilized, to the solid supported antigen or hybrid peptide thereof are added a known amount of the analogue peptide and the sample. Thereafter, g-globulin, protein G or protein A in labeled form may be added for detection. Anti-tumor antibodies of a first species may be obtained by challenging a subject of another species with tumor cells such as carcinoma cells, the human milk fat globule mucin and the like, as is known in the art (Peterson, J. A., et al., Hybridoma 9:221 (1990); U.S. Pat. No. 4,708,930). Monoclonal antibodies may be prepared as described by Kohler and Milstein (Kohler, G. and Milstein, C., "Continuous Culture of Fused Cell Secreting Antibody of Predefined Specificity", Nature 256:495–497 (1975)). Suitable for use in this invention are antibodies such as IgG, IgM, IgE, IgA, and IgD. Protein A, protein G and g-globulin may be obtained commercially.

A diagnostic kit for detecting tumors such as carcinomas, and more particularily human carcinomas is provided herein that comprises an anti-tumor composition comprising a hybrid analogue peptide and an effector agent comprising an enzyme, a radioisotope, a fluorescent label and/or a peptide comprising the constant region of an antibody of the species for which use it is intended, or fragments thereof capable of binding anti-constant region immunoglobulins, protein G or A, anti-human tumor antibody, anti-constant region immunoglobulins, protein G or protein A, a solid support having operatively linked thereto an antigen which specifically binds to the anti-tumor hybrid analogue peptide of the invention and the antibody, and instructions for its use. When the effector agent comprises a peptide, such as the constant region of an antibody of the target species, the solid support may have operatively linked thereto an antibody which specifically binds to a portion of a fusion protein other than the antigen of the invention. This permits the binding of the anti-tumor analogue peptide to the antigen molecule now attached to the solid support. Any complex formed between the hybrid analogue peptide of the invention and the supported tumor antigen will, thus, remain attached to the solid substrate. A competitive assay may then be conducted by addition to the solid supported antigen of a known amount of the hybrid antigen peptide and the sample. The amount of antigen present in the sample may be obtained from a dilution curve by addition of anti-constant region immunoglobulins, protein G, protein A or other antibody binding molecules, e.g., labeled, to bind the hybrid analogue peptide that is now attached to the support. This kit may be used in a competitive assay where the supported antigen molecule competes with antigen in the sample for a known amount of the analogue peptide of the invention. The assay was described by Ceriani, R. L., et al. (Ceriani, R. L., et al., Anal. Biochem. 201:178–184 (1992)), the relevant text thereof being incorporated herein by reference.

A tumor such as a carcinoma may be imaged in vivo and/or diagnosed by administering to a subject suspected of carrying a carcinoma the anti-tumor analogue peptide of the invention in radiolabeled form, in an amount effective to reach the tumor cells and bind thereto, and detecting any localized binding of the labeled analogue peptide to the tumor. Typically, the analogue peptide of the invention may be administered in an amount of about 0.001 to 5000 mg/kg weight per treatment, more preferably about 0.01 to 5000 mg/kg weight per treatment, and more preferably about 0.1 to 500 mg/kg weight per treatment. However, other amounts may also be utilized. Radiolabels that may be utilized are 111In, 125I, 99mTc, and 131I, among others. These radioisotopes may be detected with a PET scanner, NMR imaging, and radioactivity counting apparatus that are in wide use by the medical community.

The presence of a tumor such as a carcinoma may be diagnosed in vitro by contacting a biological sample with the anti-tumor analogue peptide or hybrid polypeptide of the invention to form an anti-tumor analogue peptide-antigen complex with any tumor antigen present in the sample, and detecting any complex formed. The biological sample is typically obtained from a human suspected of being afflicted with the tumor. Suitable biological samples are serum, blood, sputum, feces, lymph fluid, spinal fluid, lung secretions, and urine, among others. Clearly, any source of fluid, tissue and the like may be prepared for use in this method as is known in the art.

Neither the hybrid half chimeric/half humanized BrE-3 analogue peptide nor the chimeric BrE-3 polypeptide of the invention of the murine BrE-3 antibody show substantially strong binding. The hybrid BrE-3 analogue peptide of the invention, chimeric BrE-3 polypeptide, and the murine BrE-3 antibody show substantially no strong binding to normal tissue. The hybrid BrE-3 analogue peptide shows a pattern similar to the BrE-3 chimeric polypeptide and the murine BrE-3 antibody. The murine BrE-3 antibody was shown to bind with specificity to carcinoma tumors of the breast, lung, ovary, bladder, and the endometrium, mesothelioma, colon, kidney, liver, pancreas, salivary glands, sarcomas and thyroid, among others. Weak binding was only shown to normal breast tissue, lung tissue, distal convoluted tubes of the kidney, acini of the pancreas and stomach mucosa (Peterson, J. A., et al. (1990), supra). The KC-4 hybrid murine peptide has tissue specificity similar to that of the murine KC-4 antibody. The KC-4 monoclonal antibody was shown to bind specifically and strongly to solid tumor tissue in the lung, colon, kidney, breast, stomach, prostate, pancreas, lymph node duct and lymphoma, and non-specifically and weakly to normal breast, kidney, and stomach tissue. KC-4 also showed some weak binding to normal tissue including spinal cord, uterus, thyroid, tongue, prostate, spleen, adrenal, lung, gall bladder, heart, lymph nodes, colon, liver, brain, testes, thymus, and placenta (U.S. Pat. No. 4,708,930). In one preferred embodiment of the in vitro diagnostic method, the anti-carcinoma analogue peptide added to the biological sample comprises a labeled hybrid analogue peptide. Suitable labeling materials were described above. This method may be practiced, with the solid support containing kit described above, as a competitive assay as disclosed by Ceriani, R. L., et al. (Ceriani, R. L., et al. (1992), supra).

The present analogue peptides are also applicable to the purging of neoplastic cells, such as carcinoma cells, from biological samples, be it fluid or tissue samples. The purging of neoplastic cells from a fluid sample is part of the invention and may be practiced by contacting a biological fluid suspected of comprising neoplastic cells with the analogue peptide of the invention, which is capable of selectively binding to an antigen of the neoplastic cells and allowing the peptide to bind to the antigen, and separating the analogue peptide-cell complex from the remainder of the fluid.

This method may be utilized for purging unwanted cells ex vivo by extracting a biological sample from a patient, eliminating the neoplastic cells therefrom by separation of the analogue peptide-cell complexes or by further addition of an effector such as complement or a toxin or a radioactive label that can act upon the cell and then replenishing the purged sample to the patient. This is typically suitable for use with spinal taps where spinal fluid is rid of carcinoma cells prior to reinjection. Other fluids may also be treated in this manner.

The present analogue peptides may also be applied to the histochemical assessment of the presence of neoplastic cells such as carcinoma cells in a tissue obtained from a subject suspected of being afflicted by a carcinoma by methods that are standard in the art, like the preparation of tissue slices and fixation on a solid substrate to permit the application of the peptide and then the assessment of any binding to neoplastic cells in the sample as indicated by the formation of complexes between the analogue peptide and antigens on or in the cells.

The growth or the size of a primary or metastasized tumor may be inhibited or reduced by administering to a subject in a need of the treatment an effective amount of the anti-tumor hybrid analogue peptide of the invention. Typically, the hybrid analogue peptide may be administered in an amount of about 0.001 to 2000 mg/kg body weight per dose, and more preferably about 0.01 to 500 mg/kg body weight per dose. Repeated doses may be administered as prescribed by the treating physician. However, other amounts are also suitable. Generally, the administration of the hybrid analogue peptide is conducted by infusion so that the amount of radiolabel, toxin or other effector agent present that may produce a detrimental effect may be kept under control by varying the rate of administration. Typically, the infusion of one dose may last a few hours. However, also contemplated herein is the constant infusion of a dose for therapeutic purposes that will permit the maintenance of a constant level of the hybrid polypeptide in serum. The infusion of the hybrid analogue peptide of the invention may be conducted as follows. Intravenous (I.V.) tubing may be pretreated, e.g., with 0.9% NaCl and 5% human serum albumin and placed for intravenous administration. The prescribed dose of the analogue peptide may be infused as follows. Unlabeled analogue peptide may be infused initially. 30 minutes after completion of the unlabeled antibody infusion, 111In-labeled and 90Y labeled antibody may be co-infused. The I.V. infusion may comprise a total volume of 250 ml of 0.9% NaCl and 5% human serum albumin and be infused over a period of about 2 hours depending on any rate-dependent side effects observed. Vital signs should be taken every, e.g., 15 minutes during the infusion and every one hour post infusion until stable. A thorough cardiopulmonary physical examination may be done prior to, and at the conclusion, of the infusion. Medications including acetaminophen, diphenhydramine, epinephrine, and corticosteroids may be kept at hand for treatment of allergic reactions should they occur. The administration of the hybrid analogue peptide of the invention may be repeated as seen desirable by a practitioner. Typically, once a first dose has been administered and imaging indicates that there could be a reduction in the size of the tumor, whether primary or metastasized, repeated treatments may be administered every about 1 to 100, and more preferably about 2 to 60 days. These repeated treatments may be continued for a period of up to about 2 years, and in some circumstances even for longer periods of time or until complete disappearance of the tumor(s). The administration of the hybrid analogue peptides of this invention is typically more useful for therapeutic purposes when a primary tumor has, for example, been excised. Thus, it is primarily, for mopping up after surgical intervention or in cases of cancerous metastases that the present method is of most use.

A pure, isolated analogue polydeoxyribonucleotide that comprises an analogue oligodeoxyribonucleotide encoding the analogue peptide or hybrid peptide of this invention, including all redundant sequences may be applied to the preparation of the peptide. In one preferred embodiment, the analogue polydeoxyribonucleotide of the invention comprises a DNA sequence selected from the group consisting of DNA sequence ID No. 64 of Table 45, or DNA sequence ID No. 65 of Table 46, or DNA segments encoding the CDR fragments sequence ID No. 68, 70 and/or 72, or 76, 78 and/or 80 flanked by 1 to 10 or more amino acids, and the N-terminal fragment of 1 to 10 or more amino acids of human origin. The above DNA sequences may be cloned for expression under the same promoter. Similarly preferred are also the DNAs having the sequence ID No: 93 and/or 94 of Tables 52 and 53 and the segments encoding their CDR fragments alone or separated by DNA segments encoding 1 to 10 or more flanking amino acids and/or terminated by DNA segments encoding 1 to 10 or more amino acids of the N-terminus.

Also provided herein is a hybrid vector that comprises a vector having the analogue polydeoxyribonucleotide of this invention operatively linked thereto. Typically, vectors capable of replication both in eukaryotic and prokaryotic cells are suitable. When the preparation of a glycosylated analogue polypeptide is desired the vector should be suitable for transfection of eukaryotic host cells. In one preferred embodiment, the hybrid vector comprises the analogue polydeoxyribonucleotide and a polydeoxyribonucleotide comprising an oligodeoxyribonucleotide encoding an effector peptide, the effector peptide-encoding polydeoxyribonucleotide being operatively linked to the vector. As already indicated, the various DNA sequences may be cloned for expression under the same promoter. In addition, the polydeoxyribonucleotide encoding the effector polypeptide may also be cloned for expression under the same promoter.

This invention also encompasses a host cell that has been transfected with the hybrid vector described above. Suitable hosts are prokaryotic and eukaryotic hosts such as bacteria, yeast, and mammalian cells such as insect cells and non-producing hybridoma cells, among others. Suitable vectors and/or plasmids for the transfection of each one of these types of hosts are known in the art and need not be further described herein. Also known in the art are methods for cloning DNA sequences into each one of these types of vectors and for transfecting the different types of host cells. Particularly preferred is the cell line having the ATCC Accession No. HB 11200 (BrE-3 HZ).

Polyribonucleotides may be obtained by transcription of the polydeoxyribonucloetides described above as is known in the art. Provided herein are analogue polyribonucleotides comprising analogue oligoribonucleotides encoding at least one CDR or an analogue variable region or fragments thereof, combinations thereof, and combinations thereof with an effector peptide may be prepared by cloning the desired DNA segments and then transcribing the thus obtained hybrid polydeoxyribonucleotide into the corresponding RNA sequences.

The analogue peptide which specifically binds to an antigen on the surface or in the cytoplasm of a neoplastic cell, or is released by the cell, may be produced by a method that comprises cloning the analogue polydeoxyribonucleotide of the invention into a vector to form a hybrid vector, transfecting a host cell with the hybrid vector and allowing the expression of the anti-tumor analogue peptide, and isolating the anti-tumor polypeptide or mixtures thereof. The DNA segment encoding the analogue polypeptide may be obtained by chemical synthesis or by site-specific modification of the sequence encoding the variable region of the xenogeneic species by PCR amplification with specifically designed primers as is known in the art. The fragment DNAs may also be prepared by PCR with primers that introduce a stop codon at a desired position as is known in the art. Preferably, the cloning and transfection steps are conducted by cloning polydeoxyribonucleotides encoding the analogue peptides selected from the group comprising at least one CDR or analogue variable region of the heavy or light chains of the xenogeneic species, antibodies thereof, or fragments thereof. The method may further comprise allowing the expressed analogue peptides to interact with one another to form double chain analogue peptides, one or both analogue peptide chain comprising at least one xenogeneic CDR or variable region of the light or heavy chain of the antibody or fragment thereof modified as described above. Still part of this invention is a method of producing a hybrid analogue peptide comprising an effector peptide and an analogue peptide which specifically binds to an antigen on the surface or in the cytoplasm of a tumor cell such as a carcinoma cell or that is released by the cell, the method comprising transfecting a host cell with the hybrid vector of this invention carrying a DNA sequence encoding the hybrid analogue peptide, allowing the expression of the hybrid analogue peptide, and isolating the hybrid analogue peptide or mixtures thereof. The techniques for obtaining mRNA, conducting reverse transcription and PCR amplification of DNA, chemical synthesis of primers, cloning DNA sequences into a vector, transfecting a host cell, and purifying polypeptides from a culture medium are known in the art and need not be further described herein.

Another aspect of this invention relates to an anti-idiotype peptide that comprises polyclonal antibodies raised against anti-tumor antibodies, the analogue peptide of the invention, monoclonal antibodies thereof, fragments thereof selected from the group consisting of CDRs, Fab, Fab', (Fab')2, and variable region fragments and fragments thereof, analogues thereof selected from the group consisting of Fab, Fab', (Fab')2, and variable regions thereof, wherein about 1 to at least 46 amino acids in the FRs are substituted per chain with amino acids selected from the group consisting of amino acids present in equivalent positions in human antibodies, or fragments thereof comprising 1 to 3 CDRs per chain and flanking regions thereof, each of about 1 to 10 or more amino acids, alone or with an N-terminal fragment of about 1 to 10 or more amino acids. The technique for obtaining anti-idiotype polypeptides is known in the art and need not be further described herein (Nisonoff, A. and Lamoyi, "Implication of the Presence of an Internal Image of an Antigen in Anti-Idiotype Antibodies: Possible Applications to Vaccine Production", Clin. Immunol. Immunopathol. 21:397–406 (1981)). Moreover, the technique for producing hybridomas secreting monoclonal antibodies of a certain specificity is also known in the art (Kohler, G. and Milstein, C. (1975), supra). Techniques for obtaining different antibody fragments were described above or are known in the art (Wilbanks, T., et al., "Localization of Mammary Tumors In Vivo with 131I-Labeled Fab Fragments of Antibodies Against Murine Mammary Epithelial (MME) Antigens", Cancer 48:1768–1775 (1981)). The techniques for modifying peptides to obtain the analogue peptides of this invention have been described above or are known in the art.

The hybrid anti-idiotype polymer may further comprise an effector agent operatively linked to the anti-idiotype polypeptide. Effector agents suitable for use herein were described above for the anti-tumor analogue polypeptide of the invention are also suitable for use with the anti-idiotype polypeptide. Preferred hybrid polymers are polyclonal antibodies raised against the anti-tumor monoclonal antibodies or the analogue peptide of the invention, and a monoclonal antibody obtained by fusion of a B-cell producing an antibody having specificity for the analogue peptide of the invention and an immortalized cell line. Also preferred are fragments of the monoclonal antibody such as Fab, Fab', (Fab')2 and variable region fragments, analogues and fragments thereof as described above, and CDRs. Also, as described above for the anti-tumor polypeptide analogue, preferred are combinations of the above fragments and analogues and combinations of the fragments with whole antibodies and analogues thereof. In another preferred embodiment, the anti-idiotype polymer comprises an analogue variable region of a monoclonal antibody linked to a peptide comprising the hexamers or trimers described above or tandem repeats thereof.

DNA and RNA segments encoding the anti-idiotype polymer and hybrid polymer, a hybrid vector having the DNA operatively linked thereto and a host cell transfected with the hybrid vector are also contemplated herein.

Also provided herein is an anti-tumor vaccine that comprises the anti-idiotype polypeptide of the invention, and a pharmaceutically-acceptable carrier. Typically, the anti-idiotype polypeptide is present in the composition in an amount of about 0.001 to 99.99 wt %, and more preferably about 0.01 to 50 wt % of the composition. However, other amounts are also suitable. Pharmaceutically-acceptable carriers are known in the art and need not be further described herein. The vaccine provided herein may further comprise other ingredients such as adjuvants, and the like. Examples of adjuvants are SAF-1 and Freund's, among others. Suitably, other ingredients typically used for the preparation of vaccines may also be utilized herein. In one embodiment, the vaccine of the invention may be provided in unit form as a powder or in a diluent. In another embodiment, it may be provided in powder form in a sterile container comprising a plurality of doses for preparation prior to utilization. Diluents that are suitable for the preparation of a formulation that may be administered to a patient by injection are known in the art. Examples were provided above.

An anti-tumor vaccination kit is also provided by this invention that comprises, the vaccine described above and a diluent in separate sterile containers, and instructions for its use.

An effective amount of the anti-idiotype polypeptide or hybrid polypeptide described above may be administered to vaccinate a human. Typical amounts administered to vaccinate a human are about 0.001 to 5000 mg/kg body weight/ dose, more preferably about 0.1 to 5000 mg/kg body weight/ dose. The anti-idiotype vaccine of the invention may be administered repeatedly in order to boost the active immunization produced by the first dose. An anti-idiotype antibody very likely resembles the epitope on the neoplastic cell to which the anti-tumor antibody binds. Thus, it may be utilized for the production of an immunological response by a subject such as a human or other mammals against its own neoplastic cells.

When an anti-idiotype polypeptide of, e.g., non-human origin is administered to a, e.g., human, it may produce a somewhat detrimental response. Accordingly, in theory, the smaller the non-human amino acid sequence the anti-idiotype polypeptide contains, the lesser the immunogenic response to its xenogeneic sequences it will elicit in a human. Accordingly, preferred anti-idiotype polypeptides are those containing at least one CDR or variable region of a non-human antibody binding specifically to the anti-tumor polypeptide described herein, optionally as a hybrid polypeptide. Also preferred are human anti-idiotype antibodies, CDR and variable fragments thereof, and fragments thereof that are operatively linked to an effector agent comprising a human polypeptide that may include the constant region of a human antibody and fragments thereof, non-peptide polymers, monomers and atoms that may be radiolabeled as described above. Other types of constructs are also possible, several of which were described above.

Peptides comprising the sequence APDTRPAPG or fragments thereof comprising hexamers with the trimer TRP or TRP by itself or tandem repeats thereof may also be utilized for the preparation of the fusion protein, particularly as part of the antigenic peptide. The peptide comprising the hexapeptide or tripeptide sequences may be utilized as a tandem repeat comprising up to about 10,000 repeats of the basic unit, an in some instances up to about 500,000 repeats. In another embodiment, peptides comprising one or more hexapeptides or tripeptides may be operatively linked to other polypeptide sequences of related or unrelated function, which sequences provide bulk that aids the clearance through the liver and/or kidneys of the immunological complex formed between the circulating unbound or residual antibody or polypeptides utilized for the therapy of neoplasias such as carcinomas and the hexapeptide. The peptides comprising the hexapeptide or tripeptide may also be provided as a hybrid analogue peptide with other analogue peptides described above. In the absence of such treatment, the therapeutic antibody, which may carry a radioisotope, a toxin or other therapeutic molecules, may remain in the circulation for several days and in some instances weeks. This, in the case of a radioactively labeled antibody or analogue of the invention may produce extensive damage, which is highly detrimental to the health of the patient, and in some instances lethal.

Thus, the serum concentration of a circulating antibody or polypeptide that binds to an antigen on the surface or in the cytoplasm of tumor cells or released by the cells may be lowered by administering to a subject the anti-idiotype polypeptide described above, in an amount effective to bind the circulating polypeptide, to thereby accelerate its clearance. Typically, the anti-idiotype polypeptide or hybrid polymer are administered in an amount of about 0.001 to 5000.00 mg/kg body weight/dose, more preferably about 0.01 to 5000 mg/kg body weight/dose. However, other amounts may also be utilized. The administration of the anti-idiotype polypeptide may be infusion as described above.

The growth or the size of a primary or metastasized tumor may be inhibited or reduced by administering to a subject in need of the treatment an effective amount of an antibody or an anti-tumor hybrid analogue peptide comprising an effector agent selected from the group consisting of radioisotopes, therapeutic drugs and vaccines, and an anti-tumor polypeptide which specifically binds to an antigen on the surface or in the cytoplasm of a tumor cell or released by the cell, allowing the hybrid polypeptide to reach the tumor and the polypeptide to bind thereto, and administering to the subject an amount of the anti-idiotype polypeptide of the invention effective to bind residual or unbound circulating hybrid analogue peptide to thereby accelerate the clearance of the hybrid polypeptide.

Having now generally described this invention, the same will be better understood by reference to certain specific examples, which are included herein for purposes of illustration only and are not intended to be limiting of the invention or any embodiment thereof, unless so specified.

EXAMPLES

Example 1

Methods Utilized

The procedures utilized herein for the reverse-transcription (RT) of RNAs encoding the variable regions and the subsequent amplification of the cDNAs by the polymerase chain reaction (PCR) have been described (Orlandi, R., et al., "Cloning Immunoglobulin Variable Domains for Expression by the Polymerase Chain Reaction", PNAS (USA) 86:3833–3837 (1989); Coloma, M. J., et al., "Primer Design for the Cloning of Immunoglobulin Heavy-Chain Leader-Fvs from Murine Hybridoma Cells Using the PCR", Bio. Techniques 11:152–156 (1991); Gavilondo-Cowley, J. V., et al., "Specific Amplification of Rearranged Immunoglobulin Fv Genes from Murine Hybridoma Cells", Hybridoma 9:407–417 (1990)).

Total RNA is an adequate substrate for RT-PCR. Polyadenylated RNA was utilized herein, however, because it contains only minor levels of contaminating ribosomal RNA and practically no DNA. The polyadenylated RNA was isolated with a Fast Track mRNA isolation kit (Invitrogen Corporation, San Diego, Calif.).

The oligonucleotides were synthesized on a PCR-Mate EP DNA synthesizer model 391 (Applied Biosystems, Foster City, Calif.). A PCR murine Ig primer set was purchased from Novagen (Madison, Wis.), and complementary DNA (cDNA) was prepared with an RNA PCR kit (Perkin Elmer-Cetus, Norwalk, Conn.).

PCR DNA fragments were cloned directly into pCR1000, using a TA cloning kit (Invitrogen Corporation, San Diego, Calif.). Plasmid DNA was isolated with a kit purchased from Qiagen (Tchapsworth, Calif.), and DNA sequencing was conducted with a Sequenase 2.0 DNA sequencing kit (United States Biochemical, Cleveland, Ohio) using aqueous 5'a-$^{35}$SdATP at 600 mCi/mmol (Amersham Corporation, Arlington Heights, Ill.).

Sequence analyses were performed on a Macintosh computer using the program GeneWorks (IntelliGenetics, Inc, Mountain View, Calif.).

Example 2

Tissue Culture Media

SP2/0-Ag14 cells (Shulman, M., et al. (1978), below) were cultured either in Dulbecco's modified Eagle's medium (DME): fetal bovine serum (FBS), 90:10 (v/v) or in a mixture of DME:RPMI:FBS, 45:45:10 (v/v/v) or RPMI:FBS, 90:10 (v/v). Penicillin and streptomycin were added to prevent bacterial growth. When serum-free medium was utilized, it contained an HL-1 supplement as directed by the manufacturer (Ventrex Labs., Portland, Me.). The freezing medium was 10% DMSO in bovine serum.

Example 3
PCR Primers

Primers and primer mixtures MulgkV$_L$5'-C, MulglV$_L$3'-1, MulgV$_H$5'-C, MulgV$_H$5'-F, and MulggV$_H$3'-2 were part of a primer set purchased from Novagen. Their sequences may be obtained from Novagen. Other primers were synthesized by the inventors. These sequences are shown in Table 12 below.

TABLE 12

Synthetic Primers

| | |
|---|---|
| J02- T GAA GCT TGC TCA CTG GAT GGT GGG AA | (Seq. ID No: 1); |
| J03- AGA TGG GGG TGT CGT TTT GG | (Seq. ID No: 2); |
| J04- GCT TGA ATT CCA GGG GCC AGT GGA TAG A | (Seq. ID No: 3); |
| VH1BACK (*) - AG GT(CG) (CA)A(GA) CTG CAG (CG)AG TC(TA) GG | (Seq. ID No: 4); |
| J014- ATG TAC TTG GGA CTG AAC TAT GTC TT | (Seq. ID No: 5). |

*Orlandi, R., et al. (Orlandi, R., et al. "Cloning Immunoglobulin Variable Domains for Expression by the Polymerase Chain Reaction", PNAS (USA) 86: 3833–3837(1989)).

Example 4
Cloning of Chimeric BrE-3 Antibody Polydeoxyribonucleotide

Two expression vectors pAG4622 and pAH4604 were utilized herein (Coloma, M. J., et al., "Novel Vectors for the Expression of Antibody Molecules Using Variable Regions Generated by PCR", J. Immunol. Methods 152:89–104 (1992)). These were kindly provided by S. L. Morrison (Dept. of Microbiology and Molecular Genetics, UCLA).

The construction and expression of chimeric genes was performed as described by Coloma et al. (Coloma, M. J., et al. (1992), supra).

Oligonucleotides were synthesized and used in a PCR mixture to produce variable heavy ($V_H$) and variable light ($V_L$) fragments with the correct ends for insertion into the pAG4622 and pAH4604 expression vectors. There sequences are shown in Table 13 below.

TABLE 13

Synthesized Oligonucleotides

| | | |
|---|---|---|
| J016 (senseV$_H$ leader) | - GGG GATATC CACC ATG TAC TTG GGA CTG AAC TAT GTC TTC A | (Seq. ID No: 6); |
| J017 (senseV$_L$ leader) | - GGG GATATC CACC ATG AAG TTG CCT GTT AGG CTG TTG GT | (Seq. ID No: 7); |
| J018 (anti-sense JH3) | - GGG GCTAGC TGC AGA GAC AGT GAC CAG AGT CC | (Seq. ID No: 8); |
| J019 (anti-sense Jk1) | - GGG GTCGACTTAC G TTT GAT TTC CAG CTT GGT GCC TCC A | (Seq. ID No: 9). |

The original pCR1000 clones were utilized as the starting templates for the PCR. The new PCR products were cloned back into pCR1000 and their sequence confirmed. Correctly modified and amplified fragments were excised with either EcoR V and Sal I (for $V_L$) or with EcoR V and Nhe I (for $V_H$). These fragments were then ligated into the respective vectors, which had been cut open with the appropriate restriction enzymes. Both the vectors and the inserts were purified from an agarose gel prior to ligation, using the Bio101 GeneClean kit (glass beads) (La Jolla, Calif.).

Example 5
Expression of Murine-Human Chimeric BrE-3 Antibody

The $V_H$ and $V_L$ regions in the final murine-human chimeric antibody were sequenced once again to verify that their sequences were correct.

The non-producer myeloma cell line SP2/0-Ag14, (ATCC: CRL 1581, Shulman, M., et al., "A Better Cell Line for Making Hybridomas Secreting Specific Antibodies", Nature 276:269–270, (1978)) was transfected, and a chimeric antibody were isolated as described by Coloma, M. J.

et al. (1992), with the following modification. The selection was only undertaken for the uptake of hisD by adding 5 mM histidinol to the medium and readjusting the pH to 7.4 with NaOH.

Example 6
Production of Transfected Hosts

After ten days, the stable transfectant colonies were clearly established at a frequency of approximately $10^{-5}$. The colonies were transferred to a normal medium (without histidinol) and the supernatants from stable transfectants were assayed for the presence of the murine-human chimeric BrE-3 antibody. This was done by capturing the secreted murine-human chimeric BrE-3 antibody with a plate-bound goat anti-human-k antibody and developing with goat anti-human-g antibody as described by Coloma et al. with the following modification. The secondary antibody utilized herein was radiolabeled with $^{125}$I.

Example 7
Confirmation of Murine-Human Chimeric BrE-3 Antibody Expression

The supernatants were assayed for binding to human milk fat globule (HMFG) as described by Ceriani et al. (Ceriani R. L., et al., Diagnostic Ability of Different Human Milk Fat Globule Antigens in Breast Cancer", Breast Cancer Res. Treat. 15:161–174 (1990)). HMFG was bound to the microtiter plates as described previously (Ceriani R. L., "Solid Phase Identification and Molecular Weight Determination of Cell Membrane Antigens with Monoclonal Antibodies", in: Monoclonal antibodies and functional cell lines. Progress and application, Bechtol, K. B., McKern, T. J., and Kennett, R., Eds., Plenum Press, New York, pp 398–402 (1984)).

Most colony supernatants were positive by both assays. The colonies that secreted the highest level of chimeric antibody into the supernatants, as determined by these assays, were subcloned and subsequently adapted to serum-free medium for the purification of antibody.

Example 8
Determination of Affinity Constants

The antibody-antigen affinity constants for the murine-human chimeric antibody anti-human milk mucin and the whole murine antibody were determined by obtaining the reciprocal value of the concentration of competing unlabeled monoclonal antibody giving 50% binding as described by Sheldon et al. (Sheldon, K., et al., "Characterization of Binding of Four Monoclonal Antibodies to the Human Ovarian Adenocarcinoma Cell Line HEY", Biochem. Cell Biol., 65: 423–428, (1987)). The protocol for the assay was as follows.

Microtiter plates (Dynatech, Chantilly, Va.) were prepared using successive layers of methylated BSA, glutaraldehyde, anti-b-galactosidase and the bacterial fusion protein 11-2 (a hybrid of b-galactosidase and human mammary mucin) as described in Ceriani et al. (Ceriani, R. L., et al., "A Novel Serum Assay for Breast Cancer Epithelial Antigen Using a Fusion Protein", Anal. Biochem. 201:178–184 (1992). Each well contained 388 ng of the 11-2 fusion protein. To each well were added 25 ml $^{125}$I-BrE-3 (ATCC No. HB 10028) in RIA buffer (10% bovine calf serum, 0.3% triton X-100, 0.05% sodium azide pH7.4, in phosphate buffered saline), and competed with 25 ml of either unlabeled murine antibody or murine-human chimeric antibody in RIA buffer at final concentrations in the nanomolar range.

Iodinations were performed with $^{125}$l (17 Ci/mg, Nordion International Inc., Kanata, Ontario, Canada). 50 micrograms of monoclonal antibody BrE-3 (Coulter, Hialeah, Fla.) were labeled at a specific activity of 9.56 mCi/mg using the chloramine T method as described by Ceriani, R. L. and Blank, E. W., (Ceriani, R. L., and Blank, E. W., "Experimental Therapy of Human Breast Tumors with 131I-Labeled Monoclonal Antibodies Prepared Against the Human Milk Fat Globule", Cancer Res. 48:4664–4672 (1988)). When the counts of bound radiolabeled anti-BrE-3 murine antibody were plotted an the Y axis and the logarithm of the nanomolar (nM) concentration of competing unlabeled anti-BrE-3 murine antibody or murine-human chimeric antibody were plotted in the X axis, both curves overlapped within 5% error (Figure not shown).

This proves that the variable region's affinity characteristics have been preserved.

Example 9
Affinity Binding Constants for BrE-3 Murine and Murine-Human Chimeric Antibody The purified murine-human chimeric BrE-3 antibody and purified murine BrE-3 antibody gave similar competition curves when tested against $^{125}$I-labeled murine BrE-3 binding to its antigen. The affinity binding constants of the murine antibody and the murine-human chimeric antibody were determined in independent competition assays as described in Example 8 above. The values of the constants are $2.68 \times 10^8$ M$^{-1}$ and $3.75 \times 10^8$ M$^{-1}$ for the hybrid chimeric BrE-3 polypeptides and for the murine BrE-3 antibody, respectively. These values are not distinguishable at a 95% confidence interval.

Example 10
Amplification of cDNAs Encoding BrE-3 Antibody Variable Regions

The cDNAs that encode the anti-BrE-3 murine immunoglobulin variable domains ($V_H$ and $V_L$) were prepared by reverse transcription and PCR amplification (RT-PCR) from polyadenylated RNA isolated from $10^8$ BrE-3 hybridoma cells by the following procedure.

The JO2, JO3, JO4, J)14 and $V_H$1BACK primers were synthesized, and their sequences shown in Example 3 above. Other primers were purchased from Novagen. With the exception of $V_H$1BACK, which is a framework-specific primer, all sense primers are specific for the leader peptide region. All anti-sense primers are specific for the constant regions. The degenerate I chain of the specific primer MulglV$_L$3'-1 (from Novagen), was used to isolate the k chain cDNA clones because of the similarity of the l and k. An identical k chain clone was isolated with primer J02 which is specific for the k chain constant domain.

The $V_H$ region cDNA could not be isolated with the available leader peptide primers. Thus, the $V_H$1BACK primer was used, which yielded the $V_H$ cDNA g72. The leader-peptide primer JO14 was then designed by extrapolating from the framework sequence of g72, using cataloged nucleotide sequences (Kabat, E. A., et al., "Sequences of Proteins of Immunological Interest", U.S. Dept. Health and Human Services, NIH publication No. 91–3242, 5th Edition (1991). After sequential PCR reactions, this new primer yielded the complete $V_H$ framework cDNA. This information is summarized in Table 14 below.

TABLE 14

| | Primer Combinations for PCR Amplification | | |
|---|---|---|---|
| | Clone No. | Sense Primers | Antisense Primers |
| $V_L$ | 152 | MulgkVL5'-C | JO2 |
| | 164 | MulgkVL5'-C | MulgIVL3'-1 |
| $V_H$ | g72 | $V_H$1BACK | (JO3 or JO4) |
| | 1012 | JO14 (1st PCR) | JO3 |
| | | JO14 (2nd PCR) | JO4 |
| | 1043 | JO14 (1st PCR) | JO3 |
| | | (MulgVH5'-C + MulgVH5'-F) (2nd PCR) | MulggVH3'-2 |

Example 11

Isolation of Amplified BrE-3 $V_L$ and $V_H$ cDNA and Sequences

The PCR products were cloned without prior purification into pCR1000 (Invitrogen) and sequenced in both directions. Clones 152, 164, 1012, and 1043 were isolated independently during different RT-PCR runs. The sequences of $V_L$ clones 152 and 164 were found to be identical, as were the sequences of the $V_H$ clones 1012, 1043. The $V_H$ and $V_L$ DNA sequences and their derived protein sequences are shown in Tables 15 and 16 below.

TABLE 15

BrE-3 VL Nucleotide and Derived Protein Sequences

DNA Sequence

ATG AAG TTG CCT GTT AGG CTG TTG GTG CTG TTG TTC TGG ATT CCT GCT TCC ATC AGT GAT GTT    (Seq. ID No: 10)

GTG ATG ACC CAA ACT CCA CTC TCC CTG CCT GTC AGT CTT GGA GAT CAA GCT TCC ATC TCT TGC

AGA TCT AGT CAG AAC CTT GTA CAC AAC AAT GGA AAC ACC TAT TTA TAT TGG TTC CTG CAG AAG

TCA GGC CAG TCT CCA AAG CTC CTG ATT TAT AGG GCT TCC ATC CGA TTT TCT GGG GTC CCA GAC

AGG TTC AGT GGC AGT GGA TCA GAG ACA GAT TTC ACA CTC AAG ATC AGC AGA GTG GAG GCT GAG

GAT CTG GGA GTT TAT TTC TGC TTT CAA GGT ACA CAT GTT CCG TGGACGTTCGGTGGAGGCACC

AAGCTGGAAATCAAAC

Amino Acid Sequence m k l p v r l l v l L F W l P A S l S D1 V V M T Q T P L S L    (Seq. No: 11)

P V S L G D Q A S l S C R S S Q N L V H N N G N T Y L Y W F

L Q K S G Q S P K L L I Y R A S I R F S G V P D R F S G S G

S E T D F T L K l S R V E A E D L G V Y F C F Q G T H V P W

I F G G G T K L E l K

TABLE 16

BrE-3 VH Nucleotide and Derived Protein Sequences

DNA Sequence

ATG TAC TTG GGA CTG AAC TAT GTC TTC ATA GTT TTT CTC TTA AAA GTC CAG AGT GAA GTG    (Seq. ID No: 12)

AAG CTT GAG GAG TCT GGA GGA GGC TTG GTG CAA CCT GGA GGA TCC ATG AAA CTC TCT TGT

GCT TCT GGA TTC ACT TTT AGT GAT GCC TGG ATG GAT GCC TGG ATG GAC TGG GTC CGC CAG

TCT CCA GAG AAG GGG CTT GAG TGG GTT GCT GAA ATT AGA AAC AAA GCC AAT AAT CAT GCA

ACA TAT TAT GAT GAG TCT GTG AAA GGG AGG TTC ACC ATC TCA AGA GAT GAT TCC AAA AGT

AGA GTG TAC CTG CAA ATG ATA AGC TTA AGA GCT GAA GAC ACT GGC CTT TAT TAC TGT ACT

GGG GAG TTT GCT AAC TGG GGC CAG GGG ACT CTG GTC ACT GTC TCT GCA G

TABLE 16-continued

BrE-3 V_H Nucleotide and Derived Protein Sequences

Amino Acid Sequence m y l g l n y v f l V F L L K G V Q S E l V K L E E S G G G L  (Seq. ID No: 13)

V O P G G S M K L S C A A S G F T F S <u>D A W M D</u> W V R Q S P

E K G L E W V A <u>E I R N K A N N H A T Y Y D E S V K</u> G R F T

I S R O D D S K S R V Y L Q M I S L R A E D T G L Y Y C T G E

<u>F A N</u> W G Q G T L V T V S A

The sequences were interpreted as described by Kabat et al. (1991). The residues that are shown in lower case correspond to PCR primers. The mature chains begin at D1 ($V_L$) and E1 ($V_H$), respectively. The amino-acids that are underlined are those corresponding to the CDRs. The underlined nucleotides indicate joining segments.

The framework and CDR polypeptide segments were identified according to Kabat et al. (1991), supra. $V_L$ is a group IIk chain. Part of the CDR 3 and all of framework 4 (FR4) are encoded by $J_{k1}$. $V_H$ belongs to group IIIc. CDR 3 and FR4 are encoded by $J_{H3}$. Little or nothing remains from an unidentified D minigene. Thus, the CDR 3 is only 4 amino-acids long.

Example 12
Comparison of cDNA deduced Amino Acid Sequence with Directly Determined N-Terminal Fragment Sequence Table 17 below shows a comparison between the cDNA-derived polypeptide sequence and the polypeptide sequence determined directly from purified murine BrE-3 monoclonal antibody.

TABLE 17

Comparison of cDNA-Deduced Protein Sequence with Directly Determined N-terminal Protein Sequence

| VL | cDNA-deduced | DVVMTQTPLSLPVSLGDQASISCRS |
| VL | Protein sequence | GVVMTQTPLSLPVVLGDQASIIXRX |
| VH | cDNA-deduced | EVKLEESGGGLVQPGGSMKLSCAAS |
| VH | Protein sequence | EVKLEESGGVLVQPGGSMKLSSAAS |

The murine BrE-3 antibody was reduced with 5% mercaptoethanol, separated on a 10% SDS polyacrylamide gel, and electroblotted onto a ProBlott membrane (Applied Biosystems, Foster City, Calif.). Amino acid sequencing was performed directly on the immobilized bands by the Biotechnology Instrumentation Facility, University of California, Riverside. The protein sequence given here is the sequencer's best guess.

Once the variable region cDNAs were cloned, it was confirmed that, in fact, they encoded the variable regions of the murine BrE-3 antibody and not those of another antibody by comparing the cDNA-derived amino acid sequences of the cloned murine BrE-3 antibody variable region with the N-terminal sequence of the purified anti-BrE-3 murine antibody directly determined by a single run of protein sequencing. The cDNA sequences were shown to be accurate by comparison with two independently reverse transcribed clones.

The general agreement between the predicted and the determined amino-acid sequences shows that the cloned cDNAs encode polypeptides of the same class and subclass as the variable regions of the murine BrE-3 antibody. This indicates that the cDNAs encode authentic variable regions. The authenticity of the variable region polypetide and, therefore, that of the murine-human chimeric BrE-3 antibody is unquestionable given that the variable regions and the chimeric antibody affinity constant are indistinguishable from those of the murine BrE-3 antibody.

Example 13
Construction of Murine-Human Chimeric Antibody Genes

The vectors used were developed by Coloma et al. (Coloma, M. J., et al. (1992), supra) and kindly provided by S. L. Morrison (Dept. of Microbiology and Molecular Genetics, UCLA). Both vectors were derived from pSV2 (Mulligan, R. C., and Berg, P., "Expression of a Bacterial Gene in Mammalian Cells", Science 209:1422–1427 (1980)), and contain genomic fragments encoding either the heavy or the light chain constant domains. The vectors accept cDNAs that encode the $F_v$ regions. To ligate the $F_v$ cDNAs to the vectors, restriction ends were added to the cDNAs in a set of PCR reactions, using the JO16, JO17, JO18 and JO19 primers.

The pAG4622 light chain vector contains the gene for the human k chain constant region, including the J-C intron. It encodes xanthine-guanine phosphoribosyltransferase or gpt (Mulligan, R. C., and Berg, P., "Selection for Animal Cells that Express the Escherichia coli Gene Coding for Xanthine-Guanine Phosphoribosyltransferase", PNAS (USA) 78:2072–2076 (1981)) as a dominant selectable marker. It accepts the murine VL cDNA between the ribosome binding site (Kozak, M., "Compilation and Analysis of Sequences Upstream from the Translational Start Site in Eukaryotic mRNAs", Nucleic Acids Res. 12:857–872 (1984)), which is preceded by the VH promoter from the anti-dansyl murine monoclonal antibody 27.44 (Coloma, M. J., (1992), supra), and the J-C intron. The J-C intron contains the k chain enhancer (Potter, H., et al., "Enhancer-Dependent Expression of Human k Immunoglobulin Genes Introduced into Murine Prep-B Lymphocytes by Electroporation", PNAS (USA) 81:7161–7165 (1984); Emorine, L., et al., "A Conserved Sequence in the Immunoglobulin J Kappa-C Kappa Intron: Possible Enhancer Element", Nature 304: 447–449 (1983)).

The pAH4604 heavy chain vector contains the gene for the heavy chain g1 constant region, but no J-C intron. It encodes histidinol-dehydrogenase or hisD (Hartman, S. C. and Mulligan, R. C. Two Dominant-Acting Selectable Markers for Gene Transfer Studies in Mammalian Cells", PNAS (USA) 85:8047–8051 (1988)) as a dominant selectable marker. It accepts the murine $V_H$ cDNA between the dansyl promoter-ribosome binding site and the constant g1 gene. The vector also contains an insert that encodes the heavy chain enhancer (Rabbitts, T. H., et al, "Transcription Enhancer Identified Near the Human C mu Immunoglobulin Heavy Chain Gene is Unavailable to the Translocated c-myc Gene in a Burkitt Lymphoma", Nature 306:806–809 (1983)).

The new $V_H$ and $V_L$ DNA fragments with appropriate restriction ends were integrated into pAH4604 and pAG4622 as described in Example 4 above. The vectors were then electroporated (together) into SP2/0-Ag14 myeloma cells as described by Coloma et al. (1992), supra.

Example 14
Characterization of Murine-Human Chimeric BrE-3 Antibody

The supernatants from stable transfectants were assayed for the presence of the murine-human chimeric antibody as described in Examples 6 and 7 above. High producing transfectants were subcloned and subsequently adapted to grow in serum-free medium. The murine-human chimeric antibody produced by the myeloma cell line was then purified from the culture supernatant using a Sepharose 4B-protein A column (Bio-Rad, Richmond, Calif.) as described in Ey, P. L., et al. (Ey, P. L., et al., "Isolation of Pure IgG1, IgG2 a and IgG2b Immunoglobulins from Murine Serum Using Protein A-Sepharose", Immunochemistry 15:429–436 (1978)). Antibody disulfide bonds were reduced to separate the light and heavy chains by heating for 10 min at 65° in Laemmli loading buffer containing 5% beta-mercaptoethanol. The separated chains were then chromatographed on a SDS polyacrylamide gel (10%). The reduced murine-human chimeric BrE-3 antibody and murine antibodies were eletrophoresed in separate lanes next to 97.4, 66.2, 45.0, 31.0 and 2.5 Kdalton protein markers. Table 18 below shows the apparent molecular weights of the two bands obtained for both.

TABLE 18

Apparent Molecular Weights of Light and Heavy Chains of Murine and Chimeric BrE-3 Antibodies

| Chimeric Antibody | | Murine Antibody | |
|---|---|---|---|
| Heavy Chain (Kd) | Light Chain (Kd) | Heavy Chain (Kd) | Light Chain (Kd) |
| 50 | 30 | 49 | 29 |

The heavy and light chains of the anti-BrE-3 chimeric antibody separate as expected when electrophoresed on a polyacrylamide gel.

Example 15
Tissue Binding Studies with Chimeric BrE-3 Antibody

Immunohistochemical staining using the immunoperoxidase technique of consecutive human breast carcinoma tissue sections was conducted with the murine-human chimeric BrE-3 antibody. A control was stained with the anti-human secondary antibody only. Positive staining resulted from the use of the murine-human chimeric BrE-3 antibody, followed by the anti-human antibody specific binding. (Pictures not shown).

The breast carcinoma tissue sections were stained with the supernatant of the transfected cells using the Vectastain ABC method (Vector Labs, Burlingame, Calif.). The tissue stained with the goat anti-human Ig secondary antibody only shows background or non-specific staining of necrotic areas of the tissue section.

The tissue stained with murine-human chimeric BrE-3 antibody, followed by the secondary antibody, shows specific staining of the breast carcinoma cells in the breast tissue sections.

Example 16
Chimeric BrE-3 Antibody Imaging Studies

The anti-BrE-3 murine monoclonal antibody has been shown to be highly effective for imaging and for the radioimmunotherapy of breast cancers. For example, in a pharmacokinetic study of 15 breast cancer patients conducted with an $^{111}$In-MXDTPA-BrE-3 radio-immunoconjugate (anti-BrE-3 antibody), the serum levels were low in most patients, the blood clearance correlated with the circulating antigen and the imaging results showed that about 86% of all sites could be imaged (Liebes, L., et al., "Pharmacokinetics of $^{111}$In-BrE-3 Monoclonal Antibody in Patients with Breast Carcinoma", Proc. Am. Assoc. Cancer Res. 33:216(Abs No. 1292) (1992)). A $^{90}$Y-BrE-3 radioimmunoconjugate having similar pharmacokinetic characteristics and extrapolating the $^{111}$In-BrE-3 dosimetry results provide a superior therapeutic agent, as well.

As with many other monoclonal antibodies, however, the clinical applications of the anti-BrE-3 murine antibody, a whole murine antibody, are limited by the HAMA response. A chimeric monoclonal antibody should give a more restricted HAMA response.

Example 17
Chimeric BrE-3 Antibody Immunogenicity

The BrE-3 variable region murine polypeptides have been cloned without the constant regions to produce less immunogenic polypeptides than the parent murine antibody. It has, moreover, been shown herein that the murine-human chimeric BrE-3 antibody lacking its original murine constant region preserves its antigen binding characteristics.

An BrE-3 antibody variable region alone or as a murine-human chimeric antibody also containing a constant human region or fragment thereof would be significantly less immunogenic to humans than the parent murine antibody. The hybrid polypeptide comprising the variable region of the BrE-3 antibody and the constant region of a human antibody was shown to preserve the original binding affinity of the murine antibody. In this hybrid polypeptide, approximately 2/3 of its contiguous non-human immunogenic targets ($C_L$ and $C_H$ regions) were entirely replaced by human constant domains.

Example 18
PCR Primers used in First Isolation of Anti-KC-4 cDNAs

The PCR primers were purchased from Novagen (Madison, Wis.). Their sequences, reproduced from the booklet provided by Novagen, are shown in Table 19 below.

TABLE 19

PCR Primer Sequences

Mulgk$V_L$5'-C:
sense primer mix for kappa leader.

(Seq. ID No: 14)
ACTAGTCGACATGAAGTTGCCTGTTAGGCTGTTGGTGCTG
(Seq. ID No: 15)
ACTAGTCGACATGGAGWCAGACACACTCCTGYTATGGGT

TABLE 19-continued

PCR Primer Sequences (Seq. ID No: 16)
ACTAGTCGACATGGATTTWCAGGTGCAGATTWTCAGCTTC MulgkV$_L$'-1:
antisense kappa constant region.

(Seq. ID No: 17)
CCCAAGCTTACTGGATGGTGGGAAGATGGA

MulgV$_H$5'-F:
sense primer mix for heavy chain leader.

(Seq. ID No: 18)
ACTAGTCGACATGRACTTTGGGYTCAGCTTGRTTT
(Seq. ID No: 19)
ACTAGTCGACATGAGAGTGCTGATTCTTTTGTG
(Seq. ID No: 20)
ACTAGTCGACATGGATTTTGGGCTGATTTTTTTATTG

MulggV$_H$3'-2:
antisense gamma constant region.

CCCAAGCTTCCAGGGRCCARKGGATARACIGRTGG
(Seq. ID No: 21)

Example 19
Cloning of Murine-Human Chimeric anti-KC-4 Antibody Ribonucleotide The two expression vectors pAG4622 and pAH4604 described in Example 4 were utilized.

Oligonucleotides synthesized and used in a PCR to produce V$_H$ and V$_L$ fragments with the correct ends for insertion into the pAG4622 and pAH4604 expression vectors are shown in Table 20 below.

TABLE 20

PCR Primers Sequences

J020 - sense kappa leader
(Seq. ID No: 22)
GGG GATATC CACC ATG AAG TTG CCT GTT AGG CTG TTG J021 - antisense JK2
(Seq. ID No: 23)
CCC GTCGACTTAC G TTT TAT TTC CAG CTT GGT CCC CCC T J022 - sense V$_H$ leader
(Seq. ID No: 24)
GGG GATATC CACC ATG GAC TTT GGG CTC AGC TTG GTT TT J024 - antisense JH3
(Seq. ID No: 25)
CCC GCTAGC TGC AGA GAC AGA GAC CAG AGT CC The original pCR1000 clones were the starting templates for the PCR and the rest of the procedures as described in Example 4 above.

Example 20
Expression of the anti-KC-4 Chimeric Antibody Gene

The V$_H$ and V$_L$ regions in the anti-KC-4 murine-human chimeric antibody were sequenced once again to verify that their sequences were correct. The transfection of the non-producer myeloma cell line SP2/0-Ag14, (ATCC: CRL 1581) and isolation of polypeptide was conducted as described in Example 5 above.

Example 21
Production of Transfected Hosts

After ten days, stable transfectant colonies were clearly established at a frequency of approximately 1/10,000. The colonies were transferred to normal medium and the assays conducted as described in Example 6 above.

Example 22
Confirmation of anti-KC-4 Murine-Human Chimeric Antibody Expression The supernatants were assayed for binding to human milk fat globule (HMFG) and the breast epithelial mucin (BEM) as described previously in Example 7 above. HMFG and BEM were bound to the microtiter plates as described previously by Ceriani, R. L. (1990), supra. In this radioassay the bound anti-KC-4 chimeric antibody (HMFG and BEM) was detected by anti-human gamma chain conjugated to $^{125}$I. Most colony supernatants were positive by both assays. The colonies that secreted the highest level of chimeric antibody in the supernatants, as determined by these assays, were subcloned.

Example 23
Western Blot 75 ml of the culture supernatant was added to 20 ml of 4× Laemmli buffer and 5 ml b-mercaptoethanol and the mixture was heated at 65/C. for 15 min., in order to reduce antibody disulfide bonds and, thus, separate heavy from light chains. 20 ml of the treated sample was chromatographed in duplicate lanes on a 10% SDS polyacrylamide gel together with other antibodies that were treated similarly and that were loaded for comparison. Pre-stained size markers (BioRad, Richmond, Calif.) were also loaded.

The chromatographed proteins were electroblotted onto a ProBlott membrane (Applied Biosystems, Foster City, Calif.) in 90% 30 mM CAPS pH11, 10% methanol, for 1 hour at 25 V and at 4° C. The membrane was cut into 2 parts containing identical antibody samples. The 2 membranes were immersed in 20% bovine calf serum in PBS and shaken slowly at room temperature for 1 hour 35 min. $^{125}$I-labeled goat anti-human k chain antibody was added to one membrane and $^{125}$I labeled goat anti-human g chain antibody to the other membrane. Antibodies were labeled at a specific activity of approximately 10 mCi/mg using the chloramine T method as described by Ceriani, R. L. and Blank, E. W. (1988), the labeled antibodies were diluted to 4,000 cpm/ml in RIA buffer.

After incubating 3 hours at room temperature the blots were washed twice in TBS for 10 min each time, once in TBST (50 mM TRIS pH7.5, 3 mM EDTA 25 mM NaCl) 10 min and once more in TBS (TBS with 0.05% Tween 20) for 10 min. The membranes were dried and exposed to Kodak XAR film.

Western blot analysis of culture supernatants revealed that three antibody chains were expressed that corresponded to the three antibody chains seen in the original anti-KC-4 murine antibody. These were a heavy chain that stained with goat anti-human g chain $^{125}$I-labeled antibody, and two light chains that stained with goat anti-human k chain $^{125}$I-labeled antibody (Figure not shown).

The treatment of the original anti-KC-4 murine antibody with N-glycosidase F (Boehringer Mannheim GmbH Germany) following the recommendations of the manufacturer, produced a noticeable decrease in the intensity of the "top" light chain and a concomitant increase in the intensity of the bottom light chain (Figure not shown).

The explanation for the existence of an extra light chain is that this chain is glycosylated. Three lines of evidence substantiate this. First, the detection of an asparagine-linked glycosylation site in the amino acid sequence of the light chain. That is the triad NIS (Asn-Ile-Ser) in framework 3. Second, the decrease of the intensity in the putative glycosylated band after treatment with N-glycosidase F, while concomitantly the intensity of the non-glycosylated band was increased. Finally, 2 corresponding light chain bands are seen in the chimeric antibody version.

The extra light chain in the chimeric version cannot be a contaminant since it was specifically stained by goat anti-human k chain antibody. It can only be a product expressed by pAG4622. Thus both light chains must have the same $V_L$ amino acid sequence and the same human constant region. These observations show that approximately half of the light chains of both the anti-KC-4 murine and chimeric antibodies are glycosylated at the asparagine-linked glycosylation site.

Example 24
Amplification of cDNAs Encoding anti-KC-4 Antibody $F_v$ Regions

The cDNAs that encode the anti-KC-4 murine immunoglobulin $V_H$ and $V_L$ were prepared as described in Example 9 above from polyadenylated RNA isolated from 100 million KC-4 hybridoma cells. All clones were obtained from independent PCRs. The sequences of the primers are given in Example 19 and 20 above. All primers are specific for either the leader peptide region or for the constant regions. The primer combinations utilized herein are shown in Table 21 below.

TABLE 21

Primer Combination for PCR Amplifications

|  | Clone No. | Primer combinations |
|---|---|---|
| $V_L$ | 96 | MulgkV$_L$5'-C + MulgkV$_L$3'-1 |
|  | 107 | MulgkV$_L$5'-C + MulgkV$_L$3'-1 |
|  | K1 | JO20 + JO21 |
| $V_H$ | 66 | MulgV$_H$5'-F + MulggV$_H$3'-2 |
|  | 209 | MulgV$_H$5'-F + MulggV$_H$3'-2 |
|  | H3 | JO22 + JO24 |
|  | H7 | JO22 + JO24 |

Example 25
Isolation of Amplified anti-KC-4 $F_{VL}$ ($V_L$) and $F_{VH}$ ($V_H$) cDNA and Sequences The PCR products were cloned, without prior purification, into pCR1000 (Invitrogen) and sequenced in both directions. The $V_H$ and $V_L$ DNA sequences and their derived protein sequences are shown in Tables 22 and 23 below.

TABLE 22

$V_L$ Nucleotide Sequences
anti-KC-4 $V_L$ (kII-Jk2)

(Seq. ID No: 26)
ATG AAG TTG CCT GTT AGG CTG TTG GTG CTG ATG TTC

TGG ATT CCT GCT TCC AGC AGT GAT GTT TTG ATG ACC

CAA ACT CCT CTC TCC CTG CCT GTC AGT CTT GGA GAT

CAA GCC TCC ATC TCT TGC AGA TCT AGT CAG AGC ATT

GTA CAT AGT AAT GGA AAC ACC TAT TTA GAA TGG TAC

CTG CAG AAA CCA GGC CAG TCT CCA AAG CTC CTG ATC

TABLE 22-continued $V_L$ Nucleotide Sequences
anti-KC-4 $V_L$ (kII-Jk2)

TAC AAA GTT TCC ATC CGA TTT TCT GGG GTC CCA GAC

AGG TTC AGT GGC AGT GGA TCA GGG ACA GAT TTC ACA

CTC AAT ATC AGC AGA GTG GAG GCT GAG GAT CTG GGA

ATT TAT TAC TGC TTT CAA GGT TCA CAT GTT CCG TAC

ACG TTC GGA GGG GGG ACC AAG CTG GAA ATA AAA C

TABLE 23

$V_H$ Nucleotide Sequences
anti-KC-4 $V_H$ (IIID-D9-JH3)

(Seq. ID No: 27)
ATG GAC TTT GGG CTC AGC TTG GTT TTC CTT GTC CTT

ATT TTA AAA GGT GTC CAG TGT GAA GTG CAG ATG GTG

GAG TCT GGG GGA GTG AAG CCT GGA GGG TCC CTG AAA

CTC TCC TGT GCA GCC TCT GGA TTC GCT TTC AGT AGC

TAT GCC ATG TCT TGG GTT CGC CAG GAG AAG AGG CTG

GAG TGG GTC GCA GAA ATT AGT AGT GGT GGT AAT TAC

GCC TAC TAT CAA GAC ACT GTG ACG GGC CGA TTC ACC

AGA GAC AAT GCC AAG AAC ACC CTG TAC CTG GAA ATG

AGC AGT CTG AGG TCT GAG GAC ACG GCC ATG TAT TAC

TGT GCA AGG GAG GGT ATC CCG GCC TGG TTT GCT TAC

TGG GGC CAA GGG ACT CTG GTC TCT GTC TCT GCA G

Example 26
Amino Acid Sequences of anti-KC-4 Chimeric Antibody Fv Regions

After the anti-KC-4 $F_v$ region cDNAS were cloned, and sequenced, and their cDNA-derived amino acid sequence was compared with the N-terminus sequence directly determined by a single run of amino acid sequencing on purified anti-KC-4 antibody. The cDNA sequences were shown to be accurate since in both cases they were identical for clones that were prepared from independent reverse transcription reactions. This confirms that the cloned cDNAs are authentic anti-KC-4 $F_v$ regions. The sequences are shown in Tables 24 and 25 below.

TABLE 24

$V_L$ Amino Acid Sequences
anti-KC-4$V_L$(kII-Jk2)

| MKLPVRLLVLMFWIPASSS | (Seq. ID No: 28) |
|---|---|
| FR1 |  |
| DVLMTQTPLSLPVSLGDQASISC | (Seq. ID No: 29) |
| CDR1 |  |
| RSSQSIVHSNGNTYLE | (Seq. ID No: 30) |
| FR2 |  |
| WYLQKPGQSPKLLIY | (Seq. ID No: 31) |
| CDR2 |  |
| KVSIRFS | (Seq. ID No: 32) |
| FR3 |  |

TABLE 24-continued

V_L Amino Acid Sequences
anti-KC-4V_L(kII-Jk2)

| | |
|---|---|
| GVPDRFSGSGSGTDFTLNISRVEAEDLGIYYC | (Seq. ID No: 33) |
| CDR3 | |
| FQGSHVPYT | (Seq. ID No:34) |
| FR4 | |
| FGGGTKLEIK | (Seq. ID No. 35) |

TABLE 25

V_H Amino Acid Sequences anti-KC-4V_H (IIID-D9-JH3)

| | |
|---|---|
| MDFGLSLVFLVLILKGVQC | (Seq. ID No: 36) |
| FR1 | |
| EVQMVESGGGLVKPGGSLKLSCAASGFAFS | (Seq. ID No:37) |
| CDRI | |
| SYAMS | (Seq. ID No: 38) |
| FR2 | |
| WVRQSPEKRLEWVA | (Seq. ID No: 39) |
| CDR2 | |
| EISSGGNYAYYQDTVTG | (Seq. ID No: 40) |
| FR3 | |
| RFTISRDNAKNTLYLEMSSLRSEDTAMYYCAR | (Seq. ID No: 41) |
| CDR3 | |
| EGIPAWFAY | (Seq. ID No: 42) |
| FR4 | |
| WGQGTLVSVSA | (Seq. ID No: 43) |

The sequences were interpreted as described by Kabat et al. (1991), supra. The residues that are underlined correspond to PCR primers. The mature $V_L$ and $V_H$ chains begin at amino-acids D and E of framework 1 (FR1), respectively.

Framework and CDR protein segments were identified according to Kabat et al. (1991), supra. $V_L$ is a group II k chain. Part of the CDR 3 and all of the framework 4 (FR4) are encoded by Jk2. $V_H$ belongs to group IIId. CDR 3 and FR4 resulted from a genomic recombination involving minigenes D9 and JH3. There is an asparagine glycosylation site in the light chain in FR3. The site reads NIS (Asn Ile Ser).

Example 27
Comparison of cDNA-deduced Amino Acid Sequence with Directly Determined N-Terminal Fragment Sequence A comparison between the cDNA-derived polypeptide sequence and the amino acid sequence determined directly on the purified anti-KC-4 monoclonal antibody was undertaken. The results are shown in Table 26 below.

TABLE 26

Comparison of cDNA-deduced with Directly
Determined N-Terminal Amino Acid Sequences

FIRST BAND TOP

| | | |
|---|---|---|
| V_H, cDNA-deduced | EVQMVESGGGLVKPGGSLKLS | (Seq. ID No: 44) |
| V_H, Protein sequence | EVQMVESGGGLVKPGGXLKLS | (Seq. ID No: 45) |

SECOND BAND

| | | |
|---|---|---|
| V_L, cDNA-deduced | DVLMTQTPLSLPVSLGDQASI | (Seq. ID No: 46) |
| V_L, Protein sequence | DVLMTQTPLSLPVXXGDQASI | (Seq. ID No: 47) |

TABLE 26-continued

Comparison of cDNA-deduced with Directly
Determined N-Terminal Amino Acid Sequences

THIRD BAND

| | | |
|---|---|---|
| V_L, cDNA-deduced | DVLMTQTPLSLPVSLGDQASI | (Seq. ID No: 48) |
| V_L, Protein sequence | DVLMTQTPLSLPVSLGDQASI | (Seq. ID No: 49) |

X uncertain or alternative calls.

A sample of anti-KC-4 chimeric antibody (approximately 190 mg) was reduced with 5% beta-mercaptoethanol (65/C. for 15 min.), separated on three lanes of a 10% SDS polyacrylamide gel, and electroblotted onto a ProBlott membrane (Applied Biosystems, Foster City, Calif.) in 90% 30 mM CAPS pH11, 10% methanol, for 1 hour at 25 V and at 4/C. The transferred protein species were stained with Commassie Brilliant Blue. 3 bands were seen in each lane, of which 2 migrated as expected for a heavy and light chain. The third band migrated above the light chain. Amino acid sequencing was performed directly on the immobilized bands by the Biotechnology Instrumentation Facility, University of California, Riverside. The amino acid sequence given here is the sequencer's best guess.

Example 28
Construction of anti-KC-4 Murine-Human Chimeric Antibody Genes

The vector used were described in Example 1 above. Restriction ends were added to the cDNAs in a set of PCR reactions, using primers JO20, 21, 22, and 24.

The pAG4622 light chain vector and the pAH4604 heavy chain vector were described in Example 12 above.

The new $V_H$ and $V_L$ DNA fragments with appropriate restriction ends were integrated into pAH4604 and pAG4622 as described in Example 12 above. The vectors were then electroporated (together) also as described in Example 12 above.

Example 29
Tissue Binding Studies

The supernatants from stable transfectants were assayed for the presence of the anti-KC-4 murine-human chimeric antibody as described in Example 13 above. The chimeric antibody secreted in the supernatant bound both HMFG and BEM very strongly. In addition, the supernatants containing anti-KC- 4 murine-human chimeric antibody were used to stain human breast carcinoma tissue sections by using the immunoperoxidase immunohistochemical staining technique. The intensity of the staining was comparable to that obtained with the original murine monoclonal antibody. The anti-KC-4 monoclonal antibody is known to bind the human milk fat globule and the breast epithelial mucin. This binding specificity of the anti-KC-4 murine monoclonal antibody was maintained even after the recombinant procedure. The anti-KC-4 chimeric antibody bound very strongly to HMFG and BEM as determined by a radioassay (Ceriani, et al., Breast Cancer Res. Trent. 15:161 (1990)). In addition, the anti-KC-4 chimeric antibody bound several human breast tumors in histopathological sections in a manner comparable to the anti-KC-4 murine monoclonal antibody, as detected by immunostaining described in Example 15 above. This specificity of binding demonstrated the retained binding reactivity of the variable regions of anti-KC-4 murine antibody by the polypeptide of the invention when attached to the human $F_c$ fragment.

Example 30
Materials and Assays for Epitope Mapping

The specific details of the preparation of materials, cell lines, and techniques employed were disclosed by Peterson et al. (Peterson, J. A., et al., "Molecular Analysis of Epitope Heterogeneity of the Breast Mucin", Breast Epithelial Antigens, Ed. Ceriani, R. L., Plenum Press, NY (1991)), the relevant text of which is incorporated herein by reference.

Overlapping peptide hexamers were synthesized onto the ends of polyethylene pins using an Epitope Scanning Kit (Cambridge Research Biochemicals, Cambridge, UK), which is based on a method originally described by Geysen et al. (Geysen, H. L., et al., "Use of Peptide Synthesis to Probe Vital Antigens for Epitopes to a Resolution of a Single Amino Acid", PNAS (USA) 81:3998–4002 (1984)). The polyethylene pins were arranged in a 8×12 configuration that fits into a 96 well microtiter dish. The pins are supplied with an alanine attached to the ends to which the amino acids are added consecutively using pentafluorophenyl active esters of fluorophenyl-methyloxycarbonyl (Fmoc)-L-amino acids. Each consecutive overlapping hexamer differs from the previous one by a single amino acid and enough were synthesized to span the entire sequence of the peptide to be tested so that every combination of hexamer was present. Each monoclonal antibody was tested for binding to the synthetic peptides using an ELISA method with horseradish peroxidase-conjugated goat anti-murine IgG (Promega, Madison, Wis.) and color development with 2,2-azino-bis (3-ethylbenzothiazoline- 6-sulfonic acid (Sigma, St. Louis, Mo.).

The hexapeptides starting with A,P, D, and T bind well to the antibodies (Hexamers 1 to 3 and 20), whereas the hexamers starting between these positions did not. The hexamers that were prepared are shown in Table 27 below. The linear amino acid sequence essential for its binding to the antigen may be deduced from the hexamer that each monoclonal antibody binds. For example, the anti-BrE-3 antibody required the sequence TRP within the hexamer. Other monoclonal antibodies required other amino acid sequences (e.g., anti-Mc5, TRPAP; anti-Mc1, DTR; anti-BrE-1, DTRP). BrE-2 also required TRP but its different specificity for normal and tumor tissue indicates that its epitope on the native antigen is different from BrE-3.

TABLE 27

Epitope Mapping of Repeat Peptide Breast Mucin

```
              * *       *       * *                        *
Hexamer  G V T S A P D T R P A P G S T A P P A H G V T S    A P D T R P
1                P D T R P A
2                  D T R P A P
3                    T R P A P G
4                      R P A P G S
5                        P A P G S T
6                          A P G S T A
7                            P G S T A P
8                              G S T A P P
9                                S T A P P A
10                                 T A P P A H
11                                   A P P A H G
12                                     P P A H G V
13                                       P A H G V T
14                                         A H G V T S
15                                           H G V T S A
16                                             G V T S A P
17                                               V T S A P D
18                                                 T S A P D T
19                                                   S A P D T R
20                                                     A P D T R P
```

Example 31
Epitope Mapping

Five different monoclonal antibodies (Mc1, Mc5, BrE1, BrE2 and BrE3) were prepared using HMFG for immunization. All identified epitopes on the highly glycosylated large molecular weight breast mucin. By immunohistochemistry they appeared to recognize different epitopes since each had different tissue and tumor specificities (Peterson, J. A., et al., "Biochemical and Histological Characterization of Antigens Preferentially Expressed on the Surface and Cytoplasm of Breast Carcinomas Cells Identified by Monoclonal Antibodies Against the Human Milk Fat Globule", Hybridoma 9:221–235 (1990)). Each monoclonal antibody bound to a different spectrum of normal tissues and their specificities for different carcinomas were different. Anti-BrE2 and anti-BrE3, however, were quite similar. In addition, by screening breast Igtll cDNA expression libraries with some of these monoclonal antibodies, cDNA clones were isolated that produced fusion proteins that bound all of them, while other cDNA clones bound just some (Larroca, D., et al., "High Level Expression in E. coli of an Alternate Reading Frame of pS2 mRNA that Encodes a Mimotope of Human Breast Epithelial Mucin Tandem Repeat" Hybridoma 11(2): 191–201 (1992)). This binding to the fusion proteins indicated that the epitopes for these five monoclonal antibodies included the polypeptide portion of this glycoprotein. To confirm this the binding of these monoclonal antibodies to two synthetic polypeptide 20-mers (PDTRPAPGSTAPPAHGVTSA and APPAHGVTSAPDTRPAPGST) that spanned the tandem repeat consensus sequence was tested (Gendler, S. J., et al., "Cloning of Partial cDNA Encoding Differentiation and Tumor-Associated Mucin Glycoproteins Expressed by Human Mammary Epithelium", PNAS (USA) 84:6060–6064 (1987); Siddiqui, J., et al., "Isolation and Sequencing of a cDNA Coding for the Human DF3 Breast Carcinoma-Associated Antigen", PNAS (USA) 85:2320–2323 (1988)).

One was started at the beginning of the published 20 amino acid repeat (Gendler, S. J., et al. (1987), supra) unit, and the other was started in the middle. All five monoclonal antibodies bound to both synthetic peptides, as did DF3, a monoclonal antibody against breast carcinoma cells produced by others (Hull, S. R., et al., "Oligosaccharide Differences in the DF3 Sialomucin Antigen from Normal Human Milk and the BT-20 Human Breast Carcinoma Cell Line", Cancer Comm. 1:261–267 (1989)). Three other monoclonal antibodies against other components of the HMFG that do not cross-react with the breast mucin, Mc13, against a 70 KDa glycoprotein, and Mc3 and Mc8, against a 46 KDa glycoprotein do not bind to these synthetic peptides (data not shown) (Ceriani, R. L., et al., "Characterization of Cell Surface Antigens of Human Mammary Epithelial Cells with Monoclonal Antibodies Prepared Against Human Milk Fat Globule", Somat. Cell Genet. 9:415–427 (1982); Peterson, J. A., et al., "Biochemical and Histological Characterization of Antigens Preferentially Expressed on the Surface and Cytoplasm of Breast Carcinoma Cells Identified by Monoclonal Antibodies Against the Human Milk Fat Globule", Hybridoma 9:221–235 (1990)).

Example 32

Approach for Humanization of Antibodies

The present humanization approach is based on Padlan, E. A., "Choosing the Best Framework to Use in the Humanization of an Antibody by CDR-Grafting: Suggestions from 3-D Structural Data", Antibody Engineering 2nd. Annual Conf. San Diego, Calif. (Dec 16–17, 1991).

The fine specificity may be preserved in a "humanized" antibody only if the CDR structures, their interaction with each other, and their interaction with the rest of the variable domains can be maintained. (Padlan, E. A.(1991), supra). This requires the preservation of residues of the FR amino acids which contact the CDRs, those which are involved in the $V_L$-$V_H$ contact, and those which are buried and could influence the overall domain structure and the structure of the combining site.

By examination of murine Fab structures, for which atomic coordinates are available, the FR amino acids that are probably "important" in maintaining the structure of the combining site may be determined (Padlan, E. A., 8th International Congress of Immunol., Budapest, Hungary, Abstracts p. 19 (Aug. 2–28, 1992)).

The specificity of an antibody depends on the CDR structures and sometimes, on some of its neighboring residues as well. These CDR structures, in turn, depend on contacts with framework amino acids and on the interaction of the $V_L$ and $V_H$ domains. Thus, to ensure the retention of binding affinity, not only the CDR residues must be preserved, but also those FR residues that contact either the CDRs or their opposite domains, as well as all buried residues, which give shape to the variable domains. The buried amino acids are placed in exactly the same positions in human and in murine frameworks (Padlan, E. A., "A Possible Procedure for Reducing the Immunogenicity of Antibody Variable Domains While Preserving Their Ligand-Binding Properties", Molecular Immunology 28:489–498 (1991)).

This approach was applied to design humanized analogues of the variable regions of the murine antibodies of the invention. The humanization or design of the exemplary analogue peptide provided herein was undertaken as follows. The identification of the residues, which are most probably "important" in preserving the combining site structure, permits the selection of the best human FR sequences to use in the "humanization" of each chimeric antibody of known structure or analogues peptides of the invention. The results of the analysis can be used also to predict which FR amino acids should probably be retained in those cases where no three-dimensional structural data are available.

The present procedure was designed to reduce the immunogenicity of the xenogeneic antibodies by preparation of their chimeric derivatives or fragments thereof while preserving their antigen-binding properties. In general, the antigen binding properties of an antibody are primarily determined by its CDRs. The CDRs of the murine antibody were "grafted" herein onto a human framework. In addition, the FR amino acids in the antibody, that are judged as probably important in maintaining the combining-site structure, may also be retained in the humanized molecule.

Example 33

Choice of a Murine Model of Known Structure for the Humanization of the BrE-3 Antibody The classification of the $V_H$ and $V_L$ domains of an antibody such as the anti-BrE-3 antibody was done according to Kabat, E. A., et al. (Kabat, E. A., et al., "Sequences of Proteins of Immunological Interest" NIH (1991). The anti-BrE-3 kappa chain $V_L$ domain belongs to group II and the $V_H$ domain belongs to group IIIc. A murine antibody was then found, whose structure had been determined, and whose variable regions belong to the same classes. The anti-fluorescyl murine antibody 4-4-20 shown in Table 1 above (Herron, J. N., et al., "Three-Dimensional Structure of a Fluorescein-Fab Complex Crystallized in 2-Methyl-2,4-Pentanediol", Proteins, 5:271–280 (1989) fits these requirements since, like BrE-3, it has $V_L$ and $V_H$ domains belonging to groups II and IIIC. Thus, the three-dimensional structures of antibodies BrE-3 and 4-4-20 should be similar, and BrE-3 may be modeled after 4-4-20.

Example 34

Choice of Target Human Framework for Humanization of BrE-3 Antibody

The choice of the target human framework was not based on the similarity of the amino acid sequence of the entire framework, but strictly on the similarity at the residues that were judged to be structurally important according to the 4-4-20 model. That is, only amino acids that could be involved in contacts with CDR of the opposite chain, or amino acids whose side-chains were predicted to be inwardly pointed. The positions of these amino acids are shown in Tables 8 and 9 and also in Tables 2, 3, 4, 5 and 6 above. These positions are as follows.

For the light chain variable region framework: 1, 2, 3, 4, 5, 6, 11, 13, 19, 21, 23, 35, 36, 37, 38, 44, 45, 46, 47, 48, 49, 58, 60, 61, 62, 69, 71, 73, 75, 78, 82, 86, 88, 98, 102, and 104.

For the heavy chain variable region framework: 4, 6, 12, 18, 20, 22, 24, 27, 28, 29, 30, 36, 37, 38, 39, 40, 45, 46, 47, 48, 49, 66, 67, 68, 69, 71, 73, 76, 78, 80, 82c, 86, 88, 90, 91, 92, 93, 94, 103, 107, 109 and 111.

The numbering system is conventionally accepted (Kabat, et al. (1991), supra) and shown in Tables 10 and 11 above. In this case, the consensus sequences of all human $F_v$ regions were selected as the target human framework to minimize the immunogenicity of the product.

First, the sequences of the murine variable chains were aligned with consensus sequences from all known human variable region classes (Herron, J. N., (1989), supra) and the number of differences in the amino-acids that must be retained from the murine were scored. The positions of these amino acids were obtained from those of murine monoclonal antibody 4-4-20, which was chosen to model the anti-BrE-3 antibody as shown in Tables 28 and 29 below.

TABLE 28

Choice of BrE-3 $V_L$ Target Human Framework
BrE-3 $V_L$

```
                                        CDR1                              CDR2
               ******   * *    * * *                    ****       ******
BRE3K     DVVMTQTPLSLPVSLGDQASISC RSSQNLVHN-NGNTYLY WFLQKSGQSPKLLIY RASIRFS
HuKi-n    .IQ...S.S..SA.V..RVT.T. .A...S..XXS-ISN..A .YQ..P.KA...... A...SLE.
HuKii-nt .I....S.....TP.EP...... ...S.L.SXD......N .Y...P....Q.... LV.N.A.
HuKiii    EI.L..S.GT.SL.P.ER.TL.. .A...SVSSS.-----.A .YQ..P...A.R.... G...S.AT
HuKiv     .I....S.D..A....ER.T.N. K...SVLYSS.NKN..A .YQ..P...P...... W...T.E.

CDR3
               * ***       * * * *  *   *   * *                *     * *
BRE3K     GVPDRFSGSGSETDFTLKISRVEAEDLGVYFC FQGTHVPW-T FGGGTKLEIK
HuKi-n    ...S........G.....T..SLQP..FAT.Y. Q.YNSL.EW. ..Q...V...
HuKii-nt
          ...........G................V...Y. M.ALQX.RX. ..Q...V...
HuKiii    .I..........G.....T...L.P..FA..Y. Q.YGSS.PL. ..Q...V...
HuKiv
          ...........G.....T..SLQ...VA..Y. Q.YYST.-X. ..Q...V...
```

. identity with the murine sequence
\* the murine residues that are structurally important.

TABLE 29

Choice of BrE-3 $V_H$ Target Human Framework
BrE-3$V_H$

```
                                                     CDR1
               * *     *      * * * *  ****                 *****  *****
BRE3VH   EVKLEESGGGLVQPGGSMKLSCAASGFTFS  DAWMD--  WVRQSPEKGLEWVA
HuHI     Q.Q.VQ..AEVKK..A.V,V..K...Y..T  SYAIS--  ....A.GQ....MG
HuHII    Q.Q.Q...P...K.SQTLS.T.TV..GSV.  SYXWSWN  .I..P.G.....IG
HuHIII   ..Q.V............LR...........  SYA.S--  ....A.G......S

CDR2                    **** * *  * * * *   *    *  ****
BRE3VH   IRNKANNHATYYDESVKG RFTISRDDSKSRVYLQMISLRAEDTGLYYCTG
HuHI     W.N-PYG.GD.N.AQKFQ. .V..TA.T.T.TA.MELS.......AV...AR
HUHII    R.YYR.YSGS.X.NP.L.S .V...V,T..NQFS.KLS.VT.A..AV...AR
HuHIIIV  .SG.TDGGS...AD.... .......N..NTL....N.......AV...AR

CDR3             *   * * *
BRE3VH   EF---------------AN WGQGTLVTVSA
HuHI     APGYGSGGGCYRGDYXFDY ..........S
HuHII    ELPGGYXGDDYYYXXGFDV ..........S
HuHIII   GRXGXSLSGXYYYYHYFDY ..........S
```

. identity with the murine sequence
\* the murine residues that are structurally important.

Based on these scores, the human frameworks belonging to groups $V_K$II and VH$_K$III were chosen to receive the anti-BrE-3 CDRs plus other important amino acids.

Example 35

Identification of BrE-3 Murine-Human Differences

The original murine sequences (BrE-3 $V_K$ or $V_H$) were aligned with their closest human (Human KII or HIII) relatives that were chosen after comparing their sequences in Table 28 above. The alignment of these two sequences is shown in Table 30 below. The information in this table is also contained in Table 28 above, but is reproduced here for clarity. The CDRs are not shown, since their sequences were not changed during the humanization process. Thus, Table 30 shows the maximum number of amino acids that can be changed toward the humanization of the anti-BrE-3 antibody, based on the consensus human sequences obtained from the current databases (Kabat, E. A., et al. (1991), supra). If all these positions were to be replaced with the corresponding human amino acids, the corresponding CDR grafted antibody variable regions would be attained.

TABLE 30

Corresponding Amino Acid Sequences of VK BrE-3 and Human KII

```
                                    CDR1                    CDR2
BrE-3 VK   DVVMTQTPLSLPVSLGDQASISC --------------- WFLQKSGQSPKLLIY ------
Human KII  .I....S.....TP.EP......  --------------- .Y...P....Q.... ------

CDR3
BrE-3 VK   GVPDRFSGSGSETDFTLKISRVEAEDLGVYFC ---------- FGGGTKLEIK
Human KII
...........G..............V...Y.  ----------  ..Q...V...

CDR1
BrE-3 VH   EVKLEESGGGLVQPGGSMKLSCAASGFTFS ----- WVRQSPEKGLEWVA
Human III  ..Q.V...........LR............ ----- ....A.G......S CDR2
BrE-3 VH   ------------------  RFTISRDDSKSRVYLQMISLRAEDTGLYYCTG
Human III  ---------------------....  ...N..NTL....N.......AV...AR CDR3
BrE-3 VH   --------------------  WGQGTLVTVSA
Human III  ------------------------.......  ..S
```

Table 31 and 32 below contain the same information as Table 30 above in a different format. They show the numbers of the residues that would have to be changed in order to completely convert the original murine framework completely into a human consensus framework.

TABLE 31

BrE-3 $V_L$ Amino Acid Candidates for Change into Human Consensus Sequences

| $V_L$ | | | |
|---|---|---|---|
| VI2 | FY36 | EG68 | GQ100 |
| TS7 | SP40 | LV83 | LV104 |
| ST14 | KQ45 | FY87 | LP15 |
| DE17 | | | |
| QP18 | | | |

TABLE 32

BrE-3 $V_H$ Amino Acid Candidates for Change into Human Consensus Sequences

| $V_H$ | | |
|---|---|---|
| KQ3 | SA40 | DN73 |
| AS113 | EV5 | EG42 |
| SN76 | ML18 | AS49 |
| RT77 | KR19 | VL78 |
| N82a | GA88 | LV89 |
| | | TA93 |
| | | GR94 |

Example 36
Identification of Important Murine BrE-3 Amino Acids

The "important" murine amino acids that should be preserved were chosen based on the contacts of a particular amino acid with the CDRs, and with the opposite chains and/or whether their side chains are pointing inwardly or outwardly. The positions of these "important" amino acids were determined based on the examination of the known structures of other antibodies. This information is provided in Tables 33 and 34 below.

TABLE 33

Important $V_L$ Amino Acid Positions to be Preserved

| $V_L$ | | |
|---|---|---|
| V2 | CDR contact | Buried |
| F36 | CDR contact | Contact with VH |
| K45 | CDR contact | |
| F87 | Possible contact with VH | |
| G100 | Possible contact with VH | |
| L104 | Buried | |

TABLE 34

Important $V_H$ Amino Acid Positions to be Preserved

| $V_H$ | | |
|---|---|---|
| M18 | Buried | |
| S40 | Buried | |
| A49 | CDR contact | Buried |
| D73 | CDR contact | |
| S76 | | Buried |
| V78 | CDR contact | Buried |
| L89 | Might affect interaction with $V_L$ | |
| T93 | CDR contact | |
| G94 | CDR contact | Buried |

Most of the "important" amino acids were selected on the basis of the structure of antibody 4-4-20 and according to Tables 2, 3, 4, 5, 6, 8 and 9 above. Two important amino acids out of each chain, however, were selected based on more general structural analysis, using other antibody structures. This was done to maximize the chances of conserving ligand binding properties. In particular the preservation of the Leu at 89-H was suggested in order to ensure the maintenance of, the $V_L:V_H$ contact. Although the residue aat 89-H is usually not in contact with $V_L$ and is only partly buried, it nonetheless contributes to the interface. A Val for Leu replacement at this position could very well create a "cavity" which could affect the contact. An Ile for Leu replacement would probably be fine since these amino acids have essentially the same side chain volume.

Finally, by comparing the position of all amino acids that are candidates for mutation, shown in Tables 31 and 32 above, with those that are "important" and should be preserved, shown in Tables 33 and 34, the final selection of amino acid positions for actual mutation was attained. Any "important" amino acid position was eliminated from the list of candidates. Table 35 below shows the amino acids that were selected for change from murine to human identities to obtain the present humanized analogue.

TABLE 35

Selected Amino Acids for Mutation

| $V_L$ | $V_H$ |
|---|---|
| TS7 | KQ3 |
| ST14 | EV5 |
| LP15 | KR19 |
| DE17 | EG42 |
| QP18 | RT77 |
| SP40 | IN82a |
| EG68 | GA88 |
| LV83 | AS113 |

Example 37

Introduction of Changes in BrE-3 Amino Acid Sequence

The changes were done at the DNA level in sequential manner. All but one of the codon mutations were performed using enzymatic inverse PCR (EIPCR), a mutagenesis technique developed by Stemmer and Morris (Stemmer, W. P. C and Morris, S. K., "Enzymatic Inverse Polymerase Chain Reaction: a Restriction Site Independent, Single Fragment Method for High Efficiency Site-Directed Mutagenesis", BioTechniques 13:146–220 (1992)).

First, the entire plasmid, containing the target cDNA was amplified by inverse PCR using terminal mutagenic oligonucleotides. Second, BsaI was used to cut the ends of the incorporated primers. This enzyme cuts at a site that is displaced from its recognition site. Thus, after digestion of the open amplified plasmid with BsaI, the BsaI recognition sequence was removed from the ends of the DNA. The DNA was left with complementary sticky ends and could be closed into a functional plasmid that contains the mutagenized region. The amino acid and DNA sequences of the non-mutated (wild-type) variable light and heavy chains of the anti-BrE-3 antibody are shown in Tables 15 and 16 above. The amino acid sequences of the anti-BrE-3 antibody frameworks and the mutations that were performed for the humanization, the oligonucleotide that was used for the mutagenesis, and the method of mutagenesis are shown in Tables 36 to 44 below.

TABLE 36

$F_{VL}$ FR1 Mutation Sites

| Position | FR1 | Analogue 1 (8 Changes) | DNA Codon (FR1) (Analogue) | Method for Mutagenesis | Primers |
|---|---|---|---|---|---|
| Leader Peptide Not Shown | | | | | |
| | D | | | | |
| | V | | | | |
| | V | | | | |
| | M | | | | |
| | T | | | | |
| | Q | | | | |
| 7 | T | S | ACT TCT | EIPCR* | (JO37, JO38) |
| | P | | | | |
| | L | | | | |
| | S | | | | |
| | L | | | | |
| | P | | | | |
| | V | | | | |
| 14 | S | T | AGT ACT | EIPCR | (JO37, JO38) |
| 15 | L | P | CTT CCT | EIPCR | (JO37, JO38) |
| | G | | | | |
| 17 | D | E | GAT GAG | EIPCR | (JO37, JO38) |
| 18 | Q | P | CAA CCA | EIPCR | (JO37, JO38) |
| | A | | | | |
| | S | | | | |
| | I | | | | |
| | S | | | | |
| | C | | | | |

*EIPCR: Enzymatic Inverse Polymerase Chain Reaction

TABLE 37

$F_{VL}$ FR2 Mutation Sites

| Position | FR2 | Analogue 1 (8 Changes) | DNA Codon (FR2) (Analogue) | Method for Mutagenesis | Primers |
|---|---|---|---|---|---|
| CDR1 Not Shown | | | | | |
| | W | | | | |
| | F | | | | |
| | L | | | | |
| | Q | | | | |
| | K | | | | |
| 40 | S | P | TCA CCA | EIPCR* | (JO39, JO40) |
| | Q | | | | |
| | S | | | | |
| | P | | | | |
| | K | | | | |
| | L | | | | |
| | L | | | | |
| | I | | | | |
| | Y | | | | |

*EIPCR: Enzymatic Inverse Polymerase Chain Reaction

TABLE 38

$F_{VL}$ FR3 Mutation Sites

| Position | FR3 | Analogue 1 (8 Changes) | DNA Codon (FR3) (Analogue) | Method for Mutagenesis | Primers |
|---|---|---|---|---|---|
| CDR2 Not Shown | | | | | |
| | G | | | | |

TABLE 38-continued

$F_{VL}$ FR3 Mutation Sites

| Position | FR3 | Analogue 1 (8 Changes) | DNA Codon (FR3) (Analogue) | Method for Mutagenesis | Primers |
|---|---|---|---|---|---|
|  | V |  |  |  |  |
|  | P |  |  |  |  |
|  | D |  |  |  |  |
|  | R |  |  |  |  |
|  | F |  |  |  |  |
|  | S |  |  |  |  |
|  | G |  |  |  |  |
|  | S |  |  |  |  |
|  | G |  |  |  |  |
|  | S |  |  |  |  |
| 68 | E | G | GAG GGG | EIPCR* | (JO41,JO42) |
|  | T |  |  |  |  |
|  | D |  |  |  |  |
|  | F |  |  |  |  |
|  | T |  |  |  |  |
|  | L |  |  |  |  |
|  | K |  |  |  |  |
|  | I |  |  |  |  |
|  | S |  |  |  |  |
|  | R |  |  |  |  |
|  | V |  |  |  |  |
|  | E |  |  |  |  |
|  | A |  |  |  |  |
|  | E |  |  |  |  |
|  | D |  |  |  |  |
| 83 | L | V | CTG GTG | EIPCR | (JO41,JO42) |
|  | G |  |  |  |  |
|  | V |  |  |  |  |
|  | Y |  |  |  |  |
|  | F |  |  |  |  |
|  | C |  |  |  |  |

*EIPCR: Enzymatic Inverse Polymerase Chain Reaction

TABLE 39

$F_{VL}$ FR4 Mutation Sites

| Position | FR4 | Analogue 1 (10 Changes) | Analogue 2 (6 Changes) | DNA Codon (FR4) (Analogue) | Method for Mutagenesis | Primers |
|---|---|---|---|---|---|---|
| CDR3 Not Shown |  |  |  |  |  |  |
|  | F | F |  |  |  |  |
|  | G | G |  |  |  |  |
|  | G | G |  |  |  |  |
|  | G | G |  |  |  |  |
|  | T | T |  |  |  |  |
|  | K | K |  |  |  |  |
|  | L | L |  |  |  |  |
|  | E | E |  |  |  |  |
|  | I | I |  |  |  |  |
|  | K | K |  |  |  |  |

TABLE 40

$F_{VH}$ FR1 Mutation Sites

| Position | FR1 | Analogue 1 (8 Changes) | DNA Codon (FR1) (Analogue) | Method for Mutagenesis | Primers |
|---|---|---|---|---|---|
| Leader Peptide Not Shown |  |  |  |  |  |
|  | E |  |  |  |  |
|  | V |  |  |  |  |
| 3 | K | Q | AAG CAG | EIPCR* | (JO57,JO58) |
|  | L |  |  |  |  |
| 5 | E | V | GAG GTG | EIPCR | (JO57,JO58) |
|  | E |  |  |  |  |

TABLE 40-continued

F_VH FR1 Mutation Sites

| Position | FR1 | Analogue 1 (8 Changes) | DNA Codon (FR1) (Analogue) | Method for Mutagenesis | Primers |
|---|---|---|---|---|---|
|  | S |  |  |  |  |
|  | G |  |  |  |  |
|  | G |  |  |  |  |
|  | G |  |  |  |  |
|  | L |  |  |  |  |
|  | V |  |  |  |  |
|  | Q |  |  |  |  |
|  | P |  |  |  |  |
|  | G |  |  |  |  |
|  | G |  |  |  |  |
|  | S |  |  |  |  |
|  | M |  |  |  |  |
| 19 | K | R | AAA AGA | EIPCR | (JO57,JO58) |
|  | L |  |  |  |  |
|  | S |  |  |  |  |
|  | C |  |  |  |  |
|  | A |  |  |  |  |
|  | A |  |  |  |  |
|  | S |  |  |  |  |
|  | G |  |  |  |  |
|  | F |  |  |  |  |
|  | T |  |  |  |  |
|  | F |  |  |  |  |
|  | S |  |  |  |  |

*EIPCR: Enzymatic Inverse Polymerase Chain Reaction

TABLE 41

F_VH FR2 Mutation Sites

| Position | FR2 | Analogue 1 (8 Changes) | DNA Codon (FR2) (Analogue) | Method for Mutagenesis | Primers |
|---|---|---|---|---|---|
| CDR1 Not Shown |  |  |  |  |  |
|  | W |  |  |  |  |
|  | V |  |  |  |  |
|  | R Q |  |  |  |  |
|  | S |  |  |  |  |
|  | P |  |  |  |  |
| 42 | E | G | GAG GGG | EIPCR* | (JO55,JO56) |
|  | K |  |  |  |  |
|  | G |  |  |  |  |
|  | L |  |  |  |  |
|  | E |  |  |  |  |
|  | W |  |  |  |  |
|  | V |  |  |  |  |
|  | A |  |  |  |  |

*EIPCR: Enzymatic Inverse Polymerase Chain Reaction

TABLE 42

F_VH FR3 Mutation Sites

| Position | FR2 | Analogue 1 (8 Changes) | DNA Codon (FR2) (Analogue) | Method for Mutagenesis | Primers |
|---|---|---|---|---|---|
| CDR2 Not Shown |  |  |  |  |  |
|  | R |  |  |  |  |
|  | F |  |  |  |  |
|  | T |  |  |  |  |
|  | I |  |  |  |  |
|  | S |  |  |  |  |
|  | R |  |  |  |  |
|  | D |  |  |  |  |

TABLE 42-continued

F_VH FR3 Mutation Sites

| Position | FR2 | Analogue 1 (8 Changes) | DNA Codon (FR2) (Analogue) | Method for Mutagenesis | Primers |
|---|---|---|---|---|---|
|  | D |  |  |  |  |
|  | S |  |  |  |  |
|  | K |  |  |  |  |
|  | S |  |  |  |  |
| 77 | R | T | AGA ACT | EIPCR* | (JO53,JO54) |
|  | V |  |  |  |  |
|  | Y |  |  |  |  |
|  | L |  |  |  |  |
|  | Q |  |  |  |  |
|  | M |  |  |  |  |
| 82 | I | N | ATA AAT | EIPCR | (JO53,JO54) |
|  | S |  |  |  |  |
|  | L |  |  |  |  |
|  | R |  |  |  |  |
|  | A |  |  |  |  |
|  | E |  |  |  |  |
|  | D |  |  |  |  |
|  | T |  |  |  |  |
| 88 | G | A | GGC GCC | EIPCR | (JO53,JO54) |
|  | L |  |  |  |  |
|  | Y |  |  |  |  |
|  | Y |  |  |  |  |
|  | C |  |  |  |  |
|  | T |  |  |  |  |
|  | G |  |  |  |  |

*EIPCR: Enzymatic Inverse Polymerase Chain Reaction

TABLE 43

F_VH FR4 Mutation Sites

| Position | FR2 | Analogue 1 (8 Changes) | DNA Codon (FR2) (Analogue) | Method for Mutagenesis | Primers |
|---|---|---|---|---|---|
| CDR3 Not Shown |  |  |  |  |  |
|  | W |  |  |  |  |
|  | G |  |  |  |  |
|  | Q |  |  |  |  |
|  | G |  |  |  |  |
|  | T |  |  |  |  |
|  | L |  |  |  |  |
|  | V |  |  |  |  |
|  | T |  |  |  |  |
|  | V |  |  |  |  |
|  | S |  |  |  |  |
| 113 | A | S | GCA TCT | PCR+ | (JO51,-JO52)* |

+*PCR: Polymerase Chain Reaction

TABLE 44

Sequences of Mutagenic Oligonucleotides

| | | |
|---|---|---|
| JO37 | TCC CTG GGT CTC ACT CCT GGA GAG CCA GCT TCC ATC TCT TGC AGA TCT AGT | (Seq. ID No. 50) |
| JO38 | AGC TTG GGT CTC AGG AGT GAC AGG CAG GGA GAG TGG AGA TTG GGT CAT CAC AAC | (Seq.ID No. 51) |
| JO39 | G TTC CTG GTC TCG CCA GGC CAG TCT CCA AAG CTC CTG | (Seq. ID No. 52) |
| JO40 | T TGG AGG TCT CCC TGG CTT CTG CAG GAA CCA ATA TAA AT | (Seq. ID No. 53) |
| JO41 | TTC ACA GGT CTC ATC AGC AGA GTG GAG GCT GAG GAT GTG GGA GTT TAT TT | (Seq. ID No. 54) |
| JO42 | AGC CTC GGT CTC GCT GAT CTT GAG TGT GAA ATC TGT CCC TGA TCC ACT GC | (Seq. ID No. 55) |
| JO51 | CCT GGA GGA TCC ATG AGA CTC TCT TGT GCT | (Seq. ID No. 56) |
| JO52 | GTT GGG GCT AGC AGA AGA GAC AGT GAC CAG AGT | (Seq. ID No. 57) |
| JO53 | TAC CTG GGT CTC AAT AGC TTA AGA GCT GAA GAC ACT GCC CTT TAT TAC TGT | (Seq. ID No. 58) |
| JO54 | TTC AGC GGT CTC GCT ATT CAT TTG CAG GTA CAC AGT ACT TTT GGA ATC ATC | (Seq. ID No. 59) |
| JO55 | GTC CGC GGT CTC CCA GGG AAG GGG CTT GAG TGG GTT GCT GAA ATT AGA AA | (Seq. ID No. 60) |
| JO56 | CTC AAG GGT CTC CCC TGG AGA CTG GCG GAC CCA GTC CAT CCA GGC ATC A | (Seq. ID No. 61) |
| JO57 | T GAG GAG GTC TCA GGA GGC TTG GTG CAA CCT GGA GGA TCC ATG AGA CTC TCT | (Seq. ID No. 62) |
| JO58 | GG TTG CGG TCT CCC TCC TCC AGA CTC CAC AAG CTG CAC TTC ACT CTG GAC A | (Seq. ID No. 63) |

* note Primer set JO51 and JO52 was originally intended for mutagenizing K19 to R (by J051) and A113 to S (by JO52), as described below. Primer JO51, however, was somehow defective (It did not run as a single band on a polyacrylamide gel) and thus only the A113 to S mutagenesis was successful. Mutation K19 to R was accomplished at a latter time with EIPCR, using primers JO57 and JO58.

Example 38

Synthesis of Primers

All primers except JO51 and JO52 were synthesized on a PCR-Mate EP DNA synthesizer model 391 (Applied Biosystems, Foster City Calif.). Primers JO51 and JO52 were purchased from Keystone Laboratories, Inc, Menlo Park, Calif. Both, the PCR method used with JO51 and JO52 and the EIPCR method used with all other primer sets, are described below.

The plasmid DNA template was extracted with a kit purchased from QIAGEN (Tchapsworth, Calif.) and diluted to 1 ng/ml in 10 mM TRIS 1 mM EDTA pH 7.5–8. This plasmid is composed of vector pCR1000 (Invitrogen Corporation, San Diego, Calif.) into which the cDNA encoding the variable region to be humanized was inserted.

A mixture of PCR primers was made where each primer was present at a concentration of 10 pmole/ml in water.

The PCR amplification conditions were as follows. All reagents as well as the GeneAmp PCR system 9600 were purchased from Perkin Elmer Cetus. Optimal PCR conditions were determined empirically for each pair of mutagenic primers. A matrix of conditions varying the concentration of $MgCl_2$, mutagenic primers, and template plasmid DNA was set up. The annealing and extension temperatures during PCR may be varied.

Plasmid template (500 pg/ml), 0.5 mM each mutagenic oligonucleotide, 1 mM $MgCl_2$, 10 mM 40 TRIS pH 8.3, 50 mM KCl, 0.2 mM each nucleotide triphosphate (dGTP, dATP, TTP, dCTP), and Taq polymerase 1 unit/20ml reaction mixture.

Example 39

Hot Start PCR

All the components of the PCR mixture, with the exception of Taq polymerase, were mixed in a 95 ml volume. The mixture was then dispensed in 19 ml aliquots into 5 PCR tubes. The reason for performing five independent reactions was to decrease the odds that unwanted mutations be isolated as a result of nucleotide misincorporation during PCR. The tubes were heated to 95° C. for 5 minutes and then cooled to 72° C. While at that temperature 1 ml of an appropriate Taq polymerase dilution in 10 mM TRIS, pH 8.3, 50 mM KCl was added to the reaction tubes. The temperature cycling then proceeded as follows.

94° C., 3 min 3 cycles 25 cycles

72° C., 10 min

Example 40

Extra Final Extension

After cycling, the contents of the five tubes were mixed and an extra final extension reaction was carried out. Extra nucleotide triphosphates were added (to 125 mM), 5 units of Taq polymerase were also added and the mixture was heated to 72° C. for 10 minutes.

Example 41

Purification of PCR Products

The PCR products were then separated on a 0.8% agarose gel in 1×TAE buffer and 0.5 mg/ml Ethidium Bromide. The correct DNA band was visualized with UV light (366 nm), excised from the gel and extracted with the GeneClean kit purchased from Bio 101, La Jolla, Calif.

Example 42

Restriction Digestion

The DNA was then digested with BsaI for two hours at 60 degrees celsius in 25 ml (20.5 ml of DNA, 2.5 ml 10×buffer 4 (NEB) and 2 ml BsAl (NEB). BsaI sites were designed near the 5'end of the PCR primers. The primers included 6 extra nucleotides 5'of the BsaI sites to facilitate digestion by BsaI. There were no BsaI sites elsewhere in the plasmid. Other restriction enzymes may be used as advised by Stemmer and Morris (Stemmer and Morris (1992), supra). This special class of restriction enzyme cuts at a site that is different from its recognition site but, nevertheless, at a precise distance from it. Using this method, there was no need for having restriction sites in the sequence in order to perform the mutagenesis.

Example 43
Second Purification

The restricted products were then separated on a 0.8% agarose gel in 1×TAE buffer and 0.5 mg/ml Ethidium Bromide. The correct DNA band was visualized with UV light (366 nm), excised from the gel and extracted with the GeneClean kit purchased from Bio 101, La Jolla, Calif.

Example 44
Ligation (Reclosure of Plasmid)

The ligation mixtures consisted of 5 ml extracted DNA, 2 ml 10×ligation buffer (NEB) 1 ml T4 DNA polymerase (NEB), 12 ml water. The amount of plasmid DNA may be varied depending of the intensity of the band extracted from the Gel. Ligation was carried out at room temperature for 2 hrs., or alternatively at 14° C. overnight.

Example 45
Transformation and Sequencing

The reclosed plasmids were then transformed into E. coli. We used Inv alpha F' competent cells purchased from Invitrogen Corporation, San Diego Calif.

Plasmid DNA was then prepared from a few transformants and sequenced to verify that mutagenesis was successful.

Example 46
Mutagenesis of BrE-3 Antibody using JO51 and JO52

These oligonucleotides were designed to mutagenize K19 to R (by JO51) and A113 to S (by JO52), not by using EIPCR but using the normal PCR (with primers pointing to each other). Primer JO51 carried a BamHI site and primer JO52 carried an NheI site. After mutagenic PCR amplification the resulting amplified DNA cassette was inserted into the plasmid in lieu of the corresponding wild-type DNA fragment. There was no compelling reason to use this method over the EIPCR method except that conveniently placed restriction sites (BamHI and NheI) were available.

This method, however, yielded only the A113 to S mutation. A subsequent analysis showed that the JO51 primer, which carried the K19 to R mutation ran aberrantly on a polyacrylamide gel.

The protocol for the mutagenic amplification step was as follows. Plasmid template (500 pg/ml), 0.75 mM each mutagenic oligonucleotide, 2 mM $MgCl_2$, 10 mM TRIS pH 8.3, 50 mM KCl, 0.2 mM each nucleotide triphosphate (dGTP, dATP, TTP, dCTP), and Taq polymerase 1 unit/20 ml reaction mixture.

The PCR was hot started as described for EIPCR above. The temperature cycling conditions used were as follows.

94° C., 3 min 3 cycles 32 cycles

72° C., 10 min

The extra final extension and purification of PCR products were conducted as described for EIPCR above.

The restriction digestion of the vector and the insert were conducted as follows. The PCR product was digested with BamHI and NheI for 1 hr. 50 min. at 37° C. (19 ml of DNA, 2.5 ml 10×buffer (NEB), 1.5 ml BamHI (NEB), 1.5 ml NheI (NEB). The vector, which is the starting plasmid described above, was digested under similar conditions.

The restricted products, vector and insert, were then purified once more as described above for EIPCR.

The ligation of the fragments was conducted as follows. The ligation mixtures consisted of 5 ml vector, 5 ml insert, 2 ml 10×ligation buffer (NEB) 1 ml T4 DNA polymerase (NEB), 7 ml water. The amount of plasmid DNA may be varied depending of the intensity of the band extracted from the Gel. Ligation is carried out at 14° C. overnight. A control ligation with vector only was carried out in parallel. The transformation of the host cells was conducted as described for EIPCR.

Example 47
Plasmid Preparation and Sequencing of Humanized BrE-3 $V_H$

Plasmid DNA was then prepared from several independent transformants. A few of the plasmids that were shown by restriction analysis to contain the insert were then sequenced to verify that the mutagenesis was successful. When one of the sequenced DNAs contained the desired mutation it was utilized for the next mutation cycle. The fully mutated humanized analogue BrE-3 DNA sequences for the $V_H$ and $V_L$ segments are shown in Tables 45 and 46 below.

TABLE 45

BrE-3 Antibody $V_L$ Humanized AnaloguE DNA Sequences
BrE-3 $V_L$FR-HZ (Seq. ID No. 64)

ATG AAG TTG CCT GTT AGG CTG TTG GTG CTG TTG TTC TGG ATT CCT GCT TCC ATC AGT GAT GTT GTG ATG ACC CAA

TCT CCA CTC TCC CTG CCT GTC <u>ACT</u> <u>CCT</u> GGA <u>GAG</u> <u>CCA</u> GCT TCC ATC TCT TGC AGA TCT AGT CAG MC CTT GTA CAC

AAC AAT GGA AAC ACC TAT TTA TAT TGG TTC CTG CAG AAG <u>CCA</u> GGC CAG TCT CCA AAG CTC CTG ATT TAT AGG GCT

TCC ATC CGA TTT TCT GGG GTC CCA GAC AGG TTC AGT GGC AGT GGA TCA <u>GGG</u> ACA GAT TTC ACA CTC AAG ATC

AGC AGA GTG GAG GCT GAG GAT <u>GTG</u> GGA GTT TAT TTC TGC TTT CAA GGT ACA CAT GTT CCG TGG ACG TTC GGT

GGA GGC ACC AAG CTG GAA ATC AAA C

TABLE 46

BrE-3 Antibody VH Humanized Analogue DNA Sequences
BrE-3 VH FR-HZ (Seq ID No.: 65)

ATG TAC TTG GGA CTG AAC TAT GTC TTC ATA GTT TTT CTC TTA AAA GGT GTC CAG AGT GAA GTG <u>CAG</u> CTT <u>GTG</u> GAG

TCT GGA GGA GGC TTG GTG CAA CCT GGA GGA TCC ATG <u>AGA</u> CTC TCT TGT GCT GCT TCT GGA TTC ACT TTT AGT GAT

GCC TGG ATG GAC TGG GTC CGC CAG TCT CCA <u>GGG</u> AAG GGG CTT GAG TGG GTT GCT GAA ATT AGA AAC AAA GCC

AAT AAT CAT GCA ACA TAT TAT GAT GAG TCT GTG AAA GGG AGG TTC ACC ATC TCA AGA GAT GAT TCC AAA AGT <u>ACT</u>

GTG TAC CTG CTG ATG <u>AAT</u> AGC TTA AGA GCT GAA GAC ACT <u>GCC</u> CTT TAT TAC TGT ACT GGG GAG TTT GCT AAC TGG

GGC CAG GGG ACT CTG GTC ACT GTC TCT <u>TCT</u> G

Example 48
Humanized BrE-3 Antibody Expression

Two expression vectors pAG4622 and pAH4604 (Coloma, M. J., et al. (1992), supra) were used that were developed and provided by S. L. Morrison (Dept. of Microbiology and Molecular Genetics, UCLA). Any cDNA encoding a signal peptide and either the variable heavy chain or the variable light chain can, in principle, be inserted into these vectors resulting in a construction that encodes an IgG1, K, antibody with human constant regions. Correctly modified cDNAs were excised from pCR1000 with EcoRV and Sal I and inserted into pAG4622. These encode the modified light chain. The wild-type heavy chain was similarly excised from pCR1000 by digestion with EcoRV and NhEI and inserted into pAH4604. The restriction and ligation reactions necessary to accomplish these operations were performed under the conditions stipulated by the enzyme manufacturers (New England Biolabs, Beverly, Mass.). Both the vectors and the inserts were purified from an agarose gel prior to ligation, using the Bio101 (La Jolla, Calif.) GeneClean kit (glass beads). The $V_H$ and $V_L$ regions in the final constructions were sequenced once again to verify that they are correct. The non-producer myeloma cell line SP2/0-Ag14, ATCC: CRL 1581, (Shulman M., et al. (1978), supra) was transfected with both plasmid constructions, and antibody producers were isolated following the recommendations outlined in (Coloma, M. J. et al. (1992), supra) except that selection was done only for the uptake of hisD (by adding 5 mM histidinol to the medium and readjusting the pH to 7.4 with NaOH). Usually after ten days, stable transfectant colonies were established at a frequency of approximately $10^{-5}$ to $10^{-4}$. Colonies were then transferred to normal medium (without histidinol). The culture media were either Dulbeco's modified Eagle's medium (DME): fetal bovine serum (FBS), 90:10, v/v, or a mixture of DME:RPMI:FBS, 45:45:10, v/v/v. Penicillin and streptomycin were added to prevent bacterial growth.

The supernatants from stable transfectants were assayed for the presence of the antibodies. This was done by capturing the secreted chimeric antibody with a plate-bound goat anti-human-kappa chain antibody and developing with goat anti-human-gamma chain antibody, essentially as described previously (Coloma, M. J. (1992), supra) except that the secondary antibody was radiolabeled with $^{125}$I.

The supernatants were also assayed for binding to human milk fat globule (HMFG) as described previously (Ceriani R. L., et al., "Diagnostic Ability of Different Human Milk Fat Globule Antigens in Breast Cancer", Breast Cancer Res. Treat., 15:161–174 (1990)). HMFG is bound to the microtiter plates as described previously (Ceriani, R. I. (1984), supra). Usually most colony supernatants were positive by both assays.

Colonies that secrete the highest level of antibody in the supernatants, as determined by these assays, were subcloned and subsequently adapted to serum-free medium for the purification of antibody. Serum free medium contains HL-1 supplement as directed by the manufacturer (Ventrex Labs., Portland, Me.).

Example 49
Half Humanized-Half Chimeric BrE-3 Antibody

A BrE-3 humanized light chain was paired with an anti-BrE-3 non-humanized chimeric heavy chain by co-transfection of SP2/0 myeloma cells with hybrid plasmids carrying the respective DNA sequences and those of a human $F_c$.

Example 50
Determination of Affinity Constants for Half Humanized and Fully Humanized BrE-3 Antibodies The secreted half humanized-half chimeric and fully humanized antibodies were purified from culture supernatants using a Sepharose 4B-protein A column (Bio-Rad, Richmond, Calif.) as described by Ey et al. (Ey, P. L., et al. (1978), supra). Microtiter plates (Dynatech, Chantilly, Va.) were prepared as described by Ceriani et al. (Ceriani, R. L., et al. (1992), supra) using successive layers of methylated BSA, glutaraldehyde, anti-b-galactosidase and the bacterial fusion protein 11-2 (a hybrid of b-galactosidase and human mammary mucin). Each well contained 388 ng of the 11-2 fusion protein. To each well were added 25 ml $^{125}$I-BrE-3 in RIA buffer (10% bovine calf serum, 0.3% triton X-100, 0.05% sodium azide pH7.4, in phosphate buffer saline) and compete with 25 ml of either unlabeled murine or chimeric antibody in RIA buffer at the final concentrations of 130 pM, 850 pM, 1.3 nM, 4 nM, and 13 nM). Iodinations were performed with $^{125}$I (17 Ci/mg, Nordion International). Fifty micrograms of monoclonal antibody BrE-3 (Coulter, Hialeah, Fla.) were labeled at a specific activity of 9.56 mCi/mg using the chloramine T method as described previously by Ceriani et al. (Ceriani, R. L., et al. (1988), supra)

Antibody-antigen affinity constants were determined by taking the reciprocal of the concentration of competing unlabeled monoclonal antibody that produced 50% binding as described by Sheldon et al. (Sheldon, K., et al. (1987), supra). The protocol used to determine affinity constants was as described above except that in each case, an unlabeled antibody competed for binding to antigen against the same radiolabeled antibody. Both, the half humanized-half chimeric antibody and the fully humanized antibody competed about as well or better with the anti-BrE-3 murine antibody for the antigen.

Polyacrylamide gel electrophoresis was performed to insure that the antibody chains migrated as expected. The affinity binding constants of the murine, chimeric, half humanized and humanized antibodies were determined in independent competition assays.

Example 51
Histochemical Specificity of Half and Fully Humanized BrE-3 Antibodies Immunohistochemical staining using the immunoperoxidase technique of consecutive human breast carcinoma tissue sections was used as a test to verify that the analogue antibodies retain useful affinity for the carcinoma antigens. Breast carcinoma tissue sections were stained with the supernatant of the half humanized/half chimeric and fully humanized transfected cells using the Vectastain ABC method (Vector Labs, Burlingame, Calif.). Both antibodies showed strong staining patterns.

Example 52
Gel Chromatography of Half Humanized-Half Chimeric and Fully Humanized BrE-3 Antibodies Antibody disulfide bonds were reduced by heating for 10 min at 65° C. in Laemmli loading buffer containing 5% beta-mercaptoethanol. The separated chains were then chromatographed on a SDS polyacrylamide gel (10%). Two bands were observed for both antibodies of similar migration pattern as the murine antibody. These data were also confirmed by Western blotting.

Example 53
Deduced Amino Acid Sequences of Humanized BrE-3 Variable Light and Heavy Chains The amino acid sequences of the light and heavy chains of the analogue humanized antibody are shown in Tables 47 and 48 below. These amino acid sequences may be improved either to increase affinity for the antigen or to decrease immunogenicity in humans. Numerous variants of this sequence may be engineered in accordance with the invention.

TABLE 47

Humanized BrE-3 $V_L$ Analogue Amino Acid Sequence
BrE-3 $V_L$ FR-HZ

| | |
|---|---|
| Leader | mklpvrllvlLFWIPASIS (Seq. ID No: 66) |
| FR1 | DVVMTQSPLSLPVTPGEPASISC (Seq. ID No: 67) |
| CDR1 | RSSQNLVHNNGNTYLY (Seq. ID No: 68) |
| FR2 | WFLQKPGQSPKLLIY (Seq. ID No: 69) |
| CDR2 | RASIRFS (Seq. ID No: 70) |
| FR3 | GVPDRFSGSGSGTDFTLKISRVEAEDVGVYFC (Seq. ID No: 71) |
| CDR3 | FQGTHVPWT (Seq. ID No: 72) |
| FR4 | FGGGTKLEIK (Seq. ID No: 73) |

TABLE 48

BrE-3 $V_H$ Analogue Amino Acid Sequence
BrE-3$V_H$ FR-HZ

| | |
|---|---|
| Leader | mylglnyvflVFLLKGVQS (Seq. ID No: 74) |
| FR1 | EVQLVESGGGLVQPGGSMRLSCAASGFTFS (Seq.ID No: 75) |
| CDR1 | DAWMD (Seq. ID No: 76) |
| FR2 | WVRQSPGKGLEWVA (Seq. ID No: 77) |
| CDR2 | EIRNKANNHATYYDESVKG (Seq. ID No: 78) |
| FR3 | RFTISRDDSKSTVYLQMNSLRAEDTALYYCTG (Seq. ID No: 79) |
| CDR3 | EFAN (Seq. ID No: 80) |
| FR4 | WGQGTLVTVSS (Seq. ID No: 81) |

Example 54
Choice of Murine Model of Known Structure for Humanization of anti-KC-4 Antibody The classification of the $V_H$ and $V_L$ domains of an antibody such as the anti-KC-4 antibody was done according to Kabat et al. (Kabat, E. A., et al., "Sequences of Proteins of Immunological Interest" NIH (1991). The KC-4G3 kappa chain $V_L$ domain belongs to group 11 and the $V_H$ domain belongs to group IIId. A murine antibody was then found, whose structure had been determined, and whose variable regions belong to the same classes. The anti-myohemerythrin peptide antibody B1312 fits these requirements since, like the anti-KC-4 murine antibody, it has $V_L$ and $V_H$ domains belonging to groups II and IIId (Stanfield, R. L., et al., "Crystal Structures of an Antibody to a Peptide and its complex with Peptide Antigen at 2.8 A", Science 248:712–719 (1990)). Thus, the three-dimensional structures of antibodies the anti-KC-4 and B1312 antibodies should be similar, and the humanization of the anti-KC-4 antibody may be modeled after B1312.

Example 55
Choice of Target Human Framework for Humanization of Chimeric anti-KC-4 Antibody The choice of the target human framework was based strictly on the similarity at the residues that were judged to be structurally important according to the B1312 model. That is, only amino acids that could be involved in contacts with CDRs of the opposite chain, or amino acids whose side-chains were predicted to be inwardly pointed. The positions of these amino acids are shown in Tables 49 below.

TABLE 49

Important Amino Acid Positions
for anti-KC-4 Antibody

Light Chain Variable Region Framework 2, 3, 4, 6, 7, 11, 13, 19, 21, 22, 23, 35, 36, 37, 38, 43, 44, 46, 47, 48, 49, 58, 60, 61, 62, 69, 71, 73, 75, 78, 82, 85, 86, 87, 88, 98, 102, 104 and 106.

Heavy Chain Variable Region Framework 2, 4, 6, 12, 18, 20, 22, 24, 27, 28, 29, 36, 37, 38, 39, 43, 45, 46, 47, 48, 49, 66, 67, 69, 71, 78, 80, 82, 82c, 86, 88, 90, 91, 92, 93, 94, 103, 107, 109 and 111.

The numbering system is conventionally accepted (Kabat, et al. (1991), supra) and is shown in Tables 10 and 11 above. In this case, the consensus sequences of all human $F_v$ regions were selected as the target human framework to minimize the immunogenicity of the product.

First, the sequences of the murine variable chains were aligned with consensus sequences from all known human variable region classes (Herron, J. N., (1989), supra) and the number of differences in the amino-acids that must be retained from the murine were scored. The positions of these amino acids were obtained from those of the B1312 murine monoclonal antibody, which was chosen to model the humanization of the anti-KC-4 antibody.

Based on these scores, the consensus sequences human frameworks belonging to groups $V_k$II and $V_H$III were chosen to receive the anti-KC-4 murine antibody CDRs plus other important amino acids.

Example 56

Identification of Murine-Human anti-KC-4 Antibody Differences

The original murine sequences (anti-KC-4 $V_K$ or $V_H$) were aligned with their closest human (Human KII or HIII) relatives that were chosen after comparing their sequences as described in Example 34 above. In the present example, it was intended to be substituted as many amino acids as possible in going from the murine to the humanized variable consensus sequences, leaving the important amino acids intact as described in Examples 55 and 57. The amino acids chosen to be preserved were a subset of those listed above. These were selected by analogy to the B1312 sequence. The single exception was the glycine (100) residue of the original framework of the variable region of the murine kappa chain, which was retained despite not being encompassed in Table 49 above since it was thought that it might contact the variable domain of the heavy chain. Such contacts were observed in at least three Fab that lack a gly at this position.

Example 57

Identification of Important Murine anti-K-4 Antibody Amino Acids

The "important" murine amino acids were chosen for preservation based on the contacts of a particular amino acid with the CDRs, and with the opposite chains and/or whether their side chains are pointing inwardly or outwardly. The positions of these "important" amino acids were determined based on the examination of the known structures of other antibodies.

Most of the "important" amino acids were selected on the basis of the structure of antibody B1312 and according to Tables 2, 3, 4, 5, 6, 8 and 9 above.

The final selection of amino acid positions for actual mutation was attained by comparing the position of all amino acids that are candidates for mutation with those that are "important" and should be preserved. Any "important" amino acid position was eliminated from the list of candidates. Table 50 below shows the amino acids that were selected for change in the murine sequence to attain the humanized sequence in the present exemplary analogue.

TABLE 50

Anti-KC-4 Murine Antibody Variable Region Amino Acids Selected for Mutation

| Position | KC-4G3 Murine Identity ----> | Consensus Human Identity |
|---|---|---|
| Light Chain Variable Region | | |
| 14 | S | T |
| 15 | L | P |
| 17 | D | E |
| 18 | Q | P |
| 45 | K | Q |
| 74 | N | K |
| 83 | L | V |
| Heavy Chain Variable Region | | |
| 13 | K | Q |
| 19 | K | R |
| 40 | S | A |
| 42 | E | G |
| 44 | R | G |
| 74 | A | S |
| 81 | E | Q |
| 82a | S | N |
| 84 | S | A |
| 89 | M | V |
| 110 | S | T |
| 113 | A | S |

The change N→K at position 74 in the variable light chain knowingly eliminated an N-linked glycosylation site, which was present in the original murine monoclonal antibody.

Example 58

Introduction of Changes in Amino Acid Sequence for Humanization of anti-KC-4 Antibody The introduction of the changes in the amino acid sequence was not done as described in Example 37 above. Instead the DNA encoding each humanized variable region was synthesized in a single polymerase chain reaction (PCR) using overlapping oligonucleotides in accordance with the method described by Ye et al. (Ye, Q-Z, Jonhson, L. L., and Baragi, V., "Gene Synthesis and Expression in *E. coli* for PUMP, a Human Matrix Metalloproteinase", BBRC 186(1): 143–149 (1992)). The sequences of the mutagenic are shown in Table 51 below.

TABLE 51

Primers for Humanization of anti-KC-4 Murine Antibody Variable Regions

| | | |
|---|---|---|
| JA59 | CCCGGATCC TTTAAAAGGT GTCCAGTGTG AAGTGCAGAT GGTGGAG TCTG | (SEQ. ID No.: 82) |
| J060 | GAATTCGGGGC TAGCACTAGA GACAGTGACC AGAGTCCCTT GGCCCCAG | (SEQ. ID No.: 83) |
| J061 | AGTGCAGATG GTGGAGTCTG GGGGAGGCTT AGTGCAGCCT GGAGGGTCCC TGAGACTCTC CTGTGCAGCC TCTGGATTCG CTTTCAGTAG CTATGCCATG T | (SEQ. ID No.: 84) |
| J062 | CTTGATAGTA GGCGTAATTA CCACCACTAC TAATTTCTGC GACCCACTCC AGCCCCTTCC CTGGAGCCTG GCGAACCCAA GACATGGCAT AGCTACTGAA A | (SEQ. ID No.: 85) |
| J063 | TAATTACGCC TACTATCAAG ACACTGTGAC GGGCCGATTC ACCATCTCCA GAGACAATTC CAAGAACACC CTGTACCTGC AAATGAACAG TCTGAGGGCT G | (SEQ. ID No.: 86) |
| J064 | CCAGAGTCCC TTGGCCCCAG TAAGCAAACC AGGCCGGGAT ACCGTAGTCC TCCCTTGCAC AGTAATACAC GGCCGTGTCC TCAGCCCTCA GACTGTTCAT T | (SEQ. ID No.: 87) |

TABLE 51-continued

Primers for Humanization of anti-KC-4
Murine Antibody Variable Regions

J073  GGGAAGCTTG ATATCCACCA TGAAGTTGCC TGTTAGGCTG TTGGTG CTGA TGTTCTGGAT (SEQ. ID No.: 88)
      TCCTGC

J074  AAAGATTCG TCGACTTACG TTTTATTTCC AGCTTGGTCC CCCCTCC GAA CGTGTACGGA (SEQ. ID No.: 89)
      ACATGT

J075  CTGATGTTCT GGATTCCTGC TTCCAGCAGT GATGTTTTGA TGACCCAAAC TCCTCTCTCC (SEQ. ID No.: 90)
      CTGCCTGTCA CTCCAGGAGA GCCAGCCTCC ATCTCTTGCA

J076  CTGTGGAGAC TGGCCTGGTT TCTGCAGGTA CCATTCTAAA TAGGTGTTTC CATTACTATG (SEQ. ID No.: 91)
      TACAATGCTC TGACTAGATC TGCAAGAGAT GGAGGCTGGC

J078  CGAACGTGTA CGGAACATGT GAACCTTGAA AGCAGTAATA AATTCC CACA TCCTCAGCCT (SEQ. ID No.: 92)
      CCACTCTGCT GATCTTGAGT GTGAAATCTG TCCCTGATCC

Example 59

Synthesis of Primers for Humanization of anti-KC-4 Antibod

All primers were synthesized on a PCR-Mate EP DNA synthesizer model 391 (Applied Biosystems, Foster City Calif.) using 40nmole columns, cycle 1:63, with Trityl off. None were purified before use. The EIPCR method was used for preparing all primer sets. Their sequences are shown in Table 51 above.

The plasmid DNA template was extracted with a kit purchased from QIAGEN (Tchapsworth, Calif.) and diluted to 1 ng/ml in 10 mM TRIS 1 mM EDTA pH 7.5–8. This plasmid is composed of vector pCR1000 (Invitrogen Corporation, San Diego, Calif.) into which the cDNA encoding the variable region to be humanized was inserted.

Example 60

Synthesis of anti-KC-4 Humanized Heavy Chain Variable Regions

A mixture of PCR primers was made, where each primer was present at a concentration of 10 pmole/ml in water.

Four 101' mer oligonucleotides (JO61, JO62, JO63 and JO64), one 50' mer (JO59), and one 49' mer (JO60), were used for the synthesis of the humanized variable heavy chain. The oligonucletides concentrations were estimated using the formula $c = mg/ml$ The PCR amplification conditions were as follows. All reagents as well as the GeneAmp PCR system 9600 were purchased from Perkin Elmer Cetus. Optimal PCR conditions were determined empirically for each pair of mutagenic primers. A matrix of conditions varying the concentration of $MgCl_2$, mutagenic primers, and template plasmid DNA were set up as follows. However, the annealing and extension temperatures during PCR may be varied.

2 mM primer JO59 150 nM each of primers JO61, 62, 63 and 64.

2 mM primer JO60 200 mM each of dGTP, dATP, TTP, and dCTP.

10 mM KCl 20 mM Tris-HCl pH 8.8

10 mM $(NH_4)_2SO_4$ 2 units per 100 ml reaction Vent DNA 0.1% Triton X-100 polymerase (New England Biolabs) 6 mM $MgSO_4$

Example 61

Hot Start PCR for Humanization of anti-KC-4 Antibody

All the components of the PCR mixture, with the exception of Vent DNA polymerase, were mixed. The mixture was then dispensed in 19 ml aliquots into 5 PCR tubes. The reason for performing five independent reactions was to decrease the odds that unwanted mutations be isolated as a result of nucleotide misincorporation during PCR. The tubes were heated to 95° C. for 5 minutes and then cooled to 72° C. While at that temperature 1 ml of an appropriate Vent DNA polymerase dilution in 1×buffer was added to the reaction mixture (hot start). The temperature cycling then proceeds as follows.

3 cycles 29 cycles

72° C., 10 min

Example 62

Extra Final Extension for Humanized anti-KC-4 Antibody DNA

After cycling, one extra final extension reaction was carried out. Extra deoxyribonucleotide triphosphates (to 125 mM) and 1 unit of Vent DNA polymerase were added, and the mixture was heated to 72° C. for 10 minutes.

The resulting synthetic DNA fragment was digested with DraI and NheI and inserted into the same restriction sites a plasmid construct encoding the corresponding murine heavy chain variable region.

Example 63

Synthesis of anti-KC-4 Humanized Light Chain Variable Regions

The light chain variable region ($V_L$) genes were synthesized in a similar way as described in Examples 60 to 62 above for the heavy chain variable regions.

Example 64

Purification of Humanized anti-KC-4 PCR Products

The PCR products were then separated on a 0.8% agarose gel in 1×TAE buffer and 0.5 mg/ml ethidium bromide. The correct DNA band were visualized with UV light (366 nm), excised from the gels and extracted with the GeneClean kit (Bio 101, La Jolla, Calif.).

Example 65

Litigation of Humanized anti-KC-4 DNA to Plasmid (Reclosure of Plasmid)

The ligation mixtures consisted of 5 ml extracted DNA, 2 ml 10×ligation buffer (NEB) 1 ml T4 DNA polymerase (NEB), 12 ml water. The amount of plasmid DNA may be varied depending of the intensity of the band extracted from the Gel. Ligation into a pBluescript KS+ plasmid (Stratagene) was carried out at room temperature for 2 hrs., or alternatively at 14° C. overnight.

Example 66
Transformation and Sequencing of Humanized anti-KC-4 DNA

The reclosed plasmids were then transformed into *E. coli* utilizing Inv alpha F' competent cells purchased from Invitrogen Corporation, San Diego Calif. Plasmid DNA was then prepared from a few transformants and sequenced to verify that mutagenesis was successful.

Example 67
Hybrid Plasmid Preparation and Sequencing

Plasmid DNA was then prepared and sequenced to verify that the mutagenesis was successful. The mutated anti-KC-4 humanized analogue DNA sequences for the $V_H$ and $V_L$ segments are shown in

TABLE 52

Humanized anti-KC-4 Antibody $V_L$
Analogue DNA Sequences
anti-KC-4 $V_L$ FR-HZ

ATG AAG TTG CCT GTT AGG CTG TTG GTG CTG ATG TTC TGG ATT CCT GCT    (SEQ ID No.: 93)
TCC AGC AGT GAT

GTT TTG ATG ACC CAA ACT CCT CTC TCC CTG CCT GTC ACT CCA GGA GAG
CCA GCC TCC

ATC TCT TGC AGA TCT AGT CAG AGC ATT GTA CAT AGT AAT GGA AAC ACC
TAT TTA GAA TGG

TAC CTG CAG AAA CCA GGC CAG TCT CCA CAG CTC CTG ATC TAC AAA GTT
TCC ATC CGA TTT

TCT GGG GTC CCA GAC AGG TTC AGT GGC AGT GGA TCA GGG ACA GAT TTC
ACA CTC AAG

ATC AGC AGA GTG GAG GCT GAG GAT GTG GGA ATT TAT TAC TGC TTT CAA
GGT TCA CAT GTT

CCG TAC ACG TTC GGA GGG GGG ACC AAG CTG GAA ATA AAA C

TABLE 53

Humanized anti-KC-4 Antibody $V_H$ Analogue DNA Sequences
anti-KC-4 $V_H$ FR-HZ

ATG GAC TTT GGG CTC AGC TTG GTT TTC CTT GTC CTT ATT TTA AAA GGT GTC CAG TGT GAA

GTG CAG ATG GTG GAG TCT GGG GGA GGC TTA GTG CAG CCT GGA GGG TCC CTG AGA CTC

TCC TGT GCA GCC TCT GGA TTC GCT TTC AGT AGC TAT GCC ATG TCT TGG GTT CGC CAG

GCT CCA GGG AAG GGG CTG GAG TGG GTC GCA GAA ATT AGT AGT GGT GGT AAT TAC GCC

TAC TAT CAA GAC ACT GTG ACG GCC CGA TTC ACC ATC TCC AGA GAC AAT TCC AAG AAC

ACC CTG TAC CTG CAA ATG AAC AGT CTG AGG GCT GAG GAC ACG GCC GTG TAT TAC TGT

GCA AGG GAG GAC TAC GGT ATC CCG GCC TGG TTT GCT TAC TGG GGC CAA GGG ACT CTG

GTC ACT GTC TCT AGT

Example 68
Expression of Anti-KC-4 Humanized Antibody

Two expression vectors pAG4622 and pAH4604 (Coloma, M. J., et al. (1992), supra) were used that were developed and provided by S. L. Morrison (Dept. of Microbiology and Molecular Genetics, UCLA). Any cDNA encoding a signal peptide and either the variable heavy chain or the variable light chain can, in principle, be inserted into these vectors resulting in a construction that encodes an IgG1, K, antibody with human constant regions. Correctly modified cDNAs were excised from pCR1000 with EcoRV and Sal I and inserted into pAG4622. These encode the-modified light chain. The wild-type heavy chain was similarly excised from pCR1000 by digestion with EcoRV and NhEI and inserted into pAH4604. The restriction and ligation reactions necessary to accomplish these operations were performed under the conditions stipulated by the enzyme manufacturers (New England Biolabs, Beverly, Mass.). Both the vectors and the inserts were purified from an agarose gel prior to ligation, using the Bio101 (La Jolla, Calif.) GeneClean kit (glass beads). The $V_H$ and $V_L$ regions in the final constructions were sequenced once again to verify that they were correct. The non-producer myeloma cell line SP2/0-Ag14, ATCC: CRL 1581, (Shulman M., et al. (1978), supra) was transfected with both plasmid constructions, and antibody producers were isolated following the recommendations outlined in Coloma et al. (Coloma, M. J. et al. (1992), supra) except that selection was done only for the uptake of hisD (by adding 5 mM histidinol to the medium and readjusting the pH to 7.4 with NaOH). Usually after ten days, stable transfectant colonies were established at a frequency of approximately $10^{-5}$ to $10^{-4}$. Colonies were then transferred to normal medium (without histidinol). The culture media were either Dulbeco's modified Eagle's medium (DME): fetal bovine serum (FBS), 90:10, v/v, or a mixture of DME:RPMI:FBS, 45:45:10, v/v/v. Penicillin and streptomycin were added to prevent bacterial growth.

The supernatants from stable transfectants were assayed for the presence of the antibodies. This was done by capturing the secreted chimeric antibody with a plate-bound goat anti-human-kappa chain antibody and developing with goat anti-human-gamma chain antibody, essentially as described previously (Coloma, M. J. (1992), supra) except that the secondary antibody was radiolabeled with $^{125}$I. The supernatants were also assayed for binding to human milk fat globule (HMFG) as described previously (Ceriani R. L., et al., "Diagnostic Ability of Different Human Milk Fat Globule Antigens in Breast Cancer", Breast Cancer Res. Treat., 15:161–174 (1990)). HMFG is bound to the microtiter plates as described previously (Ceriani, R. I. (1984), supra). Usually most colony supernatants were positive by both assays.

Colonies that secrete the highest level of antibody in the supernatants, as determined by these assays, were subcloned and subsequently adapted to serum-free medium for the purification of antibody. Serum free medium contains HL-1 supplement as directed by the manufacturer (Ventrex Labs., Portland, Me.).

Example 69
Half Humanized-Half Chimeric anti-KC-4 Antibody

An anti-KC-4 humanized light chain was paired with an anti-KC-4 non-humanized chimeric heavy chain by co-transfection of SP2/0-Ag14 myeloma cells with hybrid plasmids carrying the respective DNA sequences and those of a human $F_c$.

In addition, an anti-KC-4 humanized heavy chain was paired with an anti-KC-4 non-humanized chimeric light chain as described in Example 69 above.

Example 70
Fully Humanized anti-KC-4 Antibody

An anti-KC-4 fully humanized antibody was prepared by pairing fully humanized anti-KC-4 light and heavy chains by co-transfection as described in Example 69 above.

Example 71
Determination of Affinity Constants for Half and Fully Humanized anti-KC-4 Antibodies The secreted half humanized antibodies and the fully humanized antibody were purified from culture supernatants using a Sepharose 4B-protein A column (Bio-Rad, Richmond, Calif.) as described by Ey et al. (Ey, P. L., et al. (1978), supra). Microtiter plates (Dynatech, Chantilly, Va.) were prepared as described by Ceriani et al. (Ceriani, R. L., et al. (1992), supra) using successive layers of methylated BSA, glutaraldehyde, anti-b-galactosidase and the bacterial fusion protein 11-2 (a hybrid of b-galactosidase and human mammary mucin). Each well contained 388 ng of the 11-2 fusion protein. To each well were added 25 ml $^{125}$I-KC-4 in RIA buffer (10% bovine calf serum, 0.3% triton X-100, 0.05% sodium azide pH 7.4, in phosphate buffer saline) and compete with 25 ml of either unlabeled murine or chimeric antibody in RIA buffer at the final concentrations of 130 pM, 850 pM, 1.3 nM, 4 nM, and 13 nM). Iodinations were performed with $^{125}$I (17 Ci/mg, Nordion International). 50 mg anti-KC-4 monoclonal antibody (Coulter, Hialeah, Fla.) were labeled at a specific activity of 9.56 mCi/mg using the chloramine T method as described previously by Ceriani et al. (Ceriani, R. L., et al. (1988), supra).

The antibody-antigen affinity constants were determined by taking the reciprocal of the concentration of competing unlabeled monoclonal antibody that produced 50% binding as described by Sheldon et al. (Sheldon, K., et al. (1987), supra). The protocol used to determine affinity constants was as described above except that in each case, an unlabeled antibody competed for binding to the antigen against the same radiolabeled antibody. The fully humanized antibody was shown to compete about as well or better with the anti-KC-4 murine antibody for the KC-4G3 antigen.

Polyacrylamide gel electrophoresis was performed to insure that the antibody chains migrated as expected. The affinity binding constants of the murine, chimeric, half humanized and humanized antibodies were determined in independent competition assays.

Example 72
Histochemical Specificity of Half and Fully Humanized anti-KC-4 Antibodies Immunohistochemical staining using the immunoperoxidase technique of consecutive human breast carcinoma tissue sections was used as a test to verify that the analogue antibodies retain the affinity for the KC-4G3 carcinoma antigen of the murine antibody. Breast carcinoma tissue sections were stained with the supernatant of the KC-4 murine and fully humanized transfected cells using the Vectastain ABC method (Vector Labs, Burlingame, Calif.). Both antibodies showed strong staining patterns.

The following Table 54 shows the results of the immunoperoxidase staining of five human breast carcinomas with either the standard anti-KC-4G3 murine or the fully humanized antibodies. Both stained the same tissues at a comparable level.

TABLE 54

Immunoperoxidase Staining of Human Breast Carcinoma Tissue Sections with Murine and Fully Humanized anti-KC-4 Antibodies

| Breast Tumor | Murine Antibody | Fully Humanized Antibody |
|---|---|---|
| 1 | ++ | ++ |
| 2 | +++ | +++ |
| 3 | – | – |
| 4 | ++ | ++ |
| 5 | +++ | +++ |

Example 73
Binding to HMFG of Half Humanized and Fully Humanized anti-KC-4 Antibodies Tissue culture supernatants from transfectants of all three anti-KC-4 variants of the humanized antibody were shown to bind the human milk fat globule (HMFG) as determined by radio-immunodetections.

Example 74
Half Humanized and Fully Humanized anti-KC-4 Antibodies Bind to Goat anti-Human k or γ Antibodies Tissue culture supernatants from transfectants of all three variants of the anti-KC-4 humanized antibody were shown to bind in sandwich radioimmunodetections to both goat anti-human kappa chain antibody bound to microtiterplate wells (750 ng/well), and to radio-iodinated $^{125}$I-labeled goat anti-human gamma chain antibodies.

The results of these sandwich assays demonstrate that both chains of the humanized antibodies indeed possess human kappa and gamma constant regions.

Example 75
Deduced Amino Acid Sequences of Humanized anti-KC-4 Variable Light and Heavy Chains The amino acid sequences of the light and heavy chains of the analogue humanized antibody are shown in Tables 55 and 56 below. The actual amino acid sequences may be varied either to increase affinity for the antigen or to decrease immunogenicity in humans. Numerous variants of this sequence may be engineered in accordance with the invention.

TABLE 55

Humanized anti-KC-4 Antibody V$_L$ Analogue Sequence
anti-KC-4 V$_L$ FR-HZ (Seq. ID No:95)

MKLPVRLLVL MFWIPASSSD VLMTQTPLSL PVTPGEPASI

SCRSSQSIVH SNGNTYLEWY LQKPGQSPQL LIYKVSIRFS

GVPDRFSGSG SGTDFTLKIS RVEAEDVGIY YCFQGSHVPY

TFGGGTKLEI K

TABLE 56

Humanized anti-KC-4 Antibody V$_H$ Analogue Sequence
anti-KC-4 V$_H$ FR-HZ (Seq. ID No:96)

MDFGLSLVFL VLILKGVQCE VQMVESGGGL VQPGGSLRLS

CAASGFAFSS YAMSWVRQAP GKGLEWVAEI SSGGNYAYYQ

DTVTGRFTIS RDNSKNTLYL QMNSLRAEDT AVYYCAREDY

GIPAWFAYWG QGTLVTVSS

Example 76
Half Humanized-Half Chimeric anti-BrE-3 Antibodies

A humanized BrE-3 light chain was paired with a non-humanized chimeric BrE-3 heavy chain by co-transfection of SP2/0-Ag14 myeloma cells with hybrid plasmids carrying the respective DNA sequences and those of a human F$_c$. The cell line obtained, HuBrE3V1, was deposited with the ATCC on Nov. 10, 1993 and awarded an accession number HB 11486.

In addition, a humanized BrE-3 heavy chain was paired with a non-humanized chimeric BrE-3 light chain as described in Example 69 above. The thus obtained cell, HuBrE3V3 was deposited with the ATCC on Nov. 10, 1993 and was awarded accession number HB 11487.

Example 77
Fully Humanized BrE-3 Antibody

The fully humanized BrE-3 antibody was prepared by pairin fully humanized BrE-3 light and heavy chains by co-transfection as describe in Example 69 above. The thus obtained cell line, HuBrE3V2, was deposited ith the ATCC on Nov. 13, 1992 and awarded the accession number HB 1111200.

Example 78
Half Humanized and Fully Humanized BrE-3 Antibodies Bind to Goat anti-Human K or y Antibodies Tissue culture supernatants from transfectants of all three variants of the humanized BrE-3 antibody were shown to bind in sandwich radioimmunodetections to both goat anti-human kappa chain antibody bound to microtiterplate wells (750 ng/well), and to radio-iodinated $^{125}$I-labeled goat; anti-human gamma chain antibodies.

The results of these sandwich assays demonstrate that both chains of the humanized antibodies indeed possess human kappa and gamma constant regions.

Example 79
Binding to HMFG of Half Humanized and Fully Humanized BrE-3 Antibodies Tissue culture supernatants from transfectants of all three BrE-3 variants of the humanized antibody were shown to bind the human milk fat globule (HMFG) 10 as determined by radio-immunodetections.

Example 80
Competition Assays and Determination of Affinity Constants for Half Humanized BrE-3 Antibodies The secreted half humanized antibodies were purified from culture supernatants using a Sepharose 4B-protein A column (Bio-Rad, Richmond, Calif.) as described by Ey et al. (Ey, P. L., et al. (1978), supra). The fully humanized antibody (HuBrE3 V2) was not purified. Its concentration in the culture supernatant was determined by radioimmunodetection using a plate-bound goat anti-human kappa chain antibody as a capturing antibody and using radiolabled goat anti-human gamma chain antibody as a detecting antibody. A parallel standard curve of human IgG$_1$K was used to determine the unknown concentration of HuBrE3 V2. Microtiter plates (Dynatech, Chantilly, Va.) were prepared as described by Ceriani et al. (Ceriani, R. L., et al. (1992), supra) using successive layers of methylated BSA, glutaraldehyde, anti-fl-galactosidase and the bacterial fusion protein 11-2 (a hybrid of β-galactosidase and human mammary mucin). Each well contained 388 nanograms of the 11-2 fusion protein. To each well were added 25, μl $^{125}$I-BrE-3 in RIA buffer (10% bovine calf serum, 0.3% triton X-100, 0.05% sodium azide pH 7.4, in phosphate buffer saline) and competed with 25 μl of either unlabeled murine or humanized antibody in RIA buffer at the final concentrations of 130 pM, 850 pM, 1.3 nM, 4 nM, and 13 nM). Iodinations were performed with $^{125}$I (17 Ci/mg, Nordion International). 50 μg BrE-3 monoclonal antibody (Coulter, Hialeah, Fla.) were labeled at a specific activity of 9.56 mCi/mg using the chloramine T method as described previously by Ceriani et al. (Ceriani, R. L., et al. (1988), supra).

All humanized versions of the BrE-3 antibody were shown to compete about as well or better with the labeled murine BrE-3 antibody for the antigen as did the murine BrE3 antibody. The protocol used to determine affinity constants was as described above except that in each case, an unlabeled antibody competed for binding to the antigen against the same radiolabeled antibody. The antibody-antigen affinity constants were determined by taking the reciprocal of the concentration of competing unlabeled monoclonal antibody that produced 50% binding as described by Sheldon et al. (Sheldon, K., et al. 11987), supra).

Polyacrylamide gel electrophoresis was performed to insure that the antibody chains migrated as expected. The affinity binding constants of the murine, chimeric, half humanized and humanized antibodies were determined in independent competition assays.

Example 81
Histochemical Specificity of Half Humanized BrE-3 Antibodies

Immunohistochernical staining using the immunoperoxi-Jase technique of consecutive human breast carcinoma tissue sections was used as a test to verify that the analogue antibodies retain the affinity for the carcinoma antigen of the murine BrE-3 antibody. Breast carcinoma tissue sections wer stained with the supernatant of cells transfected with the HuBrE3 V1 humanized antibody using the Vectastain ABC method (Vector Labs, Burlingame, Calif.). Both antibodies showed strong staining patterns.

The following Table 57 shows the results of the immunoperoxidase staining of five human breast carcinomas with either the standard BrE-3 murine or the half humanized HuBrE3 V1 antibody. Both stained the same tissues at a comparable level.

TABLE 57

Immunoperoxidase Staining of Human Breast Carcinoma Tissue Sections with Murine and Half Humanized BrE-3 Antibodies

| Breast Tumor | Murine Antibody | Half Humanized Antibodies |
|---|---|---|
| 1 | ++ | ++ |
| 2 | +++ | +++ |
| 3 | – | – |
| 4 | ++ | ++ |
| 5 | +++ | +++ |

Example 82
Hybridoma Cell Deposits

The following cell lines were deposited as present examples of the best mode of the invention. The hybridoma cell lines expressing the murine-human fully chimeric BrE-3 and anti-KC4 antibodies and the fully humanized BrE-3 antibody were deposited with the ATCC, 12301 Parklawn Drive, Rockville, Md. 20852, USA, on Nov. 13, 1992 under the Budapest Treaty, and have been assigned Accession Nos. HB 11199 (Chimeric BrE-3 A1C10), HB 11201 (Chimeric anti-KC-4 E8) and HB 11200 (Humanized BrE-3 A1C10). The hybridoma cell line expressing the anti-KC-4 humanized antibody was deposited with the ATCC on Sep. 23, 1993 and has been assigned Accession No. HB 11455 (Humanized HuKC-4V2). The half chimeric/ half humanized antibody cell lines deposited with the ATCC are as follows: ATCC No. HB 11454 (light chain humanized/ heavy chain chimeric HuKC-4V1) and ATCC No. HB 11456 (heavy chain humanized/ light chain chimeric HuKC-4V3) were deposited on Sep. 23, 1993, and ATCC No. HB 11486 (light chain humanized/heavy chain chimeric BrE3V1) and ATCC No. HB 11487 (heavy chain humanized/light chain chimeric (BrE3V3) were deposited on Nov. 11, 1993 under the Budapest Treaty as examples of the best mode of the invention known to the inventors.

The invention now being fully described, it will be apparent to one of ordinary skill in the art that many changes and modifications can be made thereto without departing from the spirit or scope of the invention as set forth herein.

What is claimed is:

1. A method of reducing tumor growth or reducing the size of a tumor, comprising administering to a subject in need of treatment an amount of a modified antibody which selectively binds the human milk fat globule (HMFG) antigen, and competes as well or better with the unmodified antibody for binding the HFMG, wherein the modified antibody comprises a non-HMFG antigen-binding peptide from a first species, and an HMFG antigen-binding peptide comprising the light and heavy chains of the variable region of an antibody of a second species, wherein at least one chain of the non-HMFG antigen-binding peptide is linked to the HMFG antigen-binding peptide, the chains may be linked to one another at a site other than the antigenic binding site, and at least one chain of the HMFG antigen-binding peptide has 1 to 46 amino acids subsituted with at least one amino acid selected from the group consisting of the following amino acids at the specific sites and chains:

| Position | Light Chain Amino Acid Substitution | Heavy Chain Amino Acid Substitution |
|---|---|---|
| 1 | D | PVLKARGHDE or Q |
| 2 | WKCRHV or I | M or V |
| 3 | V or L | LQR or K |
| 4 | MPTQLV or I | M or L |
| 5 | T | VD or E |
| 6 | Q | QD or E |
| 7 | TIAD or S | T or S |
| 8 | PA or E | G or E |
| 9 | LF or P | G |
| 10 | T or S | DA or G |
| 11 | NL or V | VF or L |
| 12 | S or P | I or V |
| 13 | V | KE or Q |
| 14 | S or T | P |
| 15 | PFI or L | G |
| 16 | G | RSE or G |
| 17 | TEQ or D | PA or S |
| 18 | PS or Q | M |
| 19 | V or A | R or K |
| 20 | S | V or L |
| 21 | I | S |
| 22 | S | C |
| 23 | C | TS -continued

| Position | Light Chain Amino Acid Substitution | Heavy Chain Amino Acid Substitution |
|---|---|---|
| 25 | | S |
| 26 | | G |
| 27 | | F |
| 28 | | AINS or T |
| 29 | | F |
| 30 | | S |
| 35 | W | |
| 36 | IVHNYF or L | W |
| 37 | WLVKRTHDE or Q | WIFLVMATG or Q |
| 38 | Q | R |
| 39 | R or K | Q |
| 40 | FLKARTGQP or S | VA or S |
| 41 | G | PLVARTSHNE or Q |
| 42 | Q | G or E |
| 43 | P or S | K |
| 44 | P | SR or G |
| 45 | EQR or K | L |
| 46 | RV or L | Q or E |
| 47 | WILMTSN or V | W |
| 48 | FPLVMTS or I | STG or V |
| 49 | Y or S | A |
| 57 | WVTSGDNE or Q | |
| 58 | IYFLVMAT or Q | |
| 59 | S or P | |
| 60 | N or D | |
| 61 | T or R | |
| 62 | F | |
| 63 | IYPLKARSG or T | |
| 64 | D or G | |
| 65 | S | |
| 66 | G | R |
| 67 | A or S | F |
| 68 | VMCARSGQD or E | IS or T |
| 69 | T | I |
| 70 | D | L or S |
| 71 | F | R |
| 72 | T | VKRTSGHDE or N |
| 73 | L | N or D |
| 74 | NLRE or K | FPLVTGDNA or S |
| 75 | L or I | EN or K |
| 76 | IT or S | NTRK or S |
| 77 | S or R | TNIVSM or R |
| 78 | ALI or V | LA or V |
| 79 | KGQ or E | FH or Y |
| 80 | P or A | L |
| 81 | ILVKMAGDN or E | E or Q |
| 82 | D | M |
| 82a | | SDN or I |
| 82b | | IR or S |
| 82c | | PLVMAG or E |
| 83 | MV or L | EKT or R |
| 84 | LVARTS or G | SPVTI or A |
| 85 | IM or V | WIYFPLMCRGD or E |
| 86 | Y | D |
| 87 | IMSHEFY or L | M or T |
| 88 | C | A or G |
| 89 | | ITVM or L |
| 90 | | HF or Y |
| 91 | | Y |
| 92 | | C |
| 93 | | ASHAV or T |
| 94 | | TSDQLAWR or G |
| 98 | F | |
| 99 | G | |
| 100 | IPVKRTGAS or Q | |
| 101 | G | |
| 102 | T | |
| 103 | IYMATGHDEQNR or K | A or W |
| 104 | LG or V | YH or G |
| 105 | ILVTSGHNE or Q | THR or Q |
| 106 | YLVKMRTD or I | G |
| 106a | PLVTI | |
| 107 | IVLMATSGNER or K | AQ or T |
| 108 | | STGM or L |
| 109 | | IKLT or V |
| 110 | | SL or T |
| 111 | | V |
| 112 | | T or S and |
| 113 | | PLVATG or S, |
| | or single chain thereof; | | and following the modified antibody to bind to any antigen present on a neoplastic cell present in the tumor to form antibody-cell antigen complexes, wherein the modified antibody is operatively linked to a therapeutic agent.

2. The method of claim 1, wherein the substitutions in the variable region of the modified antibody are selected from the group consisting of

| Position | Light Chain Amino Acid Substitution | Heavy Chain Amino Acid Substitution |
|---|---|---|
| 1 | PVLKARGHDE or Q | |
| 2 | WKCRH or I | M |
| 3 | V or L | LQR or K |
| 4 | PTQLV or I | |
| 5 | | VD or E |
| 6 | | Q or D |
| 7 | IAD or S | T |
| 8 | A or E | E |
| 9 | F or P | |
| 10 | T | D or A |
| 11 | N or V | V or F |
| 12 | S | I |
| 13 | | K or E |
| 14 | S or T | |
| 15 | PFI or L | |
| 16 | | RS or E |
| 17 | TEQ or D | P or A |
| 18 | PS or Q | |
| 19 | V | R or K |
| 20 | | V |
| 23 | | TS or E |
| 24 | | V |
| 28 | | AINS or T |
| 36 | IVHNYF or L | |
| 37 | WLVKRTHDE or Q | WIFLVMATG or Q |
| 39 | R | |
| 40 | FLKARTGQP or S | VA or S |
| 41 | | PLVARTSHNE or Q |
| 42 | | G or E |
| 43 | P | |
| 44 | | S or R |
| 45 | EQR or K | |
| 46 | R or V | Q |
| 47 | WILMTSN or V | |
| 48 | FPLVMT or S | ST or G |
| 49 | S | |
| 57 | WVTSGDNE or Q | |
| 58 | IYFLVMAT or Q | |
| 59 | S | |
| 60 | N | |
| 61 | T | |
| 63 | IYPLKARSG or T | |
| 64 | D | |
| 67 | A | |
| 68 | VMCARSGQD or E | I or S |
| 70 | | L |
| 72 | | VKRTSGHDE or N |
| 73 | | N or D |
| 74 | NLR or E | FPLVTGDN or A |
| 75 | L | E or N |
| 76 | I or T | NTRK or S |
| 77 | S | TNIVSM or R |
| 78 | AL or I | LA or V |
| 79 | KG or Q | F or H |
| 80 | P | |

-continued

| Position | Light Chain Amino Acid Substitution | Heavy Chain Amino Acid Substitution |
|---|---|---|
| 81 | ILVKMAGDN or E | E |
| 82a | | SDN or I |
| 82b | | I or R |
| 82c | | PLVMAG or E |
| 83 | MV or L | EK or T |
| 84 | LVARTS or G | SPVT or I |
| 85 | IM or V | WIYFPLMCRG or D |
| 87 | IMSHEFY or L | M |
| 88 | | A or G |
| 89 | | ITVM or L |
| 90 | | H or F |
| 93 | | ASHAV or T |
| 94 | | TSDQLAWR or G |
| 100 | IPVKRTGAS or Q | |
| 103 | IYMATGHDEQN or R | A |
| 104 | VL or G | Y or H |
| 105 | ILVTSGHNE or Q | TH or R |
| 106 | YLVKMRT or D | |
| 106a | PLVT or I | |
| 107 | ILVMATSGNE or R | A or Q |
| 108 | | STG or M |
| 109 | | IKL or T |
| 110 | | S or L |
| 112 | | T and |
| 113 | | PLVATS or G. |

3. The method of claim 2, wherein the substitutions in the varible regions of the modified antibody are selected from the group consisting of

| Position | Light Chain Amino Acid Substitution | Heavy Chain Amino Acid Substitution |
|---|---|---|
| 1 | | PVLKARGHDE or Q |
| 2 | WKCR or H | |
| 3 | | L |
| 4 | PT or Q | |
| 36 | IVH or N | |
| 37 | WLVKRTHD or E | WIFLVMATG or Q |
| 40 | FLKARTG or Q | |
| 41 | | PLVARTSHNE or Q |
| 47 | WILMTS or N | |
| 48 | FPLVMT or S | |
| 57 | WVTSGDNE or Q | |
| 58 | IYFLVMAT or Q | |
| 63 | IYPLKARS or G | |
| 68 | VMCARSG or Q | |
| 72 | | VKRTSGHD or E |
| 74 | | FPLVTGD or N |
| 81 | ILVKMAGDN or E | |
| 82c | | PLVMAG or E |
| 84 | LVARTS or G | |
| 85 | | WIYFPLMCR or G |
| 87 | IMSH or E | |
| 94 | | TSDQLA or W |
| 100 | IPVKRT or G | |
| 103 | IYMATGHDE or Q | |
| 104 | L or G | |
| 105 | ILVTSGHNE or Q | |
| 106 | YLVKMRT or D | |
| 106a | PLVTI | |
| 107 | ILVMATSGN or E | |
| 109 | I or K and | |
| 113 | PLVAT or G. | |

4. The method of claim 3, wherein the substitutions in the variable regions of the modified antibody are selected from the group consisting of

| Position | Light Chain Amino Acid Substitution | Heavy Chain Amino Acid Substitution |
|---|---|---|
| 1 | | Q |
| 2 | I | M |
| 3 | L or V | QR or K |
| 4 | LV or I | |
| 5 | | VD or E |
| 6 | | Q or D |
| 7 | IAD or S | T |
| 8 | A or E | E |
| 9 | F or P | |
| 10 | T | D or A |
| 11 | N or V | V or F |
| 12 | S | I |
| 13 | | K or E |
| 14 | T or S | |
| 15 | PFI or L | |
| 16 | | RS or E |
| 17 | TEQ or D | P or A |
| 18 | PS or Q | |
| 19 | V | R or K |
| 20 | | V |
| 23 | | TS or E |
| 24 | | V |
| 28 | | AINS or T |
| 36 | YL or F | |
| 37 | Q | |
| 39 | R | |
| 40 | P or S | VA or S |
| 41 | | T or S |
| 42 | | G or E |
| 43 | P | |
| 44 | | S or R |
| 45 | EQR or K | |
| 46 | R or V | Q |
| 47 | V | |
| 48 | | ST or G |
| 49 | S | |
| 59 | S | |
| 60 | N | |
| 61 | T | |
| 63 | T | |
| 64 | D | |
| 67 | A | |
| 68 | GD or E | I or S |
| 70 | | L |
| 72 | | N |
| 73 | | N or D |
| 74 | NLR or E | A |
| 75 | L | E or N |
| 76 | I or T | NTRK or S |
| 77 | S | TNIVSM or R |
| 78 | AL or I | LA or V |
| 79 | QG or Q | F or H |
| 80 | P | |
| 81 | | E |
| 82a | | SDN or I |
| 82b | | I or R |
| 83 | MV or L | EK or T |
| 84 | | SPVT or I |
| 85 | IM or V | D |
| 87 | YL or F | M |
| 88 | | A or G |
| 89 | | ITVM or L |
| 90 | | H or F |
| 93 | | ASHAV or T |
| 94 | | R or G |
| 100 | AS or Q | |
| 103 | N or R | A |
| 104 | V | Y or H |
| 105 | | TH or R |
| 106 | | |
| 107 | R | A or Q |
| 108 | | STG or M |
| 109 | | L or T |
| 110 | | S or L |
| 112 | | T and |
| 113 | | S or A. |

5. The method of claim 4, wherein the substitutions in the variable regions of the modified antibody are selected from the group consisting of

| Position | Light Chain Amino Acid Substitution | Heavy Chain Amino Acid Substitution |
|---|---|---|
| 3 | | Q or K |
| 5 | | V or E |
| 7 | S or T | |
| 13 | | Q or K |
| 14 | T or S | |
| 15 | P or L | |
| 17 | E or D | |
| 18 | P or Q | |
| 19 | | R or K |
| 40 | P or S | A or S |
| 42 | | G or E |
| 44 | | G or R |
| 45 | Q or K | |
| 68 | G or E | |
| 74 | K or N | S or A |
| 77 | | T or R |
| 81 | | Q or E |
| 82 | | N or I |
| 82a | S or N | |
| 83 | V or L | |
| 84 | | A or S |
| 88 | A or G | |
| 89 | V or M | |
| 110 | T or S and | |
| 113 | S or A. | |

6. The method of claim 1, wherein the non-HMFG antigen-binding peptide of the modified antibody is selected from the group consisting of the constant regions of an antibody of the first species.

7. The method of claim 6, wherein the constant region of the modified antibody is selected from the group consisting of a complete constant region and Fab, Fab' and (Fab')$_2$ fragments thereof.

8. The method of claim 1, wherein the first and second antibody species are selected from the group consisting of murine, rat, goat, rabbit, canine, primate, bovine, ovine, equine, feline, pig, human and guinea pig antibodies.

9. The method of claim 8, wherein in the modified antibody the first species is murine and the second species is human.

10. The method of claim 1, wherein the therapeutic agent comprises a radiolabeled agent.

11. The method of claim 10, wherein the radiolabeled agent comprises a radionucleotide.

12. The method of claim 10, wherein the radiolabeled agent is linked to the modified antibody at a site other than the HMFG antigen-binding site.

13. The method of claim 11, wherein the radiolabeled antibody is bound to a polypeptide selected from the group consisting of the HMFG antigen and antibody binding fragments of the HFMG antigen.

14. The method of claim 11, wherein in the modified antibody the second species is non-human and the non-HMFG antigen-binding peptide is selected from the group consisting of complete human antibody constant regions, and human Fab, Fab', and (Fab')$_2$ fragments thereof.

15. The method of claim 1, wherein the modified antibody comprises the heavy chain constant region of an antibody of the first species linked to the heavy chain variable region of an antibody of the second species, and the light chain constant region of an antibody of the first species linked to the light chain variable region of an antibody of the second species wherein at least one of the variable region chains is substituted.

16. The method of claim 15, wherein the light and heavy chains of the variable regions of the modified antibody are linked to one another at a site other than the antigen binding site.

17. The method of claim 1, wherein the modified antibody competes with the antibody expressed by the hybridoma cell ATCC No. HB 10028 for binding to the HMFG antigen.

18. The method of claim 1, wherein in the modified antibody the light chain of the antibody variable region is substituted at 1 to 8 positions.

19. The method of claim 18, wherein in the modified antibody the light chain of the antibody variable region is substituted at a position selected from the group consisting of positions 7, 14, 15, 17, 18, 40, 45, 68, 74 and 83.

20. The method of claim 19, wherein in the modified antibody the light chain of the antibody variable region is substituted with S, T, P, E, P, P, G, and V at positions 7, 14, 15, 17, 18, 40, 68, and 83, respectively.

21. The method of claim 1, wherein in the modified antibody the heavy chain of the antibody variable region is substituted at 1 to 12 positions.

22. The method of claim 21, wherein in the modified antibody the heavy chain of the antibody variable region is substituted at a position selected from the group consisting of 3, 5, 13, 19, 40, 42, 44, 74, 77, 81, 82, 82a, 84, 88, 89, 110 and 113.

23. The method of claim 22, wherein in the modified antibody the heavy chain of the antibody variable region is substituted with Q, V, R, G, T, N, A, and S at positions 3, 5, 19, 42, 77, 82, 88 and 113, respectively.

24. The method of claim 1, wherein in the modified antibody
the HMFG antigen-binding peptide is encoded by a nucleic acid that comprises a sequence selected from the group consisting of SEQ. ID No: 64 and SEQ. ID No: 65, and
the non-HMFG antigen-binding peptide comprises the light and heavy chains of a human antibody constant region, each chain being linked to one sequence at a site other than the HMFG antigen-binding site.

25. The method of claim 1, wherein in the modified antibody
the HMFG antigen-binding peptide comprises SEQ. ID Nos: 67 through 73, each sequence being linked to one another at sites other than the HMFG antigen-binding site, and
the non-HMFG antigen-binding peptide comprises light and heavy chains of a human antibody constant region, each chain being linked to one of the sequences at a site other than the HMFG antigen-binding site.

26. The method of claim 1, wherein the modified antibody comprises a polypeptide selected from the group consisting of
SEQ. ID No: 13 linked to the heavy chain of a human antibody constant region at a site other than the HMFG antigen-binding site, and
SEQ. ID NOS: 67 to 73; wherein SEQ. ID NOS:67 to 73 are linked to one another, and one of them is also linked to the light chain of a human antibody constant region at a site other than the HMFG antigen-binding site.

27. The method of claim 1, wherein the modified antibody comprises a polypeptide selected from the group consisting of
SEQ. ID No: 11 linked to the light chain of a human antibody constant region at a site other than the HMFG antigen-binding site; and SEQ. ID Nos: 75 to 81; wherein SEQ. ID NOS:75 to 81 are linked to one another, and one of them is also linked to the heavy chain of a human antibody constant region at a site other than the HMFG antigen-binding site.

28. The method of claim 1, wherein the modified antibody comprises a polypeptide selected from the group consisting of SEQ. ID Nos: 67 to 73; wherein SEQ. ID NO:67 to 73 are linked to one another, and one of them is also linked to the light chain of a human antibody constant region at a site other than the HMFG antigen-binding site; and SEQ. ID Nos: 75 to 81; wherein SEQ. ID NOS: 75 to 81 are linked to one another, and one of them is also linked to the heavy chain of a human antibody constant region at a site other than the HMFG antigen-binding site.

29. The method of claim 1, wherein the modified antibody is the antibody expressed by the hybridoma cell ATCC No. HB 11200.

30. The method of claim 29, wherein the modified antibody comprises Fab, $Fab^1$ or $(Fab^1)_2$.

31. The method of claim 1, wherein the modified antibody comprises a polypeptide selected from the group consisting of the heavy chain constant region of an antibody of the first species linked to the heavy chain variable region of an antibody of the second species at a site other than the HMFG antigen-binding site; and the light chain constant region of an antibody of the first species linked to the light chain variable region of an antibody of the second species at a site other than the HMFG antigen-binding site; wherein at least one of the chains of the variable region is substituted.

32. The method of claim 31, wherein in the modified antibody the first species is human and the second species is murine.

33. The method of claim 31, wherein the heavy chain variable region of the modified antibody has 1 to 46 substituted amino acids.

34. The method of claim 31, wherein the light chain variable region of the modified antibody has 1 to 46 substituted amino acid.

35. The method of claim 1, wherein a heavy chain constant region of an antibody of the first species is linked to the heavy chain variable region of an antibody of a second species at a site other than the HMFG antigen-binding site, the heavy chain variable region having 1 to 46 substituted amino acids; and a light chain constant region of an antibody of the first species is linked to the light chain variable region of an antibody of the second species at a site other than the HMFG antigen-binding site.

36. The method of claim 35, wherein in the modified antibody the first species is human and the second species is murine.

37. The method of claim 1, wherein the modified antibody is the antibody expressed by the hybridoma cell ATCC No. HB 11486.

38. The method of claim 32, wherein the modified antibody comprises Fab, $Fab^1$ or $(Fab^1)_2$ fragments.

39. The method of claim 1, wherein the modified antibody is the antibody expressed by the hybridoma cell ATCC No. HB 11487.

40. The method of claim 39, wherein the modified antibody comprises Fab, $Fab^1$ or $(Fab^1)_2$ fragments.

41. The method of claim 1, wherein in the modified antibody the variable region of the light chain is that expressed by the hybridoma cell line ATCC No. HB 10028.

42. The method of claim 41, wherein the variable region of the heavy chain of the modified antibody is that expressed by the hybridoma cell ATCC HB 11486.

43. The method of claim 41, wherein the variable region of the heavy chain of the modified antibody is that expressed by the hybridoma cell ATCC HB 11487.

44. The method of claim 41, wherein the variable region of the heavy chain of the modified antibody is that expressed by the hybridoma cell ATCC HB 11200.

45. The method of claim 1, wherein in the modified antibody the variable region of the heavy chain is that expressed by the hybridoma cell line ATCC No. HB 10028.

46. The method of claim 45, wherein the variable region of the light chain of the modified antibody is that expressed by the hybridoma cell ATCC HB 11486.

47. The method of claim 45, wherein the variable region of the light chain of the modified antibody is that expressed by the hybridoma cell ATCC HB 11487.

48. The method of claim 45, wherein the variable region of the light chain of the modified antibody is that expressed by the hybridoma cell ATCC HB 11200.

49. The method of claim 1, wherein the modified antibody is glycosylated.

50. The method of claim 1, wherein the modified antibody is provided as a composition further comprising a non-proteolytic carrier.

51. The method of claim 50, wherein the carrier in the composition is a pharmaceutically-acceptable carrier.

52. The method of claim 1, wherein the modified antibody is obtained by cloning SEQ. ID Nos: 64 and 65 into an expression vector;

cloning a set of polynucleotides encoding the constant region of a human antibody into an expression vector;

transfecting a host cell with the vectors;

culturing the transfected cell in an expression medium, allowing the expression of the modified antibody; and isolating the modified antibody.

53. The method of claim 1, wherein the modified antibody is obtained by a method comprising cloning first set of polynucleotides encoding the variable region light and heavy chains of the HMFG antigen-binding peptides, into an expression vector wherein at least one of the chains has 1 to 46 amino acid substitutions;

cloning second set of polynucleotides encoding the constant region light and heavy chains of the non-HMFG antigen-binding peptide into an expression vector;

transfecting a host cell with the vectors;

culturing the transfected cell in an expression medium;

allowing the expression of the modified antibody; and isolating the modified antibody.

54. The method of claim 1, wherein the modified antibody comprises the heavy chain constant region of an antibody of the first species linked to the heavy chain variable region of an antibody of the second species at a site other than the HMFG antigen-binding site; and the light chain constant region of an antibody of the first species linked to the light chain variable region of an antibody of the second species at a site other than the HMFG antigen-binding site, the light chain variable region having 1 to 46 substituted amino acids.

55. The method of claim 54, wherein in the modified antibody the first species is human and the second species is murine.

56. The method of claim 1, wherein the modified antibody is obtained by
  obtaining the sequences of a set of polynucleotides encoding the variable region light and heavy chains of an HMFG antigen-binding antibody of a first species;
  substituting nucleotide(s) of the sequences of the set of polynucleotides which encode the 1 to 46 substituted amino acids;
  transfecting, with the modified polynucleotide set, a host cell comprising a second set of polynucleotides encoding the constant region of a non-HMFG antigen-binding antibody of a second species;
  culturing the transfected cell in an expression medium;
  allowing the expression of the modified antibody; and
  isolating the modified antibody.

57. The method of claim 56, wherein the modified antibody is further recovered from the medium.

58. The method of claim 1, wherein the modified antibody is bound to the tumor reducing or tumorcidal agent at a site other than the antigen binding site prior to administration.

59. The method of claim 1, wherein the modified antibody is non-glycosylated.

60. The method of claim 1, wherein the light and heavy chains of the variable region of the modified antibody are those expressed by the hybridoma cell line ATCC No. HB 10028.

61. The method of claim 1, wherein the modified antibody is administered in an amount of about 0.001 to 5000 μg/kg weight per treatment.

62. The method of claim 61, wherein the modified antibody is administered in an amount of about 0.001 to about 2000 μg/kg body weight per treatment.

63. The method of claim 1, wherein the modified antibody is administered by injection.

64. The method of claim 1, further comprising administering to the subject an amount of an anti-idiotype antibody or binding fragment thereof effective to bind any residual or unbound circulating modified antibody and thereby accelerate the clearance of the modified antibody.

65. The method of claim 1, wherein the subject is suspected of being afflicted with a primary or metastasized carcinoma, and the effectiveness of treatment for primary or metastasized carcinoma is followed by detecting any amount of radiolabeled modified antibody-antigen complexes formed by imaging and, thereby, follow the progress of the treatment.

* * * * *

SEQUENCE LISTING (1) GENERAL INFORMATION:

(iii) NUMBER OF SEQUENCES: 96

(2) INFORMATION FOR SEQ ID NO:1:

(i) SEQUENCE CHARACTERISTICS:
      (A) LENGTH:    27 base pairs
      (B) TYPE:      nucleic acid
      (C) STRANDEDNESS:single
      (D) TOPOLOGY:  linear (ii) MOLECULE TYPE:    DNA (genomic)

(xi) SEQUENCE DESCRIPTION: SEQ ID NO:1:

TGAAGCTTGC TCACTGGATG GTGGGAA                                27

(2) INFORMATION FOR SEQ ID NO:2:

(i) SEQUENCE CHARACTERISTICS:
        (A) LENGTH:    20 base pairs
        (B) TYPE:      nucleic acid
        (C) STRANDEDNESS: single
        (D) TOPOLOGY:  linear (ii) MOLECULE TYPE: DNA (genomic)

(xi) SEQUENCE DESCRIPTION: SEQ ID NO:2:

AGATGGGGGT GTCGTTTTGG                                          20

(2) INFORMATION FOR SEQ ID NO:3:

(i) SEQUENCE CHARACTERISTICS:
        (A) LENGTH:    28 base pairs
        (B) TYPE:      nucleic acid
        (C) STRANDEDNESS: single
        (D) TOPOLOGY:  linear (ii) MOLECULE TYPE: DNA (genomic)

(xi) SEQUENCE DESCRIPTION: SEQ ID NO:3:

GCTTGAATTC CAGGGGCCAG TGGATAGA                                 28

(2) INFORMATION FOR SEQ ID NO:4:

(i) SEQUENCE CHARACTERISTICS:
        (A) LENGTH:    22 base pairs
        (B) TYPE:      nucleic acid
        (C) STRANDEDNESS: single
        (D) TOPOLOGY:  linear (ii) MOLECULE TYPE: DNA (genomic)

(ix) FEATURE:
        (D) OTHER INFORMATION: S represents C or G, M represents A or
            C, W represents T or A.

(xi) SEQUENCE DESCRIPTION: SEQ ID NO:4:

AGGTBHAHCT GCAGBAGTCW GG                                       22

(2) INFORMATION FOR SEQ ID NO:5:

(i) SEQUENCE CHARACTERISTICS:
        (A) LENGTH:    26 base pairs
        (B) TYPE:      nucleic acid
        (C) STRANDEDNESS: single
        (D) TOPOLOGY:  linear (ii) MOLECULE TYPE: DNA (genomic)

(xi) SEQUENCE DESCRIPTION: SEQ ID NO:5:

ATGTACTTGG GACTGAACTA TGTCTT                                   26

(2) INFORMATION FOR SEQ ID NO:6:

(i) SEQUENCE CHARACTERISTICS:
        (A) LENGTH:    41 base pairs
        (B) TYPE:      nucleic acid
        (C) STRANDEDNESS: single
        (D) TOPOLOGY:  linear (ii) MOLECULE TYPE: DNA (genomic)

(xi) SEQUENCE DESCRIPTION: SEQ ID NO:6:

GGGGATATCC ACCATGTACT TGGGACTGAA CTATGTCTTC A                  41

(2) INFORMATION FOR SEQ ID NO:7:

(i) SEQUENCE CHARACTERISTICS:
    (A) LENGTH:    39 base pairs
    (B) TYPE:      nucleic acid
    (C) STRANDEDNESS: single
    (D) TOPOLOGY:  linear (ii) MOLECULE TYPE: DNA (genomic)

(xi) SEQUENCE DESCRIPTION: SEQ ID NO:7:

GGGGATATCC ACCATGAAGT TGCCTGTTAG GCTGTTGGT                    39

(2) INFORMATION FOR SEQ ID NO:8:

(i) SEQUENCE CHARACTERISTICS:
        (A) LENGTH:    32 base pairs
        (B) TYPE:      nucleic acid
        (C) STRANDEDNESS: single
        (D) TOPOLOGY:  linear (ii) MOLECULE TYPE: DNA (genomic)

(xi) SEQUENCE DESCRIPTION: SEQ ID NO:8:

GGGGCTAGCT GCAGAGACAG TGACCAGAGT CC                          32

(2) INFORMATION FOR SEQ ID NO:9:

(i) SEQUENCE CHARACTERISTICS:
        (A) LENGTH:    39 base pairs
        (B) TYPE:      nucleic acid
        (C) STRANDEDNESS: single
        (D) TOPOLOGY:  linear (ii) MOLECULE TYPE: DNA (genomic)

(xi) SEQUENCE DESCRIPTION: SEQ ID NO:9:

GGGGTCGACT TACGTTTGAT TTCCAGCTTG GTGCCTCCA                    39

(2) INFORMATION FOR SEQ ID NO:10:

(i) SEQUENCE CHARACTERISTICS:
        (A) LENGTH:    394 base pairs
        (B) TYPE:      nucleic acid
        (C) STRANDEDNESS: single
        (D) TOPOLOGY:  linear (ii) MOLECULE TYPE: DNA (genomic)

(xi) SEQUENCE DESCRIPTION: SEQ ID NO:10:

ATGAAGTTGC CTGTTAGGCT GTTGGTGCTG TTGTTCTGGA                   40

TTCCTGCTTC CATCAGTGAT GTTGTGATGA CCCAAACTCC                   80

ACTCTCCCTG CCTGTCAGTC TTGGAGATCA AGCTTCCATC                   120

TCTTGCAGAT CTAGTCAGAA CCTTGTACAC AACAATGGAA                   160

ACACCTATTT ATATTGGTTC CTGCAGAAGT CAGGCCAGTC                   200

TCCAAAGCTC CTGATTTATA GGGCTTCCAT CCGATTTTCT                   240

GGGGTCCCAG ACAGGTTCAG TGGCAGTGGA TCAGAGACAG                   280

ATTTCACACT CAAGATCAGC AGAGTGGAGG CTGAGGATCT                   320

GGGAGTTTAT TTCTGCTTTC AAGGTACACA TGTTCCGTGG                   360

ACGTTCGGTG GAGGCACCAA GCTGGAAATC AAAC                         394

(2) INFORMATION FOR SEQ ID NO:11:

(i) SEQUENCE CHARACTERISTICS:

(A) LENGTH:    131 amino acids
        (B) TYPE:      amino acid
        (D) TOPOLOGY:  linear (ii) MOLECULE TYPE: peptide (xi) SEQUENCE DESCRIPTION: SEQ ID NO:11:

Met Lys Leu Pro Val Arg Leu Leu Val Leu Leu Phe Trp
1               5                   10

Ile Pro Ala Ser Ile Ser Asp Val Val Met Thr Gln Thr
    15                  20                  25

Pro Leu Ser Leu Pro Val Ser Leu Gly Asp Gln Ala Ser
                30                  35

Ile Ser Cys Arg Ser Ser Gln Asn Leu Val His Asn Asn
40                  45                  50

Gly Asn Thr Tyr Leu Tyr Trp Phe Leu Gln Lys Ser Gly
        55                  60                  65

Gln Ser Pro Lys Leu Leu Ile Tyr Arg Ala Ser Ile Arg
                70                  75

Phe Ser Gly Val Pro Asp Arg Phe Ser Gly Ser Gly Ser
    80                  85                  90

Glu Thr Asp Phe Thr Leu Lys Ile Ser Arg Val Glu Ala
            95                  100

Glu Asp Leu Gly Val Tyr Phe Cys Phe Gln Gly Thr His
105                 110                 115

Val Pro Trp Thr Phe Gly Gly Gly Thr Lys Leu Glu Ile
                120                 125                 130

Lys
131

(2) INFORMATION FOR SEQ ID NO:12:

(i) SEQUENCE CHARACTERISTICS:
        (A) LENGTH:       403 base pairs
        (B) TYPE:         nucleic acid
        (C) STRANDEDNESS: single
        (D) TOPOLOGY:     linear (ii) MOLECULE TYPE: DNA (genomic)

(xi) SEQUENCE DESCRIPTION: SEQ ID NO:12:

ATGTACTTGG GACTGAACTA TGTCTTCATA GTTTTTCTCT                    40

TAAAAGGTGT CCAGAGTGAA GTGAAGCTTG AGGAGTCTGG                    80

AGGAGGCTTG GTGCAACCTG GAGGATCCAT GAAACTCTCT                   120

TGTGCTGCTT CTGGATTCAC TTTTAGTGAT GCCTGGATGG                   160

ACTGGGTCCG CCAGTCTCCA GAGAAGGGGC TTGAGTGGGT                   200

TGCTGAAATT AGAAACAAAG CCAATAATCA TGCAACATAT                   240

TATGATGAGT CTGTGAAAGG GAGGTTCACC ATCTCAAGAG                   280

ATGATTCCAA AAGTAGAGTG TACCTGCAAA TGATAAGCTT                   320

AAGAGCTGAA GACACTGGCC TTTATTACTG TACTGGGGAG                   360

TTTGCTAACT GGGGCCAGGG GACTCTGGTC ACTGTCTCTG                   400

CAG                                                           403

(2) INFORMATION FOR SEQ ID NO:13:

```
    (i) SEQUENCE CHARACTERISTICS:
        (A) LENGTH:      134 amino acids
        (B) TYPE:        amino acid
        (D) TOPOLOGY:    linear (ii) MOLECULE TYPE:      peptide (xi) SEQUENCE DESCRIPTION: SEQ ID NO:13:

Met Tyr Leu Gly Leu Asn Tyr Val Phe Ile Val Phe Leu
1               5                   10

Leu Lys Gly Val Gln Ser Glu Val Lys Leu Glu Glu Ser
        15                  20                  25

Gly Gly Gly Leu Val Gln Pro Gly Gly Ser Met Lys Leu
                30                  35

Ser Cys Ala Ala Ser Gly Phe Thr Phe Ser Asp Ala Trp
40                  45                  50

Met Asp Trp Val Arg Gln Ser Pro Glu Lys Gly Leu Glu
        55                  60                  65

Trp Val Ala Glu Ile Arg Asn Lys Ala Asn Asn His Ala
                70                  75

Thr Tyr Tyr Asp Glu Ser Val Lys Gly Arg Phe Thr Ile
        80                  85                  90

Ser Arg Asp Asp Ser Lys Ser Arg Val Tyr Leu Gln Met
        95                  100

Ile Ser Leu Arg Ala Glu Asp Thr Gly Leu Tyr Tyr Cys
105                 110                 115

Thr Gly Glu Phe Ala Asn Trp Gly Gln Gly Thr Leu Val
        120                 125                 130

Thr Val Ser Ala
        134

(2) INFORMATION FOR SEQ ID NO:14:

(i) SEQUENCE CHARACTERISTICS:
        (A) LENGTH:      40 base pairs
        (B) TYPE:        nucleic acid
        (C) STRANDEDNESS: single
        (D) TOPOLOGY:    linear (ii) MOLECULE TYPE:      DNA (genomic)

(xi) SEQUENCE DESCRIPTION: SEQ ID NO:14:

ACTAGTCGAC ATGAAGTTGC CTGTTAGGCT GTTGGTGCTG                                    40

(2) INFORMATION FOR SEQ ID NO:15:

(i) SEQUENCE CHARACTERISTICS:
        (A) LENGTH:      39 base pairs
        (B) TYPE:        nucleic acid
        (C) STRANDEDNESS: single
        (D) TOPOLOGY:    linear (ii) MOLECULE TYPE:      DNA (genomic)

(xi) SEQUENCE DESCRIPTION: SEQ ID NO:15:

ACTAGTCGAC ATGGAGWCAGA CACACTCCTG YTATGGGT                                     39

(2) INFORMATION FOR SEQ ID NO:16:

(i) SEQUENCE CHARACTERISTICS:
        (A) LENGTH:      40 base pairs
        (B) TYPE:        nucleic acid
        (C) STRANDEDNESS: single
```

```
        (D) TOPOLOGY:  linear (ii) MOLECULE TYPE:   DNA (genomic)

(xi) SEQUENCE DESCRIPTION: SEQ ID NO:16:

ACTAGTCGAC ATGGATTTWC AGGTGCAGATT TWCAGCTTC                          40

(2) INFORMATION FOR SEQ ID NO:17:

(i) SEQUENCE CHARACTERISTICS:
        (A) LENGTH:    30 base pairs
        (B) TYPE:      nucleic acid
        (C) STRANDEDNESS: single
        (D) TOPOLOGY:  linear (ii) MOLECULE TYPE:   DNA (genomic)

(xi) SEQUENCE DESCRIPTION: SEQ ID NO:17:

CCCAAGCTTA CTGGATGGTG GGAAGATGGA                                    30

(2) INFORMATION FOR SEQ ID NO:18:

(i) SEQUENCE CHARACTERISTICS:
        (A) LENGTH:    35 base pairs
        (B) TYPE:      nucleic acid
        (C) STRANDEDNESS: single
        (D) TOPOLOGY:  linear (ii) MOLECULE TYPE:   DNA (genomic)

(xi) SEQUENCE DESCRIPTION: SEQ ID NO:18:

ACTAGTCGAC ATGRACTTTG GGYTCAGCTT GRTTT                              35

(2) INFORMATION FOR SEQ ID NO:19:

(i) SEQUENCE CHARACTERISTICS:
        (A) LENGTH:    33 base pairs
        (B) TYPE:      nucleic acid
        (C) STRANDEDNESS: single
        (D) TOPOLOGY:  linear (ii) MOLECULE TYPE:   DNA (genomic)

(xi) SEQUENCE DESCRIPTION: SEQ ID NO:19:

ACTAGTCGAC ATGAGAGTGC TGATTCTTTT GTG                                33

(2) INFORMATION FOR SEQ ID NO:20:

(i) SEQUENCE CHARACTERISTICS:
        (A) LENGTH:    38 base pairs
        (B) TYPE:      nucleic acid
        (C) STRANDEDNESS: single
        (D) TOPOLOGY:  linear (ii) MOLECULE TYPE:   DNA (genomic)

(xi) SEQUENCE DESCRIPTION: SEQ ID NO:20:

ACTAGTCGAC ATGGATTTTG GGCTGATTTT TTTTATTG                           38

(2) INFORMATION FOR SEQ ID NO:21:

(i) SEQUENCE CHARACTERISTICS:
        (A) LENGTH:    35 base pairs
        (B) TYPE:      nucleic acid
        (C) STRANDEDNESS: single
        (D) TOPOLOGY:  linear (ii) MOLECULE TYPE:   DNA (genomic)
```

```
    (ix) FEATURE:
         (D) OTHER INFORMATION: N represents inosine.

(xi) SEQUENCE DESCRIPTION: SEQ ID NO:21:

CCCAAGCTTC CAGGGRCCAR KGGATARACN GRTGG                              35

(2) INFORMATION FOR SEQ ID NO:22:

(i) SEQUENCE CHARACTERISTICS:
        (A) LENGTH:    37 base pairs
        (B) TYPE:      nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO:22:

GGGGATATCC ACCATGAAGT TGCCTGTTAG GCTGTTG                            37

(2) INFORMATION FOR SEQ ID NO:23:

(i) SEQUENCE CHARACTERISTICS:
        (A) LENGTH:    39 base pairs
        (B) TYPE:      nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO:23:

CCCGTCGACT TACGTTTTAT TTCCAGCTTG GTCCCCCCT                          39

(2) INFORMATION FOR SEQ ID NO:24:

(i) SEQUENCE CHARACTERISTICS:
        (A) LENGTH:    39 base pairs
        (B) TYPE:      nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO:24:

GGGGATATCC ACCATGGACT TTGGGCTCAG CTTGGTTTT                          39

(2) INFORMATION FOR SEQ ID NO:25:

(i) SEQUENCE CHARACTERISTICS:
        (A) LENGTH:    32 base pairs
        (B) TYPE:      nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO:25:

CCCGCTAGCT GCAGAGACAG AGACCAGAGT CC                                 32

(2) INFORMATION FOR SEQ ID NO:26:

(i) SEQUENCE CHARACTERISTICS:
        (A) LENGTH:    394 base pairs
        (B) TYPE:      nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO:26:
```

-continued

```
ATGAAGTTGC CTGTTAGGCT GTTGGTGCTG ATGTTCTGGA            40

TTCCTGCTTC CAGCAGTGAT GTTTTGATGA CCCAAACTCC            80

TCTCTCCCTG CCTGTCAGTC TTGGAGATCA AGCCTCCATC           120

TCTTGCAGAT CTAGTCAGAG CATTGTACAT AGTAATGGAA           160

ACACCTATTT AGAATGGTAC CTGCAGAAAC CAGGCCAGTC           200

TCCAAAGCTC CTGATCTACA AAGTTTCCAT CCGATTTTCT           240

GGGGTCCCAG ACAGGTTCAG TGGCAGTGGA TCAGGGACAG           280

ATTTCACACT CAATATCAGC AGAGTGGAGG CTGAGGATCT           320

GGGAATTTAT TACTGCTTTC AAGGTTCACA TGTTCCGTAC           360

ACGTTCGGAG GGGGGACCAA GCTGGAAATA AAAC                 394
```

(2) INFORMATION FOR SEQ ID NO:27:

(i) SEQUENCE CHARACTERISTICS:
        (A) LENGTH:    418 base pairs
        (B) TYPE:      nucleic acid
        (C) STRANDEDNESS: single
        (D) TOPOLOGY:  linear (ii) MOLECULE TYPE:     DNA (genomic)

(xi) SEQUENCE DESCRIPTION: SEQ ID NO:27:

```
ATGGACTTTG GGCTCAGCTT GGTTTTCCTT GTCCTTATTT            40

TAAAAGGTGT CCAGTGTGAA GTGCAGATGG TGGAGTCTGG            80

GGGAGGCTTA GTGAAGCCTG GAGGGTCCCT GAAACTCTCC           120

TGTGCAGCCT CTGGATTCGC TTTCAGTAGC TATGCCATGT           160

CTTGGGTTCG CCAGTCTCCA GAGAAGAGGC TGGAGTGGGT           200

CGCAGAAATT AGTAGTGGTG GTAATTACGC CTACTATCAA           240

GACACTGTGA CGGGCCGATT CACCATCTCC AGAGACAATG           280

CCAAGAACAC CCTGTACCTG GAAATGAGCA GTCTGAGGTC           320

TGAGGACACG GCCATGTATT ACTGTGCAAG GGAGGACTAC           360

GGTATCCCGG CCTGGTTTGC TTACTGGGGC CAAGGGACTC           400

TGGTCTCTGT CTCTGCAG                                   418
```

(2) INFORMATION FOR SEQ ID NO:28:

(i) SEQUENCE CHARACTERISTICS:
        (A) LENGTH:    19 amino acids
        (B) TYPE:      amino acid
        (D) TOPOLOGY:  linear (ii) MOLECULE TYPE:     peptide (xi) SEQUENCE DESCRIPTION: SEQ ID NO:28:

```
Met Lys Leu Pro Val Arg Leu Leu Val Leu Met Phe Trp
1               5                   10

Ile Pro Ala Ser Ser Ser
        15              19
```

(2) INFORMATION FOR SEQ ID NO:29:

(i) SEQUENCE CHARACTERISTICS:
        (A) LENGTH:    23 amino acids (B) TYPE:      amino acid
                (D) TOPOLOGY:  linear (ii) MOLECULE TYPE:    peptide (xi) SEQUENCE DESCRIPTION: SEQ ID NO:29:

Asp Val Leu Met Thr Gln Thr Pro Leu Ser Leu Pro Val
1               5                  10

Ser Leu Gly Asp Gln Ala Ser Ile Ser Cys
        15                  20          23

(2) INFORMATION FOR SEQ ID NO:30:

(i) SEQUENCE CHARACTERISTICS:
                (A) LENGTH:    16 amino acids
                (B) TYPE:      amino acid
                (D) TOPOLOGY:  linear (ii) MOLECULE TYPE:    peptide (xi) SEQUENCE DESCRIPTION: SEQ ID NO:30:

Arg Ser Ser Gln Ser Ile Val His Ser Asn Gly Asn Thr
1               5                  10

Tyr Leu Glu
        15

(2) INFORMATION FOR SEQ ID NO:31:

(i) SEQUENCE CHARACTERISTICS:
                (A) LENGTH:    15 amino acids
                (B) TYPE:      amino acid
                (D) TOPOLOGY:  linear (ii) MOLECULE TYPE:    peptide (xi) SEQUENCE DESCRIPTION: SEQ ID NO:31:

Trp Tyr Leu Gln Lys Pro Gly Gln Ser Pro Lys Leu Leu
1               5                  10

Ile Tyr
        15

(2) INFORMATION FOR SEQ ID NO:32:

(i) SEQUENCE CHARACTERISTICS:
                (A) LENGTH:    7 amino acids
                (B) TYPE:      amino acid
                (D) TOPOLOGY:  linear (ii) MOLECULE TYPE:    peptide (xi) SEQUENCE DESCRIPTION: SEQ ID NO:32:

Lys Val Ser Ile Arg Phe Ser
1               5

(2) INFORMATION FOR SEQ ID NO:33:

(i) SEQUENCE CHARACTERISTICS:
                (A) LENGTH:    32 amino acids
                (B) TYPE:      amino acid
                (D) TOPOLOGY:  linear (ii) MOLECULE TYPE:    peptide (xi) SEQUENCE DESCRIPTION: SEQ ID NO:33:

Gly Val Pro Asp Arg Phe Ser Gly Ser Gly Ser Gly Thr
1               5                  10

```
Asp Phe Thr Leu Asn Ile Ser Arg Val Glu Ala Glu Asp
    15                  20                  25

Leu Gly Ile Tyr Tyr Cys
            30
```

(2) INFORMATION FOR SEQ ID NO:34:

(i) SEQUENCE CHARACTERISTICS:
        (A) LENGTH:    9 amino acids
        (B) TYPE:      amino acid
        (D) TOPOLOGY:  linear (ii) MOLECULE TYPE:     peptide (xi) SEQUENCE DESCRIPTION: SEQ ID NO:34:

```
Phe Gln Gly Ser His Val Pro Tyr Thr
1               5
```

(2) INFORMATION FOR SEQ ID NO:35:

(i) SEQUENCE CHARACTERISTICS:
        (A) LENGTH:    10 amino acids
        (B) TYPE:      amino acid
        (D) TOPOLOGY:  linear (ii) MOLECULE TYPE:     peptide (xi) SEQUENCE DESCRIPTION: SEQ ID NO:35:

```
Phe Gly Gly Gly Thr Lys Leu Glu Ile Lys
1               5                   10
```

(2) INFORMATION FOR SEQ ID NO:36:

(i) SEQUENCE CHARACTERISTICS:
        (A) LENGTH:    19 amino acids
        (B) TYPE:      amino acid
        (D) TOPOLOGY:  linear (ii) MOLECULE TYPE:     peptide (xi) SEQUENCE DESCRIPTION: SEQ ID NO:36:

```
Met Asp Phe Gly Leu Ser Leu Val Phe Leu Val Leu Ile
1               5                   10

Leu Lys Gly Val Gln Cys
    15
```

(2) INFORMATION FOR SEQ ID NO: 37:

(i) SEQUENCE CHARACTERISTICS:
        (A) LENGTH:    30 amino acids
        (B) TYPE:      amino acid
        (D) TOPOLOGY:  linear (ii) MOLECULE TYPE:     DNA (genomic)

(xi) SEQUENCE DESCRIPTION: SEQ ID NO: 37:

```
Glu Val Gln Met Val Glu Ser Gly Gly Leu Val Lys
1               5                   10

Pro Gly Gly Ser Leu Lys Leu Ser Cys Ala Ala Ser Gly
    15                  20                  25

Phe Ala Phe Ser
            30
```

(2) INFORMATION FOR SEQ ID NO:38:

(i) SEQUENCE CHARACTERISTICS:

```
        (A) LENGTH:      5 amino acids
        (B) TYPE:        amino acid
        (D) TOPOLOGY:    linear (ii) MOLECULE TYPE:      peptide (xi) SEQUENCE DESCRIPTION: SEQ ID NO:38:

Ser Tyr Ala Met Ser
1               5

(2) INFORMATION FOR SEQ ID NO:39:

(i) SEQUENCE CHARACTERISTICS:
        (A) LENGTH:      14 amino acids
        (B) TYPE:        amino acid
        (D) TOPOLOGY:    linear (ii) MOLECULE TYPE:      peptide (xi) SEQUENCE DESCRIPTION: SEQ ID NO:39:

Trp Val Arg Gln Ser Pro Glu Lys Arg Leu Glu Trp Val
1               5                   10
Ala
14

(2) INFORMATION FOR SEQ ID NO:40:

(i) SEQUENCE CHARACTERISTICS:
        (A) LENGTH:      17 amino acids
        (B) TYPE:        amino acid
        (D) TOPOLOGY:    linear (ii) MOLECULE TYPE:      peptide (xi) SEQUENCE DESCRIPTION: SEQ ID NO:40:

Glu Ile Ser Ser Gly Gly Asn Tyr Ala Tyr Tyr Gln Asp
1               5                   10
Thr Val Thr Gly
    15

(2) INFORMATION FOR SEQ ID NO:41:

(i) SEQUENCE CHARACTERISTICS:
        (A) LENGTH:      32 amino acids
        (B) TYPE:        amino acid
        (D) TOPOLOGY:    linear (ii) MOLECULE TYPE:      peptide (xi) SEQUENCE DESCRIPTION: SEQ ID NO:41:

Arg Phe Thr Ile Ser Arg Asp Asn Ala Lys Asn Thr Leu
1               5                   10
Tyr Leu Glu Met Ser Ser Leu Arg Ser Glu Asp Thr Ala
    15              20                  25
Met Tyr Tyr Cys Ala Arg
        30

(2) INFORMATION FOR SEQ ID NO:42:

(i) SEQUENCE CHARACTERISTICS:
        (A) LENGTH:      11 amino acids
        (B) TYPE:        amino acid
        (D) TOPOLOGY:    linear (ii) MOLECULE TYPE:      peptide (xi) SEQUENCE DESCRIPTION: SEQ ID NO:42:
```

```
Glu Asp Tyr Gly Ile Pro Ala Trp Phe Ala Tyr
1               5                   10
```

(2) INFORMATION FOR SEQ ID NO:43:

(i) SEQUENCE CHARACTERISTICS:
        (A) LENGTH:    11 amino acids
        (B) TYPE:      amino acid
        (D) TOPOLOGY:  linear (ii) MOLECULE TYPE:     peptide (xi) SEQUENCE DESCRIPTION: SEQ ID NO:43:

```
Trp Gly Gln Gly Thr Leu Val Ser Val Ser Ala
1               5                   10
```

(2) INFORMATION FOR SEQ ID NO:44:

(i) SEQUENCE CHARACTERISTICS:
        (A) LENGTH:    21 amino acids
        (B) TYPE:      amino acid
        (D) TOPOLOGY:  linear (ii) MOLECULE TYPE:     peptide (xi) SEQUENCE DESCRIPTION: SEQ ID NO:44:

```
Glu Val Gln Met Val Glu Ser Gly Gly Gly Leu Val Lys
1               5                   10
Pro Gly Gly Ser Leu Lys Leu Ser
        15                  20
```

(2) INFORMATION FOR SEQ ID NO:45:

(i) SEQUENCE CHARACTERISTICS:
        (A) LENGTH:    21 amino acids
        (B) TYPE:      amino acid
        (D) TOPOLOGY:  linear (ii) MOLECULE TYPE:     peptide (ix) FEATURE:
        (D) OTHER INFORMATION:  Xaa represents a single amino acid.

(xi) SEQUENCE DESCRIPTION: SEQ ID NO:45:

```
Glu Val Gln Met Val Glu Ser Gly Gly Gly Leu Val Lys
1               5                   10
Pro Gly Gly Xaa Leu Lys Leu Ser
        15                  20
```

(2) INFORMATION FOR SEQ ID NO:46:

(i) SEQUENCE CHARACTERISTICS:
        (A) LENGTH:    21 amino acids
        (B) TYPE:      amino acid
        (D) TOPOLOGY:  linear (ii) MOLECULE TYPE:     peptide (xi) SEQUENCE DESCRIPTION: SEQ ID NO:46:

```
Asp Val Leu Met Thr Gln Thr Pro Leu Ser Leu Pro Val
1               5                   10
Ser Leu Gly Asp Gln Ala Ser Ile
        15                  20
```

(2) INFORMATION FOR SEQ ID NO:47:

```
        (i) SEQUENCE CHARACTERISTICS:
            (A) LENGTH:    21 amino acids
            (B) TYPE:      amino acid
            (D) TOPOLOGY:  linear (ii) MOLECULE TYPE:       peptide (ix) FEATURE:
            (D) OTHER INFORMATION:   wherein Xaa represents a single amino
                acid.

(xi) SEQUENCE DESCRIPTION: SEQ ID NO:47:

Asp Val Leu Met Thr Gln Thr Pro Leu Ser Leu Pro Val
1               5                  10

Xaa Xaa Gly Asp Gln Ala Ser Ile
    15                  20

(2) INFORMATION FOR SEQ ID NO:48:

(i) SEQUENCE CHARACTERISTICS:
            (A) LENGTH:    21 amino acids
            (B) TYPE:      amino acid
            (D) TOPOLOGY:  linear (ii) MOLECULE TYPE:       peptide (xi) SEQUENCE DESCRIPTION: SEQ ID NO:48:

Asp Val Leu Met Thr Gln Thr Pro Leu Ser Leu Pro Val
1               5                  10

Ser Leu Gly Asp Gln Ala Ser Ile
    15                  20

(2) INFORMATION FOR SEQ ID NO:49:

(i) SEQUENCE CHARACTERISTICS:
            (A) LENGTH:    21 amino acids
            (B) TYPE:      amino acid
            (D) TOPOLOGY:  linear (ii) MOLECULE TYPE:       peptide (xi) SEQUENCE DESCRIPTION: SEQ ID NO:49:

Asp Val Leu Met Thr Gln Thr Pro Leu Ser Leu Pro Val
1               5                  10

Ser Leu Gly Asp Gln Ala Ser Ile
    15                  20

(2) INFORMATION FOR SEQ ID NO: 50:

(i) SEQUENCE CHARACTERISTICS:
            (A) LENGTH:    51 base pairs
            (B) TYPE:      nucleic acid
            (C) STRANDEDNESS: single
            (D) TOPOLOGY:  linear (ii) MOLECULE TYPE:       DNA (genomic)

(xi) SEQUENCE DESCRIPTION: SEQ ID NO: 50 :

TCCCTGGGTC TCACTCCTGG AGAGCCAGCT TCCATCTCTT                    40

GCAGATCTAG T                                                  51

(2) INFORMATION FOR SEQ ID NO: 51:

(i) SEQUENCE CHARACTERISTICS:
            (A) LENGTH:    54 base pairs
            (B) TYPE:      nucleic acid
            (C) STRANDEDNESS: single
```

(D) TOPOLOGY:  linear (ii) MOLECULE TYPE:    DNA (genomic)

(xi) SEQUENCE DESCRIPTION: SEQ ID NO: 51:

AGCTTGGGTC TCAGGAGTGA CAGGCAGGGA GAGTGGAGAT                   40

TGGGTCATCA CAAC                                               54

(2) INFORMATION FOR SEQ ID NO: 52:

(i) SEQUENCE CHARACTERISTICS:
        (A) LENGTH:   37 base pairs
        (B) TYPE:     nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 52 :

GTTCCTGGTC TCGCCAGGCC AGTCTCCAAA GCTCCTG                      37

(2) INFORMATION FOR SEQ ID NO: 53:

(i) SEQUENCE CHARACTERISTICS:
        (A) LENGTH:   39 base pairs
        (B) TYPE:     nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 53:

TTGGAGGTCT CCCTGGCTTC TGCAGGAACC AATATAAAT                    39

(2) INFORMATION FOR SEQ ID NO: 54:

(i) SEQUENCE CHARACTERISTICS:
        (A) LENGTH:   50 base pairs
        (B) TYPE:     nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 54:

TTCACAGGTC TCATCAGCAG AGTGGAGGCT GAGGATGTGG                   40

GAGTTTATTT                                                    50

(2) INFORMATION FOR SEQ ID NO: 55:

(i) SEQUENCE CHARACTERISTICS:
        (A) LENGTH:   50 base pairs
        (B) TYPE:     nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 55:

AGCCTCGGTC TCGCTGATCT TGAGTGTGAA ATCTGTCCCT                   40

GATCCACTGC                                                    50

(2) INFORMATION FOR SEQ ID NO: 56:

(i) SEQUENCE CHARACTERISTICS:
        (A) LENGTH:   30 base pairs

```
        (B) TYPE:     nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 56:

CCTGGAGGAT CCATGAGACT CTCTTGTGCT                                30

(2) INFORMATION FOR SEQ ID NO: 57:

(i) SEQUENCE CHARACTERISTICS:
        (A) LENGTH:   33 base pairs
        (B) TYPE:     nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 57 :

GTTGGGGCTA GCAGAAGAGA CAGTGACCAG AGT                             33

(2) INFORMATION FOR SEQ ID NO: 58 :

(i) SEQUENCE CHARACTERISTICS:
        (A) LENGTH:   51 base pairs
        (B) TYPE:     nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 58:

TACCTGGGTC TCAATAGCTT AAGAGCTGAA GACACTGCCC                      40

TTTATTACTG T                                                    51

(2) INFORMATION FOR SEQ ID NO: 59 :

(i) SEQUENCE CHARACTERISTICS:
        (A) LENGTH:   51 base pairs
        (B) TYPE:     nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 59:

TTCAGCGGTC TCGCTATTCA TTTGCAGGTA CACAGTACTT                      40

TTGGAATCAT C                                                    51

(2) INFORMATION FOR SEQ ID NO: 60:

(i) SEQUENCE CHARACTERISTICS:
        (A) LENGTH:   50 base pairs
        (B) TYPE:     nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 60:

GTCCGCGGTC TCCCAGGGAA GGGGCTTGAG TGGGTTGCTG                      40

AAATTAGAAA                                                      50

(2) INFORMATION FOR SEQ ID NO: 61 :
```

```
    (i) SEQUENCE CHARACTERISTICS:
        (A) LENGTH:    49 base pairs
        (B) TYPE:      nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 61 :

CTCAAGGGTC TCCCCTGGAG ACTGGCGGAC CCAGTCCATC                40

CAGGCATCA                                                 49

(2) INFORMATION FOR SEQ ID NO: 62 :

(i) SEQUENCE CHARACTERISTICS:
        (A) LENGTH:    52 base pairs
        (B) TYPE:      nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 62:

TGAGGAGGTC TCAGGAGGCT TGGTGCAACC TGGAGGATCC                40

ATGAGACTCT CT                                             52

(2) INFORMATION FOR SEQ ID NO: 63:

(i) SEQUENCE CHARACTERISTICS:
        (A) LENGTH:    51 base pairs
        (B) TYPE:      nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 63:

GGTTGCGGTC TCCCTCCTCC AGACTCCACA AGCTGCACTT                40

CACTCTGGAC A                                              51

(2) INFORMATION FOR SEQ ID NO: 64:

(i) SEQUENCE CHARACTERISTICS:
        (A) LENGTH:    394 base pairs
        (B) TYPE:      nucleic acid
        (C) STRANDEDNESS: single
        (D) TOPOLOGY:  linear (ii) MOLECULE TYPE:    DNA (genomic)

(xi) SEQUENCE DESCRIPTION: SEQ ID NO: 64:

ATGAAGTTGC TGTTAGGCT GTTGGTGCTG TTGTTCTGGA                 40

TTCCTGCTTC CATCAGTGAT GTTGTGATGA CCCAATCTCC                80

ACTCTCCCTG CCTGTCACTC CTGGAGAGCC AGCTTCCATC                120

TCTTGCAGAT CTAGTCAGAA CCTTGTACAC AACAATGGAA                160

ACACCTATTT ATATTGGTTC CTGCAGAAGC CAGGCCAGTC                200

TCCAAAGCTC CTGATTTATA GGGCTTCCAT CCGATTTTCT                240

GGGGTCCCAG ACAGGTTCAG TGGCAGTGGA TCAGGGACAG                280

ATTTCACACT CAAGATCAGC AGAGTGGAGG CTGAGGATGT                320

GGGAGTTTAT TTCTGCTTTC AAGGTACACA TGTTCCGTGG                360
```

```
ACGTTCGGTG GAGGCACCAA GCTGGAAATC AAAC                                    394
```

(2) INFORMATION FOR SEQ ID NO: 65:

(i) SEQUENCE CHARACTERISTICS:
        (A) LENGTH: 403 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 65:

```
ATGTACTTGG GACTGAACTA TGTCTTCATA GTTTTTCTCT                               40
TAAAAGGTGT CCAGAGTGAA GTGCAGCTTG TGGAGTCTGG                               80
AGGAGGCTTG GTGCAACCTG GAGGATCCAT GAGACTCTCT                              120
TGTGCTGCTT CTGGATTCAC TTTTAGTGAT GCCTGGATGG                              160
ACTGGGTCCG CCAGTCTCCA GGGAAGGGGC TTGAGTGGGT                              200
TGCTGAAATT AGAAACAAAG CCAATAATCA TGCAACATAT                              240
TATGATGAGT CTGTGAAAGG GAGGTTCACC ATCTCAAGAG                              280
ATGATTCCAA AAGTACTGTG TACCTGCAAA TGAATAGCTT                              320
AAGAGCTGAA GACACTGCCC TTTATTACTG TACTGGGGAG                              360
TTTGCTAACT GGGGCCAGGG GACTCTGGTC ACTGTCTCTT                              400
CTG                                                                     403
```

(2) INFORMATION FOR SEQ ID NO: 66:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 66:

```
Met Lys Leu Pro Val Arg Leu Leu Val Leu Leu Phe Trp
1               5                   10
Ile Pro Ala Ser Ile Ser
         15
```

(2) INFORMATION FOR SEQ ID NO: 67:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO: 67:

```
Asp Val Val Met Thr Gln Ser Pro Leu Ser Leu Pro Val
1               5                   10
Thr Pro Gly Glu Pro Ala Ser Ile Ser Cys
         15                  20
```

(2) INFORMATION FOR SEQ ID NO: 68:

(i) SEQUENCE CHARACTERISTICS:
        (A) LENGTH: 16 amino acids
        (B) TYPE: amino acid

```
            (D) TOPOLOGY:  linear (ii) MOLECULE TYPE:      peptide (xi) SEQUENCE DESCRIPTION: SEQ ID NO: 68:

Arg Ser Ser Gln Asn Leu Val His Asn Asn Gly Asn Thr
1               5                   10

Tyr Leu Tyr
    15

(2) INFORMATION FOR SEQ ID NO: 69:

(i) SEQUENCE CHARACTERISTICS:
        (A) LENGTH:     15 amino acids
        (B) TYPE:       amino acid
        (D) TOPOLOGY:   linear (ii) MOLECULE TYPE:      peptide (xi) SEQUENCE DESCRIPTION: SEQ ID NO: 69:

Trp Phe Leu Gln Lys Pro Gly Gln Ser Pro Lys Leu Leu
1               5                   10

Ile Tyr
    15

(2) INFORMATION FOR SEQ ID NO: 70:

(i) SEQUENCE CHARACTERISTICS:
        (A) LENGTH:     7 amino acids
        (B) TYPE:       amino acid
        (D) TOPOLOGY:   linear (ii) MOLECULE TYPE:      peptide (xi) SEQUENCE DESCRIPTION: SEQ ID NO: 70:

Arg Ala Ser Ile Arg Phe Ser
1               5       7

(2) INFORMATION FOR SEQ ID NO: 71:

(i) SEQUENCE CHARACTERISTICS:
        (A) LENGTH:     32 amino acids
        (B) TYPE:       amino acid
        (D) TOPOLOGY:   linear (ii) MOLECULE TYPE:      peptide (xi) SEQUENCE DESCRIPTION: SEQ ID NO: 71:

Gly Val Pro Asp Arg Phe Ser Gly Ser Gly Ser Gly Thr
1               5                   10

Asp Phe Thr Leu Lys Ile Ser Arg Val Glu Ala Glu Asp
    15                  20                  25

Val Gly Val Tyr Phe Cys
            30

(2) INFORMATION FOR SEQ ID NO: 72:

(i) SEQUENCE CHARACTERISTICS:
        (A) LENGTH:     9 amino acids
        (B) TYPE:       amino acid
        (D) TOPOLOGY:   linear (ii) MOLECULE TYPE:      peptide (xi) SEQUENCE DESCRIPTION: SEQ ID NO: 72:

Phe Gln Gly Thr His Val Pro Trp Thr
```

(2) INFORMATION FOR SEQ ID NO: 73:

(i) SEQUENCE CHARACTERISTICS:
        (A) LENGTH:   10 amino acids
        (B) TYPE:     amino acid
        (D) TOPOLOGY: linear (ii) MOLECULE TYPE:     peptide (xi) SEQUENCE DESCRIPTION: SEQ ID NO: 73:

```
Phe Gly Gly Gly Thr Lys Leu Glu Ile Lys
1               5                   10
```

(2) INFORMATION FOR SEQ ID NO: 74:

(i) SEQUENCE CHARACTERISTICS:
        (A) LENGTH:   19 amino acids
        (B) TYPE:     amino acid
        (D) TOPOLOGY: linear (ii) MOLECULE TYPE:     peptide (xi) SEQUENCE DESCRIPTION: SEQ ID NO: 74:

```
Met Tyr Leu Gly Leu Asn Tyr Val Phe Ile Val Phe Leu
1               5                   10
Leu Lys Gly Val Gln Ser
                15
```

(2) INFORMATION FOR SEQ ID NO: 75:

(i) SEQUENCE CHARACTERISTICS:
        (A) LENGTH:   30 amino acids
        (B) TYPE:     amino acid
        (D) TOPOLOGY: linear (ii) MOLECULE TYPE:     peptide (xi) SEQUENCE DESCRIPTION: SEQ ID NO: 75:

```
Glu Val Gln Leu Val Glu Ser Gly Gly Gly Leu Val Gln
1               5                   10
Pro Gly Gly Ser Met Arg Leu Ser Cys Ala Ala Ser Gly
15                  20                  25
Phe Thr Phe Ser
            30
```

(2) INFORMATION FOR SEQ ID NO: 76:

(i) SEQUENCE CHARACTERISTICS:
        (A) LENGTH:   5 amino acids
        (B) TYPE:     amino acid
        (D) TOPOLOGY: linear (ii) MOLECULE TYPE:     peptide (xi) SEQUENCE DESCRIPTION: SEQ ID NO: 76:

```
Asp Ala Trp Met Asp
1               5
```

(2) INFORMATION FOR SEQ ID NO:77:

(i) SEQUENCE CHARACTERISTICS:
        (A) LENGTH:   14 amino acids
        (B) TYPE:     amino acid
        (D) TOPOLOGY: linear (ii) MOLECULE TYPE:       peptide (xi) SEQUENCE DESCRIPTION: SEQ ID NO: 77:

Trp Val Arg Gln Ser Pro Gly Lys Gly Leu Glu Trp Val
1               5                   10

Ala
14

(2) INFORMATION FOR SEQ ID NO: 78:

(i) SEQUENCE CHARACTERISTICS:
           (A) LENGTH:    19 amino acids
           (B) TYPE:      amino acid
           (D) TOPOLOGY:  linear (ii) MOLECULE TYPE:       peptide (xi) SEQUENCE DESCRIPTION: SEQ ID NO: 78:

Glu Ile Arg Asn Lys Ala Asn Asn His Ala Thr Tyr Tyr
1               5                   10

Asp Glu Ser Val Lys Gly
            15

(2) INFORMATION FOR SEQ ID NO: 79:

(i) SEQUENCE CHARACTERISTICS:
           (A) LENGTH:    32 amino acids
           (B) TYPE:      amino acid
           (D) TOPOLOGY:  linear (ii) MOLECULE TYPE:       peptide (xi) SEQUENCE DESCRIPTION: SEQ ID NO: 79:

Arg Phe Thr Ile Ser Arg Asp Asp Ser Lys Ser Thr Val
1               5                   10

Tyr Leu Gln Met Asn Ser Leu Arg Ala Glu Asp Thr Ala
15                  20                  25

Leu Tyr Tyr Cys Thr Gly
            30

(2) INFORMATION FOR SEQ ID NO: 80:

(i) SEQUENCE CHARACTERISTICS:
           (A) LENGTH:    4 amino acids
           (B) TYPE:      amino acid
           (D) TOPOLOGY:  linear (ii) MOLECULE TYPE:       peptide (xi) SEQUENCE DESCRIPTION: SEQ ID NO: 80:

Glu Phe Ala Asn
1           4

(2) INFORMATION FOR SEQ ID NO: 81:

(i) SEQUENCE CHARACTERISTICS:
           (A) LENGTH:    11 amino acids
           (B) TYPE:           amino acid
           (D) TOPOLOGY:  linear (ii) MOLECULE TYPE:       peptide (xi) SEQUENCE DESCRIPTION: SEQ ID NO: 81:

Trp Gly Gln Gly Thr Leu Val Thr Val Ser Ser
1               5                   10

(2) INFORMATION FOR SEQ ID NO: 82:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 82:

```
CCCGGATCCT TTAAAAGGTG TCCAGTGTGA AGTGCAGATG                    40

GTGGAGTCTG                                                     50
```

(2) INFORMATION FOR SEQ ID NO: 83:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 83:

```
GAATTCGGGG CTAGCACTAG AGACAGTGAC CAGAGTCCCT                    40

TGGCCCCAG                                                      49
```

(2) INFORMATION FOR SEQ ID NO: 84:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 84:

```
AGTGCAGATG GTGGAGTCTG GGGGAGGCTT AGTGCAGCCT GGAGGGTCCC         50

TGAGACTCTC CTGTGCAGCC TCTGGATTCG CTTTCAGTAG                    90

CTATGCCATG T                                                  101
```

(2) INFORMATION FOR SEQ ID NO: 85:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 85:

```
CTTGATAGTA GGCGTAATTA CCACCACTAC TAATTTCTGC GACCCACTCC         50

AGCCCCTTCC CTGGAGCCTG GCGAACCCAA GACATGGCAT                    90

AGCTACTGAA A                                                  101
```

(2) INFORMATION FOR SEQ ID NO: 86:

(i) SEQUENCE CHARACTERISTICS:
        (A) LENGTH: 101 base pairs
        (B) TYPE: nucleic acid
        (C) STRANDEDNESS: single (D) TOPOLOGY:   linear (ii) MOLECULE TYPE:      DNA (xi) SEQUENCE DESCRIPTION: SEQ ID NO: 86:

TAATTACGCC TACTATCAAG ACACTGTGAC GGGCCGATTC ACCATCTCCA         50

GAGACAATTC CAAGAACACC CTGTACCTGC AAATGAACAG                   90

TCTGAGGGCT G                                                 101

(2) INFORMATION FOR SEQ ID NO: 87:

(i) SEQUENCE CHARACTERISTICS:
        (A) LENGTH:    101 base pairs
        (B) TYPE:      nucleic acid
        (C) STRANDEDNESS: single
        (D) TOPOLOGY:  linear (ii) MOLECULE TYPE:      DNA (xi) SEQUENCE DESCRIPTION: SEQ ID NO: 87:

CCAGAGTCCC TTGGCCCCAG TAAGCAAACC AGGCCGGGAT ACCGTAGTCC         50

TCCCTTGCAC AGTAATACAC GGCCGTGTCC TCAGCCCTCA                   90

GACTGTTCAT T                                                 101

(2) INFORMATION FOR SEQ ID NO: 88:

(i) SEQUENCE CHARACTERISTICS:
        (A) LENGTH:    66 base pairs
        (B) TYPE:      nucleic acid
        (C) STRANDEDNESS: single
        (D) TOPOLOGY:  linear (ii) MOLECULE TYPE:      DNA (xi) SEQUENCE DESCRIPTION: SEQ ID NO: 88:

GGGAAGCTTG ATATCCACCA TGAAGTTGCC TGTTAGGCTG                   40

TTGGTGCTGA TGTTCTGGAT TCCTGC                                 66

(2) INFORMATION FOR SEQ ID NO: 89:

(i) SEQUENCE CHARACTERISTICS:
        (A) LENGTH:    66 base pairs
        (B) TYPE:      nucleic acid
        (C) STRANDEDNESS: single
        (D) TOPOLOGY:  linear (ii) MOLECULE TYPE:      DNA (xi) SEQUENCE DESCRIPTION: SEQ ID NO: 89:

GGGAAGCTTG ATATCCACCA TGAAGTTGCC TGTTAGGCTG TTGGTGCTGA         50

TGTTCTGGAT TCCTGC                                            66

(2) INFORMATION FOR SEQ ID NO:90:

(i) SEQUENCE CHARACTERISTICS:
        (A) LENGTH:    100 base pairs
        (B) TYPE:      nucleic acid
        (C) STRANDEDNESS: single
        (D) TOPOLOGY:  linear (ii) MOLECULE TYPE:      DNA (xi) SEQUENCE DESCRIPTION: SEQ ID NO: 90:

CTGATGTTCT GGATTCCTGC TTCCAGCAGT GATGTTTTGA TGACCCAAAC         50

```
TCCTCTCTCC CTGCCTGTCA CTCCAGGAGA GCCAGCCTCC ATCTCTTGCA            100
```

(2) INFORMATION FOR SEQ ID NO: 91:

(i) SEQUENCE CHARACTERISTICS:
        (A) LENGTH:    100 base pairs
        (B) TYPE:      nucleic acid
        (C) STRANDEDNESS: single
        (D) TOPOLOGY:  linear (ii) MOLECULE TYPE:     DNA (xi) SEQUENCE DESCRIPTION: SEQ ID NO: 91:

```
CTGTGGAGAC TGGCCTGGTT TCTGCAGGTA CCATTCTAAA TAGGTGTTTC             50

CATTACTATG TACAATGCTC TGACTAGATC TGCAAGAGAT GGAGGCTGGC            100
```

(2) INFORMATION FOR SEQ ID NO: 92:

(i) SEQUENCE CHARACTERISTICS:
        (A) LENGTH:    100 base pairs
        (B) TYPE:      nucleic acid
        (C) STRANDEDNESS: single
        (D) TOPOLOGY:  linear (ii) MOLECULE TYPE:     DNA (xi) SEQUENCE DESCRIPTION: SEQ ID NO: 92:

```
CGAACGTGTA CGGAACATGT GAACCTTGAA AGCAGTAATA AATTCCCACA             50

TCCTCAGCCT CCACTCTGCT GATCTTGAGT GTGAAATCTG TCCCTGATCC            100
```

(2) INFORMATION FOR SEQ ID NO: 93:

(i) SEQUENCE CHARACTERISTICS:
        (A) LENGTH:    394 base pairs
        (B) TYPE:      nucleic acid
        (C) STRANDEDNESS: single
        (D) TOPOLOGY:  linear (ii) MOLECULE TYPE:     DNA (xi) SEQUENCE DESCRIPTION: SEQ ID NO: 93:

```
ATG AAG TTG CCT GTT AGG CTG TTG GTG CTG ATG TTC TGG ATT CCT        45

GCT TCC AGC AGT GAT GTT TTG ATG ACC CAA ACT CCT CTC TCC CTG        90

CCT GTC ACT CCA GGA GAG CCA GCC TCC ATC TCT TGC AGA TCT AGT       135

CAG AGC ATT GTA CAT AGT AAT GGA AAC ACC TAT TTA GAA TGG TAC       180

CTG CAG AAA CCA GGC CAG TCT CCA CAG CTC CTG ATC TAC AAA GTT       225

TCC ATC CGA TTT TCT GGG GTC CCA GAC AGG TTC AGT GGC AGT GGA       270

TCA GGG ACA GAT TTC ACA CTC AAG ATC AGC AGA GTG GAG GCT GAG       315

GAT GTG GGA ATT TAT TAC TGC TTT CAA GGT TCA CAT GTT CCG TAC       360

ACG TTC GGA GGG GGG ACC AAG CTG GAA ATA AAA C                     394
```

(2) INFORMATION FOR SEQ ID NO: 94:

(i) SEQUENCE CHARACTERISTICS:
        (A) LENGTH:    318 base pairs
        (B) TYPE:      nucleic acid
        (C) STRANDEDNESS: single
        (D) TOPOLOGY:  linear (ii) MOLECULE TYPE:     DNA (xi) SEQUENCE DESCRIPTION: SEQ ID NO: 94:

| | | | | | | | | | | | | | | |
|---|---|---|---|---|---|---|---|---|---|---|---|---|---|---|
| ATG | GAC | TTT | GGG | CTC | AGC | TTG | GTT | TTC | CTT | GTC | CTT | ATT | TTA AAA | 45 |
| GGT | GTC | CAG | TGT | GAA | GTG | CAG | ATG | GTG | GAG | TCT | GGG | GGA | GGC TTA | 90 |
| GTG | CAG | CCT | GGA | GGG | TCC | CTG | AGA | CTC | TCC | TGT | GCA | GCC | TCT GGA | 135 |
| TTC | GCT | TTC | AGT | AGC | TAT | GCC | ATG | TCT | TGG | GTT | CGC | CAG | GCT CCA | 180 |
| GGG | AAG | GGG | CTG | GAG | TGG | GTC | GCA | GAA | ATT | AGT | AGT | GGT | GGT AAT | 225 |
| TAC | GCC | TAC | TAT | CAA | GAC | ACT | GTG | ACG | GGC | CGA | TTC | ACC | ATC TCC | 270 |
| AGA | GAC | AAT | TCC | AAG | AAC | ACC | CTG | TAC | CTG | CAA | ATG | AAC | AGT CTG | 315 |
| AGG | | | | | | | | | | | | | | 318 |

(2) INFORMATION FOR SEQ ID NO: 95:

(i) SEQUENCE CHARACTERISTICS:
        (A) LENGTH: 131 amino acids
        (B) TYPE: amino acid
        (D) TOPOLOGY: linear (ii) MOLECULE TYPE: peptide (xi) SEQUENCE DESCRIPTION: SEQ ID NO: 95:

Met Lys Leu Pro Val Arg Leu Leu Val Leu
         5               10

Met Phe Trp Ile Pro Ala Ser Ser Ser Asp
         15             20

Val Leu Met Thr Gln Thr Pro Leu Ser Leu
         25             30

Pro Val Thr Pro Gly Glu Pro Ala Ser Ile
         35             40

Ser Cys Arg Ser Ser Gln Ser Ile Val His
         45             50

Ser Asn Gly Asn Thr Tyr Leu Glu Trp Tyr
         55             60

Leu Gln Lys Pro Gly Gln Ser Pro Gln Leu
         65             70

Leu Ile Tyr Lys Val Ser Ile Arg Phe Ser
         75             80

Gly Val Pro Asp Arg Phe Ser Gly Ser Gly
         85             90

Ser Gly Thr Asp Phe Thr Leu Lys Ile Ser
         95             100

Arg Val Glu Ala Glu Asp Val Gly Ile Tyr
         105           110

Tyr Cys Phe Gln Gly Ser His Val Pro Tyr
         115           120

Thr Phe Gly Gly Gly Thr Lys Leu Glu Ile
         125           130

Lys
131

(2) INFORMATION FOR SEQ ID NO: 96:

(i) SEQUENCE CHARACTERISTICS:
        (A) LENGTH: 139 amino acids
        (B) TYPE: amino acid
        (D) TOPOLOGY: linear (ii) MOLECULE TYPE:       peptide (xi) SEQUENCE DESCRIPTION: SEQ ID NO: 96:

Met Asp Phe Gly Leu Ser Leu Val Phe Leu
              5                  10

Val Leu Ile Leu Lys Gly Val Gln Cys Glu
             15                  20

Val Gln Met Val Glu Ser Gly Gly Gly Leu
             25                  30

Val Gln Pro Gly Gly Ser Leu Arg Leu Ser
             35                  40

Cys Ala Ala Ser Gly Phe Ala Phe Ser Ser
             45                  50

Tyr Ala Met Ser Trp Val Arg Gln Ala Pro
             55                  60

Gly Lys Gly Leu Glu Trp Val Ala Glu Ile
             65                  70

Ser Ser Gly Gly Asn Tyr Ala Tyr Tyr Gln
             75                  80

Asp Thr Val Thr Gly Arg Phe Thr Ile Ser
             85                  90

Arg Asp Asn Ser Lys Asn Thr Leu Tyr Leu
             95                 100

Gln Met Asn Ser Leu Arg Ala Glu Asp Thr
            105                 110

Ala Val Tyr Tyr Cys Ala Arg Glu Asp Tyr
            115                 120

Gly Ile Pro Ala Trp Phe Ala Tyr Trp Gly
            125                 130

Gln Gly Thr Leu Val Thr Val Ser Ser
            135             139